(12) United States Patent
Mackman et al.

(10) Patent No.: US 11,492,353 B2
(45) Date of Patent: Nov. 8, 2022

(54) **METHODS AND COMPOUNDS FOR TREATING *PARAMYXOVIRIDAE* VIRUS INFECTIONS**

(71) Applicant: Gilead Sciences, Inc., Foster City, CA (US)

(72) Inventors: Richard L. Mackman, Millbrae, CA (US); Jay P. Parrish, Redwood City, CA (US); Adrian S. Ray, Redwood City, CA (US); Dorothy Agnes Theodore, Castro Valley, CA (US)

(73) Assignee: Gilead Sciences, Inc., Foster City, CA (US)

( * ) Notice: Subject to any disclaimer, the term of this patent is extended or adjusted under 35 U.S.C. 154(b) by 139 days.

(21) Appl. No.: 16/879,491

(22) Filed: May 20, 2020

(65) Prior Publication Data

US 2021/0061806 A1   Mar. 4, 2021

Related U.S. Application Data

(60) Division of application No. 16/042,085, filed on Jul. 23, 2018, now Pat. No. 10,696,679, which is a division of application No. 14/613,719, filed on Feb. 4, 2015, now Pat. No. 10,065,958, which is a continuation of application No. 13/189,373, filed on Jul. 22, 2011, now abandoned.

(60) Provisional application No. 61/366,609, filed on Jul. 22, 2010.

(51) Int. Cl.
| | |
|---|---|
| *C07D 487/04* | (2006.01) |
| *C07H 19/04* | (2006.01) |
| *A61K 9/00* | (2006.01) |
| *A61K 31/706* | (2006.01) |
| *A61K 45/06* | (2006.01) |
| *C07H 7/06* | (2006.01) |
| *C07F 9/6561* | (2006.01) |

(52) U.S. Cl.
CPC ......... *C07D 487/04* (2013.01); *A61K 9/0078* (2013.01); *A61K 31/706* (2013.01); *A61K 45/06* (2013.01); *C07F 9/6561* (2013.01); *C07H 7/06* (2013.01); *C07H 19/04* (2013.01)

(58) Field of Classification Search
None
See application file for complete search history.

(56) References Cited

U.S. PATENT DOCUMENTS

| | | |
|---|---|---|
| 4,816,570 A | 3/1989 | Farquhar |
| 4,968,788 A | 11/1990 | Farquhar |
| 5,663,159 A | 9/1997 | Starrett, Jr. et al. |
| 5,792,756 A | 8/1998 | Starrett, Jr. et al. |
| 6,312,662 B1 | 11/2001 | Erion et al. |
| 6,475,985 B1 | 11/2002 | Wagner et al. |
| 6,476,030 B1 | 11/2002 | Carling et al. |
| 6,656,915 B1 | 12/2003 | Bantia et al. |
| 6,909,011 B2 | 6/2005 | Skranc et al. |
| 7,078,403 B1 | 7/2006 | Wu et al. |
| 7,105,493 B2 | 9/2006 | Sommadossi et al. |
| 7,125,855 B2 | 10/2006 | Bhat et al. |
| 7,166,604 B2 | 1/2007 | Watson et al. |
| 7,176,203 B2 | 2/2007 | Chambers et al. |
| 7,268,119 B2 | 9/2007 | Cook et al. |
| 7,285,658 B2 | 10/2007 | Cook et al. |
| 7,368,437 B1 | 5/2008 | Bojack et al. |
| 7,390,791 B2 | 6/2008 | Becker et al. |
| 7,429,571 B2 | 9/2008 | Chand et al. |
| 7,514,410 B2 | 4/2009 | Babu et al. |
| 7,560,434 B2 | 7/2009 | Babu et al. |
| 7,598,230 B2 | 10/2009 | Cook et al. |
| 7,608,597 B2 | 10/2009 | Sommadossi et al. |
| 7,713,941 B2 | 5/2010 | Cook et al. |
| 7,803,788 B2 | 9/2010 | Becker et al. |

(Continued)

FOREIGN PATENT DOCUMENTS

| | | |
|---|---|---|
| CN | 111265532 | 6/2020 |
| JP | 41017629 | 10/1966 |

(Continued)

OTHER PUBLICATIONS

Costa Rican Office Action in CR Appln. No. 2017-0000278, dated Apr. 8, 2021, 17 pages (with English translation).

(Continued)

*Primary Examiner* — Jeffrey S Lundgren
*Assistant Examiner* — Michael J Schmitt
(74) *Attorney, Agent, or Firm* — Fish & Richardson P.C.

(57) ABSTRACT

Provided are methods for treating Paramyxoviridae virus infections by administering ribosides, riboside phosphates and prodrugs thereof, of Formula I:

wherein the 1' position of the nucleoside sugar is substituted. The compounds, compositions, and methods provided are particularly useful for the treatment of Human parainfluenza and Human respiratory syncytial virus infections.

37 Claims, No Drawings

(56) References Cited

U.S. PATENT DOCUMENTS

| | | |
|---|---|---|
| 7,807,653 B2 | 10/2010 | Cook et al. |
| 7,842,672 B2 | 11/2010 | Boojamra et al. |
| 7,951,787 B2 | 5/2011 | McGuigan |
| 7,973,013 B2 * | 7/2011 | Cho .................. C07H 7/06 514/23 |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,568 B2 | 12/2011 | Narjes et al. |
| 8,119,607 B2 | 2/2012 | Francom et al. |
| 8,242,085 B2 | 8/2012 | Babu et al. |
| 8,318,682 B2 | 11/2012 | Butler et al. |
| 8,415,308 B2 | 4/2013 | Cho et al. |
| 8,455,451 B2 | 6/2013 | Cho et al. |
| 8,853,171 B2 | 10/2014 | Butler et al. |
| 8,871,737 B2 | 10/2014 | Smith et al. |
| 8,889,159 B2 | 11/2014 | Cleary et al. |
| 8,980,865 B2 | 3/2015 | Wang |
| 9,090,642 B2 | 7/2015 | Cho et al. |
| 9,243,022 B2 | 1/2016 | Beigelman et al. |
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,452,154 B2 | 9/2016 | Delaney et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 4/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,382,926 B2 | 7/2022 | Clarke et al. |
| 2003/0050229 A1 | 3/2003 | Sommadossi et al. |
| 2003/0092775 A1 | 5/2003 | Klaus et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Cho et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Hanrahan et al. |
| 2018/0346504 A1 | 12/2018 | Brak et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | O'Neil et al. |
| 2021/0403497 A1 | 12/2021 | Butler et al. |
| 2022/0081462 A1 | 3/2022 | Chun et al. |

FOREIGN PATENT DOCUMENTS

| | | |
|---|---|---|
| WO | WO1991019721 | 12/1991 |
| WO | WO1999045029 | 9/1999 |
| WO | WO2000056734 | 9/2000 |
| WO | WO-200075157 A1 | 12/2000 |
| WO | WO2001032153 | 5/2001 |
| WO | WO2001060315 | 8/2001 |
| WO | WO2001090121 | 11/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046331 | 6/2004 |
| WO | WO2004112687 | 12/2004 |
| WO | WO2005009418 | 2/2005 |

(56) References Cited

FOREIGN PATENT DOCUMENTS

| | | |
|---|---|---|
| WO | WO-2005092877 A1 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO-2006064033 A2 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO-2007062542 A2 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO-2007113294 A1 | 10/2007 |
| WO | WO2007135134 | 11/2007 |
| WO | WO2008005542 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO-2009132123 A1 | 10/2009 |
| WO | WO2009132135 | 10/2009 |
| WO | WO2010002877 | 1/2010 |
| WO | WO2010036407 | 4/2010 |
| WO | WO2010093608 | 8/2010 |
| WO | WO2010099458 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO-2011080568 A2 | 7/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012142523 | 10/2012 |
| WO | WO-2012158643 A1 | 11/2012 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2016107833 | 12/2014 |
| WO | WO2015069939 | 5/2015 |
| WO | WO2015173164 | 11/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017184668 | 10/2017 |
| WO | WO2017049060 | 3/2018 |
| WO | WO2018145148 | 8/2018 |
| WO | WO2018204198 | 11/2018 |
| WO | WO2019014247 | 1/2019 |
| WO | WO2021207049 | 10/2021 |

OTHER PUBLICATIONS

Damont et al., "Synthesis of 1'-C-Fluoromethyladenosine," Nucleosides, Nucleotides, and Nucleic Acids, 2007, 26:1431-1434.

Olsen et al., "A 7-Deaza-Adenosine Analog Is a Potent and Selective Inhibitor of Hepatitis C Virus Replication with Excellent Pharmacokinetic Properties," Antimicrobial Agents and Chemotherapy, 2004, 3944-3953.

Patani et al., "Bioisosterism: a rational approach in drug design," Chem. Rev., 1996, 96:3147-3176.

Brazilian Office Action in BR Appln. No. 12 2020 018569 4, dated Dec. 28, 2020, 21 pages.

Brazilian Office Action in BR Appln. No. 12 2020 019211 9, dated Jan. 19, 2021, 21 pages.

Brittain, Polymorphism in Pharmaceutical Solids, 2nd Edition, 2009, pp. 183-226, Informa Healthcare USA, Inc.

Chinese Office Action in CN Appln. No. 201580059613.5, dated Sep. 16, 2020, 7 pages.

Costa Rican Office Action in CR Appln. No. 2017-0165, dated Dec. 30, 2020, 17 pages (with English translation).

European Office Action in EP Appln. No. 16770866.8, dated Dec. 23, 2020, 4 pages.

Japanese Office Action in JP Appln. No. 2019-559276, dated Oct. 7, 2020, 6 pages (English translation only).

Lo et al., "GS-5734 and its parent nucleoside analog inhibit Filo-, Pneumo-, and Paramyxovirnses," Scientific Reports, 2017, 7(43395):1-7.

Murakami et al., Mechanism of Activation of PSI-7851 and Its Diastereoisomer PSI-7977, The Journal of Biological Chemistry, 2010, pp. 34337-34347, vol. 285, No. 45.

Uruguayan Office Action in UY Appln. No. 36.376, dated Jan. 11, 2021, 9 pages (with English translation).

Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.

Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.

Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.

Asbun, et al., Synthesis of 5-substituted Pyrimidines. II, Journal of Organic Chemistry, 1968, pp. 140-142, vol. 31.

Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.

Balzarini, et al., Inhibition of Feline (FIPV) and Human (SARS) Coronavirus by Semisynthetic Derivatives of Glycopeptide Antibiotics, Antiviral Research, 2006, pp. 20-33, vol. 72.

Bandini, et al., Indium tribromide: a highly effective catalyst for the addition of trimethylsilyl cyanide to α-hetero-substituted ketone, Tetrahedron Letters, 2001, pp. 3041-3043. vol. 42.

Barker, et al., 2,3,5-Tri-O-benzyl-D-ribosyl and -L-arabinosyl Bromides, Journal of Organic Chemistry, 1961, pp. 4605-4609, vol. 26, No. 11.

Barl, et al., The halogen/magnesium-exchange using iPrMgCl•LiCl and related exchange reagents, Heterocycles, Jan. 2014, pp. 827-844, vol. 88, No. 2.

Belokon, et al., Optimized catalysts for the asymmetric addition of trimethylsilyl cyanide to aldehydes and ketones, Tetrahedron, 2001, pp. 771-779, vol. 57.

(56) References Cited

OTHER PUBLICATIONS

Benksim, et al., A Novel Stereospecific Synthesis of Glycosyl Cyanides from 1,2-O-sulfinyl Derivatives, Organic Letters, 2004, pp. 3913-3915, vol. 6, No. 22.
Benzaria, et al., Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.
Bio, et al., Practical Synthesis of a Potent Hepatitis C Virus RNA Replication Inhibitor, J. Org. Chem., 2004, pp. 6257-6266, vol. 69, No. 19.
Bobeck, et al., Advances in Nucleoside Monophosphate Prodrugs as Anti-HCV Agents, Antiviral Therapy, 2010, pp. 935-950, vol. 15.
Bojack, et al., Design and Synthesis of Inhibitors of Adenosine and AMP Deaminases, Organic Letters, 2001, pp. 839-842, vol. 3, No. 6.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Brown, Progress towards improving antiviral therapy for hepatitis C virus polymerase inhibitors. Part O: Nucleoside analogues, 2009, pp. 709-725, vol. 18.
Bullard-Feibelman, et al., The FDA-approved drug Sofosbuvir inhibits Zika Virus infection, Antiviral Res., Jan. 1, 2018, pp. 134-140, vol. 137.
Burns, A Glimmer of Hope for Fatal Feline Disease, JAVMAnews, Dec. 15, 2017, 5 pages.
Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.
Cabirol, et al., Robust and Efficient, yet Uncatalyzed, Synthesis of Triarylsilyl-protected Cyanohydrins from Ketones, 2008, pp. 2446-2449, vol. 73.
Caira, Crystalline Polymorphism of Organic Compounds, Topics in Current Chemistry, 1998, pp. 163-208, vol. 198.
Calès, et al., Treatment of liver fibrosis: clinical aspects, Gastroentérologie Clinique et Biologique, 2009, pp. 958-966, vol. 33, No. 10-11.
Calisher, et al., Antigenic Relationships between Flaviviruses as Determined by Cross-neutralization Tests with Polyclonal Antisera, Journal of General Virology, 1989, pp. 37-43, vol. 70.
Camps, Studies on Structurally Simple -αβ-butenolides-II, Tetrahedron, 1982, pp. 2395-2402, vol. 38, No. 15.
Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.
Chapman, et al., RSV604, a Novel Inhibitor of Respiratory Syncytial Virus Replication, Antimicrobial Agents and Chemotherapy, 2007, pp. 3346-3353, vol. 51, No. 9.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Cho, et al., Synthesis and antiviral Activity of a Series of 1'-Substituted 4-aza-7,9-dideazaadenosine C-Nucleosides, Bioorganic & Medicinal Chemistry Letters, 2012, pp. 2705-2707, vol. 22.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Clarke, et al., Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases, Bioorganic & Medicinal Chemistry Letters, Apr. 29, 2015, pp. 2484-2487, vol. 25.
Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Dai, et al., Synthesis of 2'-C-β-Fluoromethyluridine, Organic Letters, 2003, pp. 807-810, vol. 5, No. 6.
De Clercq, Antiviral Drugs: Current State of the Art, J. Clin. Virol., 2001, pp. 73-89, vol. 22, No. 1.
De Clercq, Molecular Targets for Antiviral Agents, The Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.24.11) Inhibitors, J. Med. Chem., 1994, pp. 498-511, vol. 37, No. 4.
Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4-f][1,2,4]triazines as Inhibitors of Adenosine and AMP Deaminasses, J. Chem. Soc., Perkin Trans. 1, 1999, pp. 2937-2942.
Dudfield, P. et al., Synthesis of C-ribosyl imidazo[2,1-f][1,2,4]triazines as inhibitors of adenosine and AMP deaminases, J. Chem. Soc, Perkin Trans 1, 1999, pp. 2929-2936.
Dymock, et al., Novel approaches to the treatment of hepatitis C virus infection, Antiviral Chemistry & Chemotherapy, 2000, pp. 79-96, vol. 11, No. 2.
El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.
Farquhar, et al., Biologically Reversible Phosphate-Protective Groups, Journal of Pharmaceutical Sciences, 1983, pp. 324-325, vol. 72, No. 3.
Fukumoto, et al., Viral Dynamics of Hepatiis C Early After Orthotopic Liver Transplantation: Evidence for Rapid Turnover of Serum Virions, Hepatology, 1996, pp. 1351-1354, vol. 24.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, et al., Protective Groups in Organic Synthesis, 1991, pp. 118-142, John Wiley & Sons.
Gudmundsson, et al., Synthesis of imidazo[1,2-a]pyridine C-Nucleosides with an Unexpected Site of Ribosylation, Journal of Organic Chemistry, 1997, pp. 3453-3459, vol. 62.
Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.

(56) References Cited

OTHER PUBLICATIONS

Gunic, et al., Cyclic monophosphate prodrugs of base-modified 2'-C-methyl ribonucleosides as potent inhibitors of hepatitis C virus RNA replication, Bioorganic & Medicinal Chemistry Letters, 2007, pp. 2452-2455, vol. 17.
Hamann, et al., Synthesis and antiviral evaluation of 7,9-dideaza-8-thiapurine C-nucleoside derivatives, Collection Symposium Series, 2008, pp. 347-349, vol. 10.
Hamann, et al., Synthesis and antiviral evaluation of thieno[3,4-d]pyrimidine C-nucleoside analogues of 2',3'-dideoxy- and 2',3'-dideoxy-2',3'-didehydro-adenosine and -inosine, Bioorganic & Medicinal Chemistry, 2009, pp. 2321-2326, vol. 17.
Han, et al., Synthesis of 1-Chloroacetyl-1-dehydroxy-2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.
Haraguchi, K. et al., Stereoselective Synthesis of 1'-C-Branched Uracil Nucleosides From Uridine, Nucleosides & Nucleotides, 1995, pp. 417-420, vol. 14, No. 3-5.
Harki, et al., Synthesis and Antiviral Activity of 5-Substituted Cytidine Analogues: Identification of Potent Inhibitor of Viral RNA-Dependent RNA Polymerases, Journal of Medicinal Chemistry, 2006, pp. 6166-6169, vol. 49, No. 21.
Hayashi, et al., C-Nucleosides, A Synthesis of 2-Substituted 7-(b-D-Ribofuranosyl)-Pyrrolo[2,1-f]-1,2,4-Triazines. A New Type of "Purine Like" C-Nucleoside, Heterocycles, 1992, pp. 569-574, vol. 34, No. 3.
Hecker, et al., Liver Targeted Prodrugs of 2'-C-Methyladenosine for Therapy of Hepatitis C Virus Infection, J. Med. Chem., 2007, pp. 3891-3896, vol. 50, No. 16.
Hoffmann, et al., When, in the context of drug design, can a fluorine atom successfully substitute a hydroxyl group?, International Journal of Quantum Chemistry, 2002, pp. 419-427, vol. 89.
Itoh, et al., Divergent and Stereocontrolled Approach to the Synthesis of Uracil Nucleosides Branched at the Anomeric Position, J. Org. Chem, 1995, pp. 656-662, vol. 60.
Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.
Kabat, et al., Nucleosides, CXLVIII, Synthesis of 6-(β-D-Ribofuranosyl)picolinamide: A Novel C-Nucleoside from D-Ribonolactone, Chemical & Pharmaceutical Bulletin, 1988, pp. 634-640, vol. 36, No. 2.
Khamnei, et al., Neighboring Group Catalysis in the Design of Nucleotide Prodrugs, J. Med. Chem., 1996, pp. 4109-4115, vol. 39, No. 20.
Kim, et al., Reversal of the Progression of Fatal Coronavirus Infection in Cats by a Broad-Spectrum Coronavirus Protease Inhibitor, PLOS Pathogens, Mar. 30, 2016, 18 pages.
Klumpp, et al., The Novel Nucleoside Analog R1479 (4'-Azidocytidine) is a Potent Inhibitor of NS5B-dependent RNA Synthesis and Hepatitis C virus Replication in Cell Culture, Journal of Biological Chemistry, 2006, pp. 3793-3799, vol. 281, No. 7.
Knaggs, et al. A QSAR Study Investigating the Effect of L-Alanine Ester Variation on the Anti-HIV Activity of Some Phosphoramidate Derivatives of d4T, 2000, pp. 2075-2078.
Knutsen, et al., Synthesis of Imidazo-fused Bridgehead-nitrogen C-Nucleosides : Coupling-Elimination Reactions of 2,5-Anhydro-3,4,6-tri-O-benzoyl-D-allonic Acid, J. Chem. Soc. Perkin Trans 1, 1985, pp. 621-630.
Knutsen, et al., Synthesis of Imidazo-fused Bridgehead-nitrogen C-Nucleosides via Dehydrative Coupling Reactions of 2,5-Anhydro-3,4,6-tri-O-benzoyl-D-allonic Acid, J. Chem. Soc. Perkin Trans 1, 1984, pp. 229-238.
Kobe, et al., Use of Distance Geometry Approach for the In Vitro Antiviral Activity Evaluation of N-bridgehead C-nucleosides, European J. Med. Chem., 1992, pp. 259-266, vol. 27, No. 3.
Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate, Journal of Medicinal Chemistry, 1995, pp. 3941-3950, vol. 38, No. 20.
Lefebvre, et al., Synthesis, Decomposition Pathways and 'In Vitro' Evaluation of Bioreversible Phosphotriesters of Azt, Nucleosides, Nucleotides & Nucleic Acids, 1995, pp. 763-766, vol. 14, No. 3-5.
Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.
Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.
Lu, Chengping, Veterinary Microbiology 5th edition, Jan. 31, 2013, p. 431, China Agriculure Press (No English Translation available).
Martell, et al., Hepatitis C Virus (HCV) Circulates as a Population of Different but Closely Related Genomes: Quasispecies Nature of HCV Genome Distribution, Journal of Virology, 1992, pp. 3225-3229, vol. 6695.
Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.
Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.
Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.
McGuigan, et al. Application of Phosphoramidate ProTide Technology Significantly Improves Antiviral Potency of Carbocyclic Adenosine Derivatives, 2006, pp. 7215-7226.
McGuigan, et al., Intracellular Delivery of Bioactive AZT Nucleotides by Aryl Phosphate Derivatives of AZT, J. Med. Chem., 1993, pp. 1048-1052, vol. 36, No. 8.
Meppen, et al., Cyclic phosphoramidates as prodrugs of 2'-C-methylcytidine, European Journal of Medicinal Chemistry, 2009, pp. 3765-3770, vol. 49, No. 9.
Meppen, et al., Medi-404—A Prodrug Approach for the Treatment of HCV Infection, Abstracts of papers, 236th ACS National Meeting, Philadelphia, PA, United States, Aug. 17-21, 2008.
Metobo, et al., Practical synthesis of 1'-substituted Tubercidin C-nucleoside analogs, Tetrahedron Letters, Feb. 2012, pp. 484-486, vol. 53, No. 5.
Migliaccio, et al., Characterization of Resistance to Non-obligate Chain-terminating Ribonucleoside Analogs That Inhibit Hepatitis C Virus Replication in vitro, The Journal of Biological Chemistry, 2003, pp. 49164-49170, vol. 278, No. 49.
Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.
Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.
Moennig, et al., The Pestiviruses, Advances in Virus Research, 1992, pp. 53-98, vol. 41.
Moradpour, et al., Replication of hepatitis C virus, Nature Reviews Microbiology, 2007, pp. 453-463, vol. 5, No. 6.
Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.
Murakami, et al., Mechanism of Activation of Beta-D-2'-Fluoro-2'-C-Methylcytidine and Inhibition of Hepatitis C Virus NS5B RNA Polymerase, Antimicrob Agents Chemother., Feb. 2007, pp. 503-509, vol. 51, No. 2.
Murphy, et al., The Nucleoside Analog GS-441524 Strongly Inhibits Feline Infectious Peritonisitis (FIP) Virus in Tissue Culture and Experimental Cat Infection Studies, Veterinary Microbiology, 2018, pp. 226-233, vol. 219.

(56) References Cited

OTHER PUBLICATIONS

Neumann, et al., Hepatitis C Viral Dynamics in Vivo and the Antiviral Efficacy of Interferon-α Therapy, Science, 1998, pp. 103-107, vol. 282.
Nishimura, et al., Synthesis of pyrrolo[2,1-f][1,2,4]triazine C-nucleosides. Isosteres of sangivamycin, tubercidin, and toyocamycin, Carbohydrate Research, 2001, pp. 77-82, vol. 331.
Ogura, et al., Reaction of Ethynyl Compounds with Lactones, Journal of Organic Chemistry, 1972, pp. 72-75, vol. 37, No. 1.
Otter, B. et al., Conformational Properties of Purine-Like C-Nucleosides, Nucleosides & Nucleotides, 1996, pp. 793-807, vol. 15, No. 1-3.
Pankiewicz, et al., C-Nucleoside Analogues of Nicotinamide Mononucleotide (NMN), Nucleosides and Nucleotides, 1988, pp. 589-593, vol. 7, No. 5&6.
Pankiewicz, et al., Efficient Synthesis of 5-(β-D-Ribofuranosyl)nicotinamide and its α-Isomer, Journal of Organic Chemistry, 1988, pp. 3473-3479, vol. 53.
Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.
Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31.
Patil, et al., Synthesis of some new thieno[3,4-d]pyrimidines and their C-nucleosides, Journal of Heterocyclic Chemistry, 1993, pp. 509-515, vol. 30, No. 2.
Perrone, et al., Application of the Phosphoramidate ProTide Approach to 4'-Azidouridine Confers Sub-micromolar Potency versus Hepatitis C Virus on an Inactive Nucleoside, Journal of Medicinal Chemistry, 2007, pp. 1840-1849, vol. 50, No. 8.
Piccirilli, et al., A Direct Route to 3-(D-Ribofuranosyl)pyridine Nucleosides, Helvetica Chimica Acta, 1991, pp. 397-406, vol. 74.
Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.
Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.
Porter, et al., Zika virus, drug discovery, and student projects, ScienceBlogs, Mar. 9, 2016, 7 pages.
Puech, et al., Intracellular Delivery of Nucleoside Monophosphates through a Reductase-mediated Activation Process, Antiviral Research, 1993, pp. 155-174, vol. 22, No. 4.
Ramasamy, et al., Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor, J. Med. Chem., 1986, pp. 2231-2235, vol. 29, No. 11.
Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.
Reddy, et al., Stereoselective Synthesis of Nucleoside Monophosphate HepDirectTM Prodrugs, Tet. Lett., 2005, pp. 4321-4324, vol. 46.
Sacramento, et al., The clinically approved antiviral drug Sofosbuvir inhibits Zika Virus replication, Nature, Jan. 18, 2017.
Schul, et al., A Dengue Fever Viremia Model in Mice Shows Reduction in Viral Replication and Suppression of the Inflammatory Response after Treatment with Antiviral Drugs, Journal of Infectious Diseases, 2007, pp. 665-674, vol. 195.
Schultz, Prodrugs of Biologically Active Phosphate Esters, Bioorganic & Medicinal Chemistry, 2003, pp. 885-898, vol. 11.
Scott, et al., Interferon-a-2b Plus Ribavirin: A Review of its Use in the Management of Chronic Hepatitis C, Drugs, 2002, pp. 507-556, vol. 62, No. 3.
Shekunov, et al., Crystallization processes in pharmaceutical technology and drug delivery design, Journal of Crystal Growth, 2000, pp. 122-136, vol. 211.
Siegel, Discovery and Synthesis of a Phosphoramidate Prodrug of a Pyrrolo[2,1-f][triazin-4-amino] Adenine C-Nucleoside(GS-5734) for the Treatment of Ebola and Emerging Viruses, J. Med. Chem., Feb. 14, 2017, 51 pages.
Siegel, et al., Supporting Information Discovery and Synthesis of a Phosphoramidate Prodrug of a Pyrrolo[2,1-f][triazin-4-amino] Adenine C-Nucleoside (GS-5734) for the Treatment of Ebola and Emerging Viruses Contents, J. Med. Chem., Jan. 26, 2017, 26 pages.
Silverman et al., The Organic Chemistry of Drug Design and Drug Action, 1992, pp. 19-23.
Silverman, The Organic Chemistry of Drug Design and Drug Action, 2nd Ed., 2004, pp. 29-34.
Srivastav, et al., Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication, Journal of Medicinal Chemistry, 2010, pp. 7156-7166, vol. 53, No. 19.
Tapia, et al., Combination of a Mutagenic Agent with a Reverse Transcriptase Inhibitor Results in Systematic Inhibition of HIV-1 Infection, Virology, 2005, pp. 1-8, vol. 338.
Uchiyama, et al., O-selective Phosphorylation of Nucleosides without N-protection, J. Org. Chem., Jan. 1, 1993, vol. 58, No. 2.
Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.
Venkatachalam, et al. Effect of change in nucleoside structure on the activation and antiviral activity of phosphoramidate derivatives, 2005, pp. 5408-5423.
Warren, et al., Therapeutic efficacy of the small molecules GS-5734 against Ebola virus in rhesus monkeys, Nature, Mar. 17, 2016, 19 pages.
Wu, et al., Synthetic Methodologies for C-NuScleosides, Synthesis, 2004, pp. 1533-1553, vol. 10.
Yamanaka, et al., Metabolic Studies on BMS-200475, a New Antiviral Compound Active against Hepatitis B Virus, Antimicrobial Agents and Chemotherapy, 1999, p. 190, vol. 43, No. 1.
Yoshimura, et al., Synthesis and Biological Evaluation of 1'-C-Cyano-Pyrimidine Nucleosides, Nucleosides & Nucleotides, 1996, pp. 305-324, vol. 15, No. 1-3.
Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.
Beer et al., "Characteristics of Filoviridae: Marburg and Ebola Viruses," Naturwissenschaften, 1999, 86:8-17.
Brands et al., "Crystallization-Induced Diastereomer Transformations," Chem. Rev., 2006, 106(7): 2711-2733.
Brotschi et al., "Bipyridyl and biphenyl DNA: A recognition motif based on interstrand aromatic stacking," Chemistry—A European Journal, 2005, 11(6):1911-1923.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Leyssen et al., "Molecular strategies to inhibit the replication of RNA Viruses," Antiviral Research, 2008, 78:9-25.
McGuigan et al., "Design, synthesis and biological evaluation of phosphorodiamidate prodrugs of antiviral and anticancer nucleosides," European Journal of Medical Chemistry, 2013, 70:326-340.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Bradley et al., "The Management of Community—Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.

(56) References Cited

OTHER PUBLICATIONS

Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.
CAS Registry No. 1809249-37-3, "L-Alanine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.
Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Fauquet et al., "Abbreviations for vertebrate virus species names", Archives of Virology, Dec. 31, 1999, pp. 1865-1880.
Kaewkhao et al., "High sensitivity methods to quantify chloroquine and its metabolite in human blood samples using LC-MS/MS", Bioanalysis, Mar. 2019, 11(5):333-347.
Kuzik et al., "Nebulized Hypertonic Saline in the Treatment of Viral Bronchiolitis in Infants", The Journal of Pediatrics, Sep. 2007, 151(3):266-270.e1.
Morris, "Mechanisms of action and therapeutic role of corticosteroids in asthma", J. Allergy Clin. Immunol., Jan. 1985, 75(1 Pt): 1-13.
Munster et al., "Hydroxychloroquine concentration-response relationships in patients with rheumatoid arthritis", Arthritis Rheumatology, Jun. 2002, 46(6):1460-1469.
Walker et al., "Plasma chloroquine and desethylchloroquine concentrations in children during and after chloroquine treatment for malaria.", British Journal Clinical Pharmacology, Dec. 1983, 16(6):701-705.
Wang et al., "Remdesivir and chloroquine effectively inhibit the recently emerged novel coronavirus (2019-nCoV) in vitro", Cell Research, 2020, 30:269-271.
Warren et al., "Protection against filovirus diseases by a novel broad-spectrum nucleoside analogue BCX4430", Nature, Apr. 2014, 508(7496):402-405.
Bowie et al., "RIG-I: tri-ing to discriminate between self and non-self RNA," Trends in Immunology, Apr. 2007, 28(4): 147-150.
Flint et al., "Functional analysis of cell surface-expressed hepatitis C virus E2 glycoprotein," J. Virol., Aug. 1999, 73(8): 6782-6790.
Freeman et al., "3 Prodrug Design for Phosphates and Phosphonates," Progress in Medicinal Chemistry, 1997, 34: 111-147.
Pelet et al., "High throughput screening assay for negative single stranded RNA virus polymerase inhibitors," J. Virol, Methods, Sep. 2005, 128(1-2): 29-36.
Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.
Wang et al., "ANNOVAR: functional annotation of genetic variants from high-throughput sequencing data," Nucleic Acids Research, 2010, 38(16): e164, 7 pages.
Yoon et al., "High-throughput screening-based identification of paramyxovims inhibitors," J. Biomol. Screen., Aug. 2008, 13(7): 591-608.
Indian Post Grant Opposition Hearing Notice in IN Patent Application No. 1328/CHENP/2013, dated Dec. 10, 2021, 12 pages.
Brazilian Office Action in BR Appln. No. 12 2020 020745, dated Jan. 21, 2021, 19 pages.
Foster et al., "Deuterium isotope effects in studies of drug metabolism," Trends in Pharmacological Sciences, Jan. 1984, 5:524-7.
George et al., "Preparation of silyl-and germylmetallic compounds," Journal of the American Chemical Society, Jan. 1960, 82(2):403-6.
Indian Office Action in IN Appln. No. 201948034308, dated Jun. 11, 2020, 5 pages.
Kalil et al., "Baricitinib plus Remdesivir for hospitalized adults with Covid-19," New England Journal of Medicine, Dec. 11, 2020, 13 pages.
Mossel et al., "Exogenous ACE2 expression allows refractory cell lines to support severe acute respiratory syndrome coronavirus replication," Journal of Virology, Mar. 15, 2005, 79(6):3846-50.
Notification of Formalities Examination for EA Patent Application No. 201390152, dated Apr. 2, 2013.
Notification of the Second Office Action for CN Patent Application No. 201180035776.1, dated Oct. 30, 2014, 5 pages (English translation).
Xie et al., "A nanoluciferase SARS-CoV-2 for rapid neutralization testing and screening of anti-infective drugs for COVID-19," Nature Communications, Oct. 15, 2020, 11(1):1-1.
Zhu et al., "A novel coronavirus from patients with pneumonia in China, 2019," New England Journal of Medicine, Jan. 24, 2020, 14 pages.
Aripo Patent Office, Form 21 and Substantive Examination Report (in English) for AP Application No. AP/P/2010/005439, dated Mar. 18, 2014.
Aripo Patent Office, Form 21 for AP Patent Application No. AP/P/2011/005818, dated Sep. 19, 2013.
Aripo Patent Office, Official Action (ARIPO Form No. 18) with Substantive Search and Examination Report for AP Application No. AP/P/2010/005414, dated Mar. 14, 2014.
Aripo Patent Office, Search and Exam Report for AP Application No. AP/P/2012/006189, dated Jun. 26, 2014.
Aripo Patent Office, Search Report for AP Patent Application No. AP/P/2011/005818, dated Sep. 19, 2013.
Australia Patent Office, First Examination Report for AU Patent Application No. 2009240630, dated Jun. 14, 2012.
Australia Patent Office, First Examination Report for AU Patent Application No. 2009240642, dated Aug. 2, 2012.
Australia Patent Office, Patent Examination Report No. 1 for AU Application No. 2011280910, dated Jun. 10, 2014.
Australia Patent Office, Patent Examination Report No. 1 for AU Application No. 2011306066, dated Nov. 21, 2013.
Australia Patent Office, Patent Examination Report No. 1 for AU Patent Application No. 2010213873, dated Jun. 4, 2014.
Australia Patent Office, Patent Examination Report No. 1 for AU Patent Application No. 2010295392, dated Sep. 16, 2014.
Australia Patent Office, Patent Examination Report No. 1 for AU Patent Application No. 2011282241, dated Jul. 9, 2014.
Brazilian Patent Office, Third Party Submission for BR 11 2013 001267-6, Jan. 15, 2019, 25 pages.
Brazilian Patent Office, Instructions to Third Party Submission, BR 11 2013 001267-6, Jan. 15, 2019, 6 pages.
Brazilian Patent Office, Response to Third Party Submission, BR 11 2013 001267-6, Jan. 15, 2019, 15 pages.
Brittain, 2016. Polymorphism in pharmaceutical solids. [Book].
Canadian Patent Office, Office Action for CA Patent Application No. 2,773,772, dated Aug. 12, 2014.
Chile Patent Office, First Office Action for CL Patent Application No. 1906-2011, dated Aug. 9, 2011.
Chile Patent Office, Opposition filed Against CL Patent Application 00076-2013, Jun. 18, 2014.
Chile Patent Office, Opposition for CL Patent Application No. 727-2013, Oct. 15, 2013.
Chile Patent Office, Second Office Action for CL Patent Application No. 1906-2011, dated Oct. 16, 2013.
China First Request For Invalidation to China Patent Application No. 201180035776.1, filed Jun. 1, 2020, 57 pages.
China Second Request For Invalidation to China Patent Application No. 201180035776.1, filed Jun. 11, 2020, 28 pages.

(56) References Cited

OTHER PUBLICATIONS

Chinese Patent Office, First Examination Report for CN Patent Application No. 200980120218.8, dated Nov. 13, 2012.
Chinese Patent Office, First Office Action for CN Patent Application No. 201080011690.0, dated Jun. 8, 2013.
Chinese Patent Office, Notification of Reexamination for CN Patent Application No. 200980120218.8, dated Sep. 1, 2014.
Chinese Patent Office, Notification of the First Office Action and Search Report for CN Patent Application No. 201080041902.X, dated Nov. 12, 2013.
Chinese Patent Office, Notification of the First Office Action for CN Patent Application No. 201180035776.1, dated Feb. 27, 2014.
Chinese Patent Office, Notification of the First Office Action, with Search Report, for CN Patent Application No. 201080041946.2, dated Dec. 18, 2013.
Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Office Action for CN Patent Application No. 200980114224.2, dated Aug. 19, 2013.
Chinese Patent Office, Office Action for CN Patent Application No. 200980114224.2, dated Nov. 30, 2012.
Chinese Patent Office, Office Action with Search Report for CN Patent Application No. 201180035281.9, dated Jun. 27, 2014.
Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.
Colombia Patent Office, First Examination Report (in English) for CO Patent Application No. 10-131479, dated Oct. 23, 2012.
Colombia Patent Office, First Examination Report for CO Patent Application No. 10-121513-5, dated Dec. 10, 2012.
Colombia Patent Office, Office Action for CO Application No. 13 004212, dated Dec. 4, 2013.
Colombia Patent Office, Office Action for CO Patent Application No. 11-109.501, dated Nov. 27, 2012.
Colombia Patent Office, Office Action for CO Patent Application No. 13-235103-1, dated Aug. 27, 2014.
Colombia Patent Office, Resolution 56673 for CO Patent Application 10-131479, Sep. 27, 2013.
Colombia Patent Office, Resolution No. 72986 for CO Patent Application No. 10-121513-5, Dec. 23, 2013.
Colombia Patent Office, Second Examination Report (in English) for CO Patent Application No. 10-131479, dated Jun. 20, 2013.
Colombian Patent Office, Office Action No. 425 for CO Patent Application No. 12 050 579, dated Jan. 21, 2014.
Ecuador Patent Office, Opposition for EC Patent Application No. SP-13-12451, Apr. 23, 2014.
Ecuador Patent Office, Opposition for EC Patent Application No. SP-2012-11817, May 27, 2013.
Ecuador Patent Office, Statement of Opposition for EC Patent Application No. SP-10-10609, Mar. 31, 2011.
El Salvador Patent Office, Official Action for SV National Phase Entry of International Application No. PCT/US2010/049471, dated Nov. 6, 2013.
Eurasian Patent Office, First Examination Report for EA Patent Application No. 201071128, dated Apr. 25, 2012.
Eurasian Patent Office, First Examination Report for EA Patent Application No. 201071170, dated Apr. 25, 2012.
Eurasian Patent Office, First Office Action for EA Patent Application No. 201190110/28, dated Apr. 26, 2012.
Eurasian Patent Office, First Office Action for EA Patent Application No. 201390141/28, with English translation.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Examination Report for EA Patent Application No. 201071170, dated Oct. 25, 2012.
Eurasian Patent Office, Second Office Action for EA Patent Application No. 201190110/28, dated Jan. 28, 2013.
Eurasian Patent Office, Third Examination Report for EA Patent Application No. 201071128, dated Apr. 29, 2013.
Eurasian Patent Office, Third Examination Report for EA Patent Application No. 201071170, dated Oct. 10, 2013.
Eurasian Patent Office, Third Office Action for EA Application No. 201190110/28, dated Oct. 18, 2013.
European Patent Office, Communication pursuant to Article 94(3) EPC for EP Patent Application No. 10763083.2, dated May 2, 2014.
European Patent Office, Communication pursuant to Article 94(3) EPC for EP Patent Application No. 11715792.5, dated Feb. 14, 2014.
European Patent Office, Communication under 161/162 for EP Patent Application No. 10704068.5, dated Sep. 6, 2011.
European Patent Office, Communication under 161/162 for EP Patent Application No. 10763083.2, dated May 11, 2012.
European Patent Office, Communication under 161/162 for EP Patent Application No. 11715792.5, dated Apr. 26, 2013.
European Patent Office, Communication under 161/162 for EP Patent Application No. 11743400.1, dated Feb. 26, 2013.
European Patent Office, Communication under 161/162 for EP Patent Application No. 11743709.5, dated Mar. 1, 2013.
European Patent Office, Extended European Search Report for EP Application No. 13194605.5, dated Mar. 13, 2014.
European Patent Office, First Office Action for EP Patent Application No. 10704068.5, dated Jun. 18, 2012.
European Patent Office, International Preliminary Report on Patentability and Written Opinion for PCT International Application No. PCT/US2009/041432, dated Oct. 26, 2010, 7 pages.
European Patent Office, International Preliminary Report on Patentability and Written Opinion for PCT International Application No. PCT/US2010/049471, dated Mar. 27, 2012, 7 pages.
European Patent Office, International Preliminary Report on Patentability and Written Opinion for PCT International Application No. PCT/US2010/049508, dated Mar. 27, 2012, 6 pages.
European Patent Office, International Preliminary Report on Patentability and Written Opinion for PCT International Application No. PCT/US2011/038253, dated Dec. 4, 2012, 6 pages.
European Patent Office, International Preliminary Report on Patentability and Written Opinion for PCT International Application No. PCT/US2011/044581, dated Jan. 22, 2013, 7 pages.
European Patent Office, International Preliminary Report on Patentability for PCT International Application No. PCT/US2009/041447, dated Oct. 26, 2010, 7 pages.
European Patent Office, International Preliminary Report on Patentability for PCT International Application No. PCT/US2010/023586, dated Aug. 16, 2011, 6 pages.
European Patent Office, International Preliminary Report on Patentability for PCT International Application No. PCT/US2011/028897, dated Mar. 26, 2013, 7 pages.
European Patent Office, International Preliminary Report on Patentability for PCT International Application No. PCT/US2011/029441, dated Mar. 26, 2013, 7 pages.
European Patent Office, International Preliminary Report on Patentability for PCT International Application No. PCT/US2011/045102, dated Jan. 22, 2013, 5 pages.
European Patent Office, International Preliminary Report on Patentability for PCT International Application No. PCT/US2015/057932, dated May 2, 2017, 11 pages.
European Patent Office, International Preliminary Report on Patentability for PCT International Application No. PCT/US2015/057933, dated May 2, 2017, 7 pages.
European Patent Office, International Preliminary Report on Patentability for PCT International Application No. PCT/US2015/057934, dated May 2, 2017, 14 pages.
European Patent Office, International Preliminary Report on Patentability for PCT International Application No. PCT/US2018/022166, dated Sep. 26, 2019, 8 pages.

(56) References Cited

OTHER PUBLICATIONS

European Patent Office, International Search Report and Written Opinion for PCT International Application No. PCT/US2009/041432, dated Aug. 11, 2009, 5 pages.
European Patent Office, International Search Report and Written Opinion for PCT International Application No. PCT/US2009/041447, dated Aug. 7, 2009, 5 pages.
European Patent Office, International Search Report and Written Opinion for PCT International Application No. PCT/US2010/023586, dated Aug. 4, 2010, 4 pages.
European Patent Office, International Search Report and Written Opinion for PCT International Application No. PCT/US2010/049471, dated Nov. 18, 2010, 5 pages.
European Patent Office, International Search Report and Written Opinion for PCT International Application No. PCT/US2010/049508, dated Nov. 5, 2010, 4 pages.
European Patent Office, International Search Report and Written Opinion for PCT International Application No. PCT/US2011/028897, dated Aug. 1, 2011, 6 pages.
European Patent Office, International Search Report and Written Opinion for PCT International Application No. PCT/US2011/029441, dated Aug. 1, 2011, 12 pages.
European Patent Office, International Search Report and Written Opinion for PCT International Application No. PCT/US2011/038253, dated Jul. 29, 2011, 9 pages.
European Patent Office, International Search Report and Written Opinion for PCT International Application No. PCT/US2011/044581, dated Nov. 7, 2011, 10 pages.
European Patent Office, International Search Report and Written Opinion for PCT International Application No. PCT/US2011/045102, dated Nov. 9, 2011, 8 pages.
European Patent Office, International Search Report and Written Opinion for PCT International Application No. PCT/US2015/057932, dated May 6, 2016, 17 pages.
European Patent Office, International Search Report and Written Opinion for PCT International Application No. PCT/US2015/057933, dated Jan. 21, 2016, 9 pages.
European Patent Office, International Search Report and Written Opinion for PCT International Application No. PCT/US2015/057934, dated Mar. 18, 2016, 20 pages.
European Patent Office, International Search Report and Written Opinion for PCT International Application No. PCT/US2017/028243, dated Aug. 29, 2017, 12 pages.
European Patent Office, International Search Report and Written Opinion for PCT International Application No. PCT/US2017/028251, dated Sep. 13, 2017, 22 pages.
European Patent Office, International Search Report and Written Opinion for PCT International Application No. PCT/US2018/022166, dated May 25, 2018, 13 pages.
European Patent Office, International Search Report and Written Opinion for PCT International Application No. PCT/US2018/029974, dated Sep. 18, 2018, 17 pages.
European Patent Office, International Search Report for PCT International Application No. PCT/US2016/052092, dated Oct. 11, 2016, 11 pages.
Franchetti et al., Antitumor Activity of C-Methyl-β-D-ribofuranosyladenine Nuceoside Ribonuceotide Reductase Inhibitors, J. Med. Chem. 2005, pp. 4983-4989, vol. 48.
Greene, T.W. and Wuts, P.G.M. (1991) Protective Groups in Organic Synthesis, published by John Wiley & Sons, v Inc., p. 1-4, 10-14, 47-53 and 100-103.
Harcourt, et al., Molecular Characterization of the Polymerase Gene and Genomic Termini of Nipah Virus, Virology, 2001, pp. 192-201, vol. 287.
India Notice of Post-Grant Opposition in India Patent Application No. 201727012821 (India Patent No. 332280, filed Jun. 30, 2020, 639 pages.
India Opposition Notice to India Patent Patent Application No. 1328/CHENP/2013 (India Patent No. 319927), filed Jun. 30, 2020, 259 pages (part 1, pp. 1-129).
India Opposition Notice to India Patent Patent Application No. 1328/CHENP/2013 (India Patent No. 319927), filed Jun. 30, 2020, 259 pages (part 2, pp. 130-259).
Indonesia Patent Office, First Examination Report for ID Patent Application No. W00 2010 03923, dated Apr. 5, 2013.
Indonesia Patent Office, First Examination Report for ID Patent Application No. W00 2010 03957, dated Apr. 25, 2013.
Indonesia Patent Office, Substantive Examination Report Stage 1 for ID Application No. W-00201103126, dated Jun. 10, 2014.
Israel Patent Office, First Examination Report for IL Patent Application No. 208515, dated Jan. 6, 2013.
Israel Patent Office, First Examination Report for IL Patent Application No. 208701, dated Jan. 13, 2013.
Israel Patent Office, First Office Action for IL Patent Application No. 214396, dated Jul. 8, 2013.
Israel Patent Office, Notification of Defects for IL Patent Application No. 208515, Aug. 25, 2014.
Israel Patent Office, Notification of Defects for IL Patent Application No. 214396, Nov. 11, 2013.
Israel Patent Office, Notification of Defects for IL Patent Application No. 218599, Aug. 25, 2014.
Israel Patent Office, Notification of Defects for IL Patent Application No. 208701, Aug. 25, 2014.
Israel Patent Office, Notification Prior to Examination for IL Patent Application No. 218599, dated Nov. 13, 2012.
Israel Patent Office, Notification Prior to Examination for IL Patent Application No. 218752, dated Jan. 20, 2014.
Israel Patent Office, Supplement to First Examination Report for IL Patent Application No. 208515, dated Jan. 15, 2013.
Japanese Patent Office, First Examination Report for JP Patent Application No. 2011-506429, dated Aug. 22, 2013.
Japanese Patent Office, First Examination Report for JP Patent Application No. 2011-506435, dated Aug. 22, 2013.
Japanese Patent Office, Response as filed for JP Application No. 2017-520934, 15 pages.
Japanese Patent Office, Notice of Reasons for Rejection for Japanese Patent Appln. No. JP 2017-520934, dated Mar. 30, 2018.
Japanese Patent Office, Notification of Reasons for Rejection for JP Application No. 2011-549324, dated Jul. 28, 2014.
Japanese Patent Office, Notification of Reasons for Rejection for JP Application No. 2011-549324, dated Mar. 26, 2014.
Japanese Patent Office, Notification of Reasons for Rejection for JP Application No. 2012-529958, dated Aug. 5, 2014.
Japanese Patent Office, Notification of Reasons for Rejection for JP Application No. 2012-529963, dated Aug. 28, 2014.
McGuigan, et al., Aryl Phosphoramidate Derivatives of d4T Have Improved Anti-HIV Efficacy in Tissue Culture and May Act by the Generation of a Novel Intracellular Metabolite, J. Med. Chem., 1996, pp. 1748-1753, vol. 39.
Mehellou, et al., Aryloxy Phosphoramidate Triesters: a Technology for Delivering Monophosphorylated Nucleosides and Sugarsinto Cells, ChemMedChem, 2009, pp. 1779-1791, vol. 4.
Mexico Patent Office, English translation of Office Action for MX Application No. MX/a/2013/003179, dated Feb. 25, 2014.
Mexico Patent Office, First Examination Report (in English) for MX Application No. MX/a/2010/011661, dated Oct. 26, 2011.
Mexico Patent Office, Office Action for MX Application No. MX/a/2011/008409, dated Mar. 25, 2014.
Mexico Patent Office, Office Action for MX Application No. MX/a/2013/000656, dated Apr. 22, 2014.
Mexico Patent Office, Response Filed to Office Action for MX application No. MX/a/2013000656, dated Apr. 22, 2014.
Mexico Patent Office, Office Action for MX Application No. MX/a/2013/000656, dated Aug. 4, 2014.
Mexico Patent Office, Office Action for MX Application No. MX/a/2013/000744, dated Apr. 22, 2014.
Mexico Patent Office, Response Filed to the Office Action for MX application No. MX/a/2013000744_07282014, 21 pages.
Mexico Patent Office, Response Filed to the Office Action for MX Application No. MX/a/20100011661, dated Nov. 19, 2014, 5 pages.
Mexico Patent Office, Response Filed to the Office Action for MX Application No. MX/a/2013000656, dated Nov. 19, 2014, 5 pages.

(56) References Cited

OTHER PUBLICATIONS

New Zealand Patent Office, First Examination Report for NZ Patent Application No. 588400, dated Apr. 11, 2011.
New Zealand Patent Office, Response filed for Examination Report for NZ Application No. 588400, dated Jul. 11, 2012, 2 pages.
New Zealand Patent Office, First Examination Report for NZ Patent Application No. 588670, dated Apr. 8, 2011.
New Zealand Patent Office, First Examination Report for NZ Patent Application No. 608070, dated Nov. 7, 2013.
New Zealand Patent Office, Further Examination Report for NZ Application No. 594370, dated Oct. 8, 2013.
New Zealand Patent Office, Second Examination Report and Notice of Acceptance for NZ Patent Application No. 588400, dated Jul. 27, 2012.
Notice of Decision for EG Patent application No. 68/2013, date unknown—Agent's report dated May 17, 2015.
Notification of Formalities Examination Notification of Examination Completed for EA Patent Application No. 201390133, dated Mar. 13, 2013.
Notification of Application Under Consideration for EA Patent Application No. 201390133, dated Mar. 13, 2013.
Notification of Formalities Examination for UA Patent Application No. 201301999, dated Mar. 27, 2013.
Decision Acceptance Form for VN Patent Application No. 1-2012-03889, dated Mar. 27, 2013.
Notification of the Second Office Action for CN Patent Application No. 201180035776.1, dated Oct. 30, 2014 (with English translation).
Office Action issued by the Chilean Patent Office for patent application No. 00076-2013, dated Aug. 31, 2015, 7 pages—First Examination Report with Agent Summary (3 paqes).
Office Action dated Sep. 14, 2012 for U.S. Appl. No. 13/189,373.
Office Action No. 519 for CO Patent Application No. 13 004.205.
Official Action for EA Patent Application No. 201390133, dated Jan. 15, 2015 (and English translation).
Pakistan Notice of Opposition to the Grant of Patent On Pakistan Application No. 684/2015 (Pakistan Patent No. 143378), dated Aug. 5, 2020, 9 pages.
Patil et al., 4-Aza-7,9-Dideazaadenosine, a New Cytotoxic Synthetic C-Nucleoside Analogue of Adenosine, Tetrahedron Letters, 1994, pp. 5339-5342, vol. 35, No. 30.
Peru Patent Office, Office Action in PE Application No. 1464, dated Sep. 12, 2013.
Peterson et al., Prodrug approaches to improving the oral absorption of antiviral nucleotide analogues, Expert Opinion, Drug Deliv., 2009, pp. 405-420, vol. 6, No. 4.
Resolution No. 48031 for CO Patent Application No. 10-121.513, rec'd Oct. 7, 2014 (8 pages) (English translation).
Ross et al., Synthesis of Diastereomerically Pure Nucleotide andPhosphoramidates, J. Org. Chem., 2011,pp. 8311-8319, vol. 76.
Taiwan Cancellation Brief and Exhibits to Taiwan Patent No. 1687432, dated Jul. 17, 2020, 536 pages (part 2, pp. 234-536).
Taiwan Cancellation Brief and Exhibits to Taiwan Patent No. 1687432, dated Jul. 17, 2020, 536 pages (part 1, pp. 1-233).
Taiwan Patent Office, First Examination Report for TW Patent Application No. 098113324, dated Oct. 30, 2012.
Taiwan Patent Office, Office Action with Search Report for TW Patent Application No. 099131868, dated May 22, 2014.
Taiwan Patent Office, Amended Claims filed in response to Office Action for TW Application No. 099131868, dated Oct. 12, 2014, 12 pages.
Taiwan Patent Office, Office Action with Search Report for TW Patent Application No. 102115415, dated May 15, 2014.
Towner et Al., Newly Discovered Ebola Virus Associated with Hemorrhagic Fever Outbreak in Uganda, PLoS Pathogens, 2008, 6 pages, vol. 4, Issue 11.
Ukraine Patent Office, First Examination Report for UA Patent Application No. 2010 13030, dated Mar. 2, 2013.
Ukraine Patent Office, First Office Action for UA Application No. a 2011 10568.
Ukraine Patent Office, Second Office Action for UA Patent Application No. 2011 10568, dated Aug. 11, 2014.
United States Patent and Trademark Office, Final Rejection for U.S. Appl. No. 12/886,248, filed Aug. 21, 2014.
United States Patent and Trademark Office, Notice of Allowance for U.S. Appl. No. 13/649,511, filed Feb. 13, 2014.
United States Patent and Trademark Office, Notice of Allowance for U.S. Appl. No. 13/649,511, filed Jun. 3, 2014.
United States Patent and Trademark Office, Notice of Allowance for U.S. Appl. No. 12/428,176, filed Apr. 12, 2011.
United States Patent and Trademark Office, Notice of Allowance for U.S. Appl. No. 12/428,176, filed Jan. 6, 2011.
United States Patent and Trademark Office, Notice of Allowance for U.S. Appl. No. 12/428,234, filed Apr. 7, 2011.
United States Patent and Trademark Office, Notice of Allowance for U.S. Appl. No. 12/702,957, filed Apr. 26, 2011.
United States Patent and Trademark Office, Notice of Allowance for U.S. Appl. No. 12/885,917, filed Feb. 17, 2011.
United States Patent and Trademark Office, Notice of Allowance for U.S. Appl. No. 13/050,820, filed Jan. 31, 2013.
United States Patent and Trademark Office, Notice of Allowance for U.S. Appl. No. 13/117,060, filed Aug. 10, 2012.
United States Patent and Trademark Office, Notice of Allowance for U.S. Appl. No. 13/117,060, filed Nov. 28, 2012.
United States Patent and Trademark Office, Notice of Allowance for U.S. Appl. No. 13/196,117, filed Jul. 16, 2012.
United States Patent and Trademark Office, Notice of Allowance for U.S. Appl. No. 13/196,117, filed Mar. 27, 2012.
United States Patent and Trademark Office, Office Action (Restriction Requirement) for U.S. Appl. No. 12/886,248, filed Sep. 14, 2012.
United States Patent and Trademark Office, Office Action for U.S. Appl. No. 14/613,719, filed Jul. 21, 2016.
United States Patent and Trademark Office, Office Action for U.S. Appl. No. 14/613,719, filed Nov. 4, 2016.
United States Patent and Trademark Office, Office Action for U.S. Appl. No. 12/428,234, filed Dec. 23, 2010.
United States Patent and Trademark Office, Office Action for U.S. Appl. No. 12/702,957, filed Dec. 23, 2010.
United States Patent and Trademark Office, Office Action for U.S. Appl. No. 12/886,248, filed Mar. 4, 2013.
United States Patent and Trademark Office, Office Action for U.S. Appl. No. 12/886,248, filed Nov. 6, 2012.
United States Patent and Trademark Office, Office Action for U.S. Appl. No. 13/050,820, filed Mar. 27, 2012.
United States Patent and Trademark Office, Office Action for U.S. Appl. No. 13/050,820, filed Oct. 16, 2012.
United States Patent and Trademark Office, Office Action for U.S. Appl. No. 13/196,117, filed Sep. 23, 2011.
United States Patent and Trademark Office, Office Action for U.S. Appl. No. 13/649,511, filed Aug. 15, 2013.
United States Patent and Trademark Office, Office Action for U.S. Appl. No. 13/649,511, filed Jan. 22, 2013.
United States Patent and Trademark Office, Office Action for U.S. Appl. No. 13/813,886, filed Sep. 24, 2014.
United States Patent and Trademark Office, Pre-Appeal Brief for U.S. Appl. No. 14/613,719, filed Feb. 6, 2017.
United States Patent and Trademark Office, Pre-Appeal Decision for U.S. Appl. No. 14/613,719, filed Mar. 14, 2017.
Vietnam Patent Office, First Examination Report for VN Patent Application No. 1-2010-02653, dated Apr. 26, 2012.
Vietnam Patent Office, First Examination Report for VN Patent Application No. 1-2010-02939, dated Apr. 19, 2012.
Vietnam Patent Office, First Office Action for VN Patent Application No. 1-2012-03895, dated Feb. 8, 2013.
Vietnam Patent Office, Second Examination Report for VN Patent Application No. 1-2010-02939, dated Jul. 26, 2012.
Adlington et al., "Synthesis of novel C-nucleosides with potential applications in combination and parallel synthesis," Tetrahedron Letters, 2000, 41:575-578.
Huang et al., "Recent development of therapeutics for chronic HCV infection," Antiviral Research, Sep. 2006, 71(2-3): 351-362.

(56) References Cited

OTHER PUBLICATIONS

Kushner et al., "Pharmacological uses and perspectives of heavy water and deuterated compounds," Canadian Journal of Physiology and Pharmacology, Feb. 1999, 77(2):79-88.
Martin et al., "Hint2, A Mitochondrial Apoptotic Sensitizer Down-Regulated in Hepatocellular Carcinoma," Gastroenterology, Jun. 2006, 130(7):2179-2188.
Shi et al., "Synthesis and anti-viral activity of a series of d- and 1-2'-deoxy-2'-fluororibonucleosides in the subgenomic HCV replicon system," Bioorganic & Medicinal Chemistry, Mar. 2005, 13(5):1641-1652.
Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19):7202-7218.
Stein et al., "Phosphorylation of Nucleoside Analog Antiretrovirals: A Review for Clinicians," Pharmacotherapy, Jan. 2001, 21(1):11-34.
Stella et al., "Cyclodextrins," Toxicologic Pathology, 2008, 36(1):30-42.
Peruvian Office Action in PE Patent Application No. 001124-2017/DIN, dated Jan. 28, 2022, 24 pages (with English translation).
U.S. Appl. No. 17/333,389, filed May 28, 2021, Thomas Cihlar.
U.S. Appl. No. 17/676,920, filed Feb. 22, 2022, Thomas Cihlar.
U.S. Appl. No. 17/222,125, filed Apr. 5, 2021, Scott Ellis.
U.S. Appl. No. 17/158,391, filed Jan. 26, 2021, Cihlar.
U.S. Appl. No. 17/198,829, filed Mar. 11, 2021, Pavel R. Badalov.
U.S. Appl. No. 16/031,620, filed Jul. 10, 2018, Nate Larson.
U.S. Appl. No. 16/865209, filed May 1, 2020, Nate Larson.
U.S. Appl. No. 17/585,651, filed Jan. 27, 2022, Nate Larson.
U.S. Appl. No. 15/919,750, filed Mar. 13, 2018, Michel Joseph Perron.
U.S. Appl. No. 16/852,102, filed Apr. 17, 2020, Michel Joseph Perron.
U.S. Appl. No. 17/578,682, filed Jan. 19, 2022, Michel Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 15/267,433, filed Sep. 16, 2016, Michael O'Neil Hanrahan Clarke.
U.S. Appl. No. 16/265,016, filed Feb. 1, 2019, Michael O'Neil Hanrahan Clarke.
U.S. Appl. No. 16/863,566, filed Apr. 30, 2020, Michael O'Neil Hanrahan Clarke.
U.S. Appl. No. 17/222,066, filed Apr. 5, 2021, Michael O'Neil Hanrahan Clarke.
U.S. Appl. No. 17/748,400, filed May 19, 2022, Michael O'Neil Hanrahan Clarke.
U.S. Appl. No. 14/926,063, filed Oct. 29, 2015, Steven Donald Axt.
U.S. Appl. No. 16/692,966, filed Nov. 22, 2019, Steven Axt.
U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 15/579,650, filed Jan. 20, 2022, Byoung Kwon Chun.
U.S. Appl. No. 13/813,886, filed Jun. 25, 2013, Aesop Cho.
U.S. Appl. No. 14/746,430, filed Jun. 22, 2015, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 12/248,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 17/458,023, filed Aug. 26, 2021, Byoung-Kwon Chun.
U.S. Appl. No. 17/355,813, filed Jun. 23, 2021, Daniel H. Byun.

* cited by examiner

METHODS AND COMPOUNDS FOR TREATING *PARAMYXOVIRIDAE* VIRUS INFECTIONS

CROSS-REFERENCE TO RELATED APPLICATIONS

This Application is a Continuation of U.S. patent application Ser. No. 16/042,085, filed on Jul. 23, 2018, which is a Divisional of U.S. patent application Ser. No. 14/613,719, filed on Feb. 4, 2015, now U.S. Pat. No. 10,065,958, issued on Sep. 4, 2018, which is a Continuation of U.S. patent application Ser. No. 13/189,373, filed on Jul. 22, 2011, which claims the benefit of U.S. Provisional Application 61/366,609 filed on Jul. 22, 2010.

FIELD OF THE INVENTION

The invention relates generally to methods and compounds for treating Paramyxoviridae virus infections, particularly methods and nucleosides for treating respiratory syncytial virus infections and parainfluenza virus infections.

BACKGROUND OF THE INVENTION

Paramyxoviruses of the Paramyxoviridae family are negative-sense, single-stranded, RNA viruses that are responsible for many prevalent human and animal diseases. These viruses comprise at least two major subfamilies, Paramyxovirinae and Pneumovirinae. The subfamily Paramyxovirina includes the human parainfluenza viruses (HPIV), measles virus and mumps virus. Although, vaccines are available to prevent measles and mumps infections, these infections caused 745, 00 deaths in 2001 so additional treatments would be desirable for susceptible populations. HPIV are the second most common cause of lower respiratory tract infection in younger children and collectively cause about 75% of the cases of Croup (http://www.cdc.gov/ncidod/dvrd/revb/respiratory/hpivfeat.htm). HPIVs can cause repeated infections throughout life including upper respiratory tract illness and even serious lower respiratory tract disease (e.g., pneumonia, bronchitis, and bronchiolitis), the latter being especially of concern among the elderly, and among patients with compromised immune systems (Sable, *Infect. Dis. Clin. North Am.* 1995, 9, 987-1003). Currently, no vaccines are available to prevent HPIV infections. Therefore there is a need for anti-Paramyxovirina therapeutics.

The subfamily Pneumovirinae includes Human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (http://www.cdc.gov/rsv/index.html). No vaccine to prevent HRSV infection is currently available. The monoclonal antibody palivizumab is available for infants at high risk, e.g., premature infants or those with either cardiac or lung disease, but the cost for general use is often prohibitive. Ribavirin has also been used to treat HRSV infections but has limited efficacy. Therefore, there is a need for anti-Pneumovirinae therapeutics and anti-Paramyxoviridae therapeutics in general.

Ribosides of the nucleobases pyrrolo[1,2-f][1,2,4]triazine, imidazo[1,5-f][1,2,4]triazine, imidazo[1,2-f][1,2,4]triazine, and [1,2,4]triazolo[4,3-f][1,2,4]triazine have been disclosed in *Carbohydrate Research* 2001, 331(1), 77-82; *Nucleosides & Nucleotides* (1996), 15(1-3), 793-807; *Tetrahedron Letters* (1994), 35(30), 5339-42; *Heterocycles* (1992), 34(3), 569-74; *J. Chem. Soc. Perkin Trans.* 1 1985, 3, 621-30; *J. Chem. Soc. Perkin Trans.* 1 1984, 2, 229-38; WO 2000056734; *Organic Letters* (2001), 3(6), 839-842; *J. Chem. Soc. Perkin Trans.* 1 1999, 20, 2929-2936; and *J. Med. Chem.* 1986, 29(11), 2231-5. Ribosides of pyrrolo[1,2-f][1,2,4]triazine nucleobases with antiviral, anti-HCV, and anti-RdRp activity have been disclosed by Babu (WO2008/089105 and WO2008/141079) and Francom (WO2010/002877).

Butler, et al., WO2009132135, disclose 1' substituted ribosides and prodrugs comprising pyrrolo[1,2-f][1,2,4]triazine nucleobases which have anti-HCV and anti-RdRp activity. However, no methods of treating Paramyxoviridae infections with these compounds have been disclosed.

SUMMARY OF THE INVENTION

Provided are methods and compounds for the treatment of infections cased by the Paramyxoviridae virus family.

Provided, is a method for treating a Paramyxoviridae infection in a mammal in need thereof comprising administering a therapeutically effective amount of a compound of Formula I:

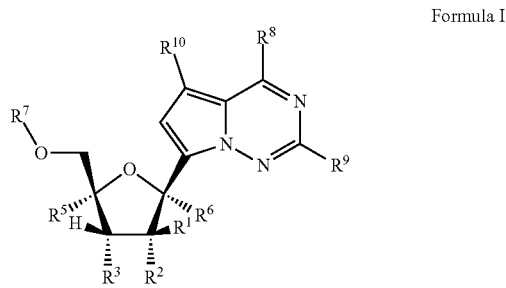

Formula I or a pharmaceutically acceptable salt or ester, thereof;
wherein:
each $R^1$ is H or halogen;
each $R^2$, $R^3$ or $R^5$ is independently H, $OR^a$, $N(R^a)_2$, $N_3$, CN, $NO_2$, $S(O)_nR^a$, halogen, $(C_1-C_8)$alkyl, $(C_4-C_8)$carbocyclylalkyl, $(C_1-C_8)$ substituted alkyl, $(C_2-C_8)$alkenyl, $(C_2-C_8)$ substituted alkenyl, $(C_2-C_8)$alkynyl or $(C_2-C_8)$ substituted alkynyl;
or any two $R^2$, $R^3$ or $R^5$ on adjacent carbon atoms when taken together are —O(CO)O— or when taken together with the ring carbon atoms to which they are attached form a double bond;
$R^6$ is $OR^a$, $N(R^a)_2$, $N_3$, CN, $NO_2$, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)(O$R^{11}$), —S(O)$_2$(O$R^{11}$), —SO$_2NR^{11}R^{12}$, halogen, $(C_1-C_8)$alkyl, $(C_4-C_8)$carbocyclylalkyl, $(C_1-C_8)$ substituted alkyl, $(C_2-C_8)$alkenyl, $(C_2-C_8)$ substituted alkenyl, $(C_2-C_8)$alkynyl, $(C_2-C_8)$ substituted alkynyl, or aryl$(C_1-C_8)$alkyl;
each n is independently 0, 1, or 2;
each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$carbocyclylalkyl, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)(O$R^{11}$), —S(O)$_2$(O$R^{11}$), or —SO$_2NR^{11}R^{12}$;

$R^7$ is H, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), —SO$_2$N$R^{11}R^{12}$, or

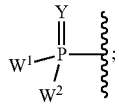

each Y or $Y^1$ is, independently, O, S, NR, $^+$N(O)(R), N(OR), $^+$N(O)(OR), or N—NR$_2$;

$W^1$ and $W^2$, when taken together, are —$Y^3$(C($R^y$)$_2$)$_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of the Formula Ia:

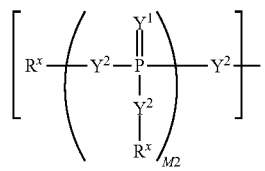

Formula Ia wherein:

each $Y^2$ is independently a bond, O, CR$_2$, NR, $^+$N(O)(R), N(OR), $^+$N(O)(OR), N—NR$_2$, S, S—S, S(O), or S(O)$_2$;

each $Y^3$ is independently O, S, or NR;

M2 is 0, 1 or 2;

each $R^x$ is independently $R^y$ or the formula:

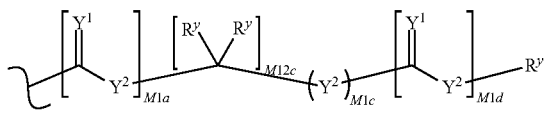

wherein:

each M1a, M1c, and M1d is independently 0 or 1;

M12c is 0, 1, 2, 3, 4, 5, 6, 7, 8, 9, 10, 11 or 12;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, SO$_2$NR$_2$, —CN, —N$_3$, —NO$_2$, —OR, or $W^3$; or when taken together, two $R^y$ on the same carbon atom form a carbocyclic ring of 3 to 7 carbon atoms;

each R is independently H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, C$_2$-C$_{20}$ heterocyclyl, C$_2$-C$_{20}$ substituted heterocyclyl, arylalkyl or substituted arylalkyl;

$W^3$ is $W^4$ or $W^5$; $W^4$ is R, —C($Y^1$)$R^y$, —C($Y^1$)$W^5$, —SO$_2R^y$, or —SO$_2W^5$; and $W^5$ is a carbocycle or a heterocycle wherein $W^5$ is independently substituted with 0 to 3 $R^y$ groups;

each $R^8$ is halogen, N$R^{11}R^{12}$, N($R^{11}$)O$R^{11}$, N$R^{11}$N$R^{11}R^{12}$, N$_3$, NO, NO$_2$, CHO, CN, —CH(=N$R^{11}$), —CH=NNH$R^{11}$, —CH=N(O$R^{11}$), —CH(O$R^{11}$)$_2$, —C(=O)N$R^{11}R^{12}$, —C(=S)N$R^{11}R^{12}$, —C(=O)O$R^{11}$, (C$_1$-C$_8$)alkyl, (C$_2$-C$_8$)alkenyl, (C$_2$-C$_8$)alkynyl, (C$_4$-C$_8$)carbocyclylalkyl, optionally substituted aryl, optionally substituted heteroaryl, —C(=O)(C$_1$-C$_8$)alkyl, —S(O)$_n$(C$_1$-C$_8$)alkyl, aryl(C$_1$-C$_8$)alkyl, O$R^{11}$ or S$R^{11}$;

each $R^9$ or $R^{10}$ is independently H, halogen, N$R^{11}R^{12}$, N($R^{11}$)O$R^{11}$, N$R^{11}$N$R^{11}R^{12}$, N$_3$, NO, NO$_2$, CHO, CN, —CH(=N$R^{11}$), —CH=NHN$R^{11}$, —CH=N(O$R^{11}$), —CH(O$R^{11}$)$_2$, —C(=O)N$R^{11}R^{12}$, —C(=S)N$R^{11}R^{12}$, —C(=O)O$R^{11}$, $R^{11}$, O$R^{11}$ or S$R^{11}$;

each $R^{11}$ or $R^{12}$ is independently H, (C$_1$-C$_8$)alkyl, (C$_2$-C$_8$)alkenyl, (C$_2$-C$_8$)alkynyl, (C$_4$-C$_8$)carbocyclylalkyl, optionally substituted aryl, optionally substituted heteroaryl, —C(=O)(C$_1$-C$_8$)alkyl, —S(O)$_n$(C$_1$-C$_8$)alkyl or aryl(C$_1$-C$_8$)alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —N$R^a$—; and wherein each (C$_1$-C$_8$)alkyl, (C$_2$-C$_8$)alkenyl, (C$_2$-C$_8$)alkynyl or aryl(C$_1$-C$_8$)alkyl of each $R^2$, $R^3$, $R^5$, $R^6$, $R^{11}$ or $R^{12}$ is, independently, optionally substituted with one or more halo, hydroxy, CN, N$_3$, N($R^a$)$_2$ or O$R^a$; and wherein one or more of the non-terminal carbon atoms of each said (C$_1$-C$_8$)alkyl may be optionally replaced with —O—, —S— or —N$R^a$—.

In another embodiment, the method comprises administering a therapeutically effective amount of a racemate, enantiomer, diastereomer, tautomer, polymorph, pseudopolymorph, amorphous form, hydrate or solvate of a compound of Formula I or a pharmaceutically acceptable salt or ester thereof to a mammal in need thereof.

In another embodiment, the method comprises treating a Paramyxovirina infection in a mammal in need thereof by administering a therapeutically effective amount of a compound of Formula I or a pharmaceutically acceptable salt or ester thereof.

In another embodiment, the method comprises treating a parainfluenza, measles or mumps virus infection in a mammal in need thereof by administering a therapeutically effective amount of a compound of Formula I or a pharmaceutically acceptable salt or ester thereof.

In another embodiment, the method comprises treating a parainfluenza virus infection in a mammal in need thereof by administering a therapeutically effective amount of a compound of Formula I or a pharmaceutically acceptable salt or ester thereof.

In another embodiment, the method comprises treating a Pneumovirinae infection in a mammal in need thereof by administering a therapeutically effective amount of a compound of Formula I or a pharmaceutically acceptable salt or ester thereof.

In another embodiment, the method comprises treating a respiratory syncytial virus infection in a mammal in need thereof by administering a therapeutically effective amount of a compound of Formula I or a pharmaceutically acceptable salt or ester thereof.

In another embodiment, the method comprises administering a therapeutically effective amount of a pharmaceutical composition comprising an effective amount of a Formula I compound, or a pharmaceutically acceptable salt or ester thereof, in combination with a pharmaceutically acceptable diluent or carrier.

In another embodiment, the method comprises administering a therapeutically effective amount of a pharmaceutical composition comprising an effective amount of a Formula I compound, or a pharmaceutically acceptable salt or ester thereof, in combination with at least one additional therapeutic agent.

In another embodiment, the method comprises administering a therapeutically effective amount of a combination pharmaceutical agent comprising:

a) a first pharmaceutical composition comprising a compound of Formula I; or a pharmaceutically acceptable salt, solvate, or ester thereof; and b) a second pharmaceutical composition comprising at least one additional therapeutic agent active against infectious Paramyxoviridae viruses.

In another embodiment, the present application provides for a method of inhibiting a Paramyxoviridae RNA-dependent RNA polymerase, comprising contacting a cell infected with a Paramyxoviridae virus with an effective amount of a compound of Formula I; or a pharmaceutically acceptable salts, solvate, and/or ester thereof.

In another embodiment, provided is the use of a compound of Formula I or a pharmaceutically acceptable salt, solvate, and/or ester thereof to treat a viral infection caused by a Paramyxoviridae virus.

In another aspect, the invention also provides processes and novel intermediates disclosed herein which are useful for preparing Formula I compounds of the invention.

In other aspects, novel methods for synthesis, analysis, separation, isolation, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

In another embodiment, provided is a method of treating a Paramyxoviridae infection in a mammal in need thereof comprising administering a therapeutically effective amount of a compound of Formula I represented by Formula II:

Formula II or a pharmaceutically acceptable salt or ester, thereof; wherein:

each $R^1$ is H or halogen;

each $R^2$ is $OR^a$ or halogen;

each $R^3$ or $R^5$ is independently H, $OR^a$, $N(R^a)_2$, $N_3$, CN, $NO_2$, $S(O)_nR^a$, halogen, $(C_1\text{-}C_8)$alkyl, $(C_4\text{-}C_8)$carbocyclylalkyl, $(C_1\text{-}C_8)$ substituted alkyl, $(C_2\text{-}C_8)$alkenyl, $(C_2\text{-}C_8)$ substituted alkenyl, $(C_2\text{-}C_8)$alkynyl or $(C_2\text{-}C_8)$ substituted alkynyl;

or any two $R^2$, $R^3$ or $R^5$ on adjacent carbon atoms when taken together are —O(CO)O— or when taken together with the ring carbon atoms to which they are attached form a double bond;

$R^6$ is $OR^a$, $N(R^a)_2$, $N_3$, CN, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, halogen, $(C_1\text{-}C_8)$alkyl, $(C_4\text{-}C_8)$carbocyclylalkyl, $(C_1\text{-}C_8)$ substituted alkyl, $(C_2\text{-}C_8)$alkenyl, $(C_2\text{-}C_8)$ substituted alkenyl, $(C_2\text{-}C_8)$alkynyl, or $(C_2\text{-}C_8)$ substituted alkynyl;

each n is independently 0, 1, or 2;

each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), or —SO$_2NR^{11}R^{12}$;

$R^7$ is H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2$($OR^{11}$), —SO$_2NR^{11}R^{12}$, or each Y or $Y^1$ is, independently, O, S, NR, $^+$N(O)(R), N(OR), $^+$N(O)(OR), or N—NR$_2$;

$W^1$ and $W^2$, when taken together, are —$Y^3$(C($R^y$)$_2$)$_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of the Formula Ia:

Formula Ia wherein:

each $Y^2$ is independently a bond, O, $CR_2$, NR, $^+$N(O)(R), N(OR), $^+$N(O)(OR), N—NR$_2$, S, S—S, S(O), or S(O)$_2$;

each $Y^3$ is independently O, S, or NR;

M2 is 0, 1 or 2;

each $R^x$ is independently $R^y$ or the formula:

wherein:

each M1a, M1c, and M1d is independently 0 or 1;

M12c is 0, 1, 2, 3, 4, 5, 6, 7, 8, 9, 10, 11 or 12;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC $(=Y^1)(N(R)_2)$, $-N(R)C(=Y^1)R$, $-N(R)C(=Y^1)OR$, $-N(R)C(=Y^1)N(R)_2$, $-SO_2NR_2$, $-CN$, $-N_3$, $-NO_2$, $-OR$, or $W^3$; or when taken together, two $R^y$ on the same carbon atom form a carbocyclic ring of 3 to 7 carbon atoms;

each R is independently H, $(C_1-C_8)$ alkyl, $(C_1-C_8)$ substituted alkyl, $(C_2-C_8)$alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, arylalkyl or substituted arylalkyl;

$W^3$ is $W^4$ or $W^5$; $W^4$ is R, $-C(Y^1)R^y$, $-C(Y^1)W^5$, $-SO_2R^y$, or $-SO_2W^5$; and $W^5$ is a carbocycle or a heterocycle wherein $W^5$ is independently substituted with 0 to 3 $R^y$ groups;

each $R^8$ is halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NNHR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, $-C(=O)(C_1-C_8)$alkyl, $-S(O)_n(C_1-C_8)$alkyl, aryl$(C_1-C_8)$alkyl, $OR^{11}$ or $SR^{11}$;

each $R^9$ is independently H, halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NNHR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $R^{11}$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, $-C(=O)(C_1-C_8)$alkyl, $-S(O)_n(C_1-C_8)$alkyl or aryl$(C_1-C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S-$ or $-NR^a-$; and wherein each $(C_1-C_8)$alkyl, $(C_2-C_8)$alkenyl, $(C_2-C_8)$alkynyl or aryl$(C_1-C_8)$alkyl of each $R^3$, $R^5$, $R^6$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1-C_8)$alkyl may be optionally replaced with $-O-$, $-S-$ or $-NR^a-$.

In one embodiment of the method of treating a Paramyxoviridae infection by administering a compound of Formula II, $R^1$ of Formula II is H. In another aspect of this embodiment $R^6$ of Formula II is $N_3$, CN, halogen, $(C_1-C_8)$alkyl, $(C_1-C_8)$ substituted alkyl, $(C_2-C_8)$alkenyl, $(C_2-C_8)$ substituted alkenyl, $(C_2-C_8)$alkynyl, or $(C_2-C_8)$ substituted alkynyl. In another aspect of this embodiment, $R^6$ of Formula II is CN, methyl, ethenyl, or ethynyl. In another aspect of this embodiment, $R^6$ of Formula II is CN. In another aspect of this embodiment, $R^6$ of Formula II is methyl. In another aspect of this embodiment, $R^5$ of Formula II is H. In another aspect of this embodiment, $R^2$ of Formula II is $OR^a$. In another aspect of this embodiment, $R^2$ of Formula II is OH. In another aspect of this embodiment, $R^2$ of Formula II is F. In another aspect of this embodiment, $R^3$ of Formula II is $OR^a$. In another aspect of this embodiment, $R^3$ of Formula II is OH, $-OC(=O)R^{11}$, or $-OC(=O)OR^{11}$. In another aspect of this embodiment, $R^3$ of Formula II is OH. In another aspect of this embodiment, $R^8$ of Formula II is $NR^{11}R^{12}$. In another aspect of this embodiment, $R^8$ of Formula II is $NH_2$. In another aspect of this embodiment, $R^8$ of Formula II is $OR^{11}$. In another aspect of this embodiment, $R^8$ of Formula II is OH. In another aspect of this embodiment, $R^9$ of Formula II is H. In another aspect of this embodiment, $R^9$ of Formula II is $NR^{11}R^{12}$. In another aspect of this embodiment, $R^9$ of Formula II is $NH_2$. In another aspect of this embodiment, $R^7$ of Formula II is H, $-C(=O)R^{11}$, $-C(=O)OR^{11}$ or

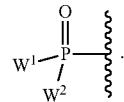

In another aspect of this embodiment, $R^7$ of Formula II is H. In another aspect of this embodiment, $R^7$ of Formula II is

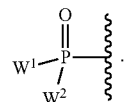

In another embodiment of the method of treating a Paramyxoviridae infection comprising administering a compound of Formula II, the Paramyxoviridae infection is caused by a Paramyxovirina virus. In another aspect of this embodiment, the Paramyxovirina virus is a parainfluenza, measles or mumps virus. In another aspect of this embodiment, the Paramyxovirina virus is a Respirovirus virus. In another aspect of this embodiment, the Paramyxovirina virus is a type 1 or 3 Human parainfluenza virus.

In another embodiment of the method of treating a Paramyxoviridae infection comprising administering a compound of Formula II, the Paramyxoviridae infection is caused by a Pneumovirinae virus. In another aspect of this embodiment, the Pneumovirinae virus is a respiratory syncytial virus. In another aspect of this embodiment, the Pneumovirinae virus is a Human respiratory syncytial virus.

In another embodiment, provided is a method of treating a Paramyxoviridae infection in a mammal in need thereof comprising administering a therapeutically effective amount of a compound of Formula I represented by Formula III:

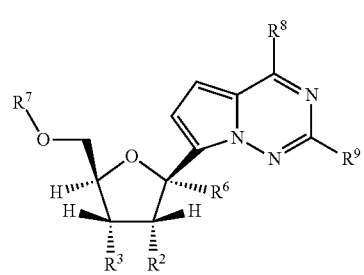

Formula III or a pharmaceutically acceptable salt or ester, thereof; wherein:

each $R^2$ is $OR^a$ or F;
each $R^3$ is $OR^a$;
$R^6$ is $OR^a$, $N(R^a)_2$, $N_3$, CN, $S(O)_nR^a$, $-C(=O)R^{11}$, $-C(=O)OR^{11}$, $-C(=O)NR^{11}R^{12}$, $-C(=O)SR^{11}$, $-S(O)R^{11}$, $-S(O)_2R^{11}$, $-S(O)(OR^{11})$, $-S(O)_2(OR^{11})$, $-SO_2NR^{11}R^{12}$, halogen, $(C_1-C_8)$alkyl, $(C_4-C_8)$carbocyclylalkyl, $(C_1-C_8)$ substituted alkyl, $(C_2-C_8)$alkenyl, $(C_2-C_8)$ substituted alkenyl, $(C_2-C_8)$alkynyl, or $(C_2-C_8)$ substituted alkynyl;
each n is independently 0, 1, or 2;

each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$carbocyclylalkyl, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), or —SO$_2$N$R^{11}R^{12}$;

$R^7$ is H, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), SO$_2$N$R^{11}R^{12}$, or $$W^1 \!\!-\!\!\overset{\overset{Y}{\|}}{\underset{W^2}{P}}\!\!-$$

each Y or $Y^1$ is, independently, O, S, NR, $^+$N(O)(R), N(OR), $^+$N(O)(OR), or N—NR$_2$;

$W^1$ and $W^2$, when taken together, are —$Y^3$(C(R$^y$)$_2$)$_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of the Formula Ia:

$$\left[R^x\!\!-\!\!\left(\!\!-\!\!Y^2\!-\!\!\overset{\overset{Y^1}{\|}}{\underset{\underset{R^x}{Y^2}}{\underset{|}{P}}}\!\!-\!\!Y^2\!\!-\!\!\right)\!\!\right]_{M2}$$ Formula Ia wherein:

each $Y^2$ is independently a bond, O, CR$_2$, NR, $^+$N(O)(R), N(OR), $^+$N(O)(OR), N—NR$_2$, S, S—S, S(O), or S(O)$_2$;

each $Y^3$ is independently O, S, or NR;

M2 is 0, 1 or 2;

each $R^x$ is independently $R^y$ or the formula:

$$\text{-}\!\!\left(\!\!-\!\!\overset{\overset{Y^1}{\|}}{\underset{}{C}}\!\!-\!\!Y^2\!\!-\!\!\right)_{M1a}\!\!\left(\!\!-\!\!\overset{R^y}{\underset{\underset{R^y}{|}}{C}}\!\!-\!\!\right)_{M12c}\!\!\left(\!\!-\!\!Y^2\!\!-\!\!\right)_{M1c}\!\!\left(\!\!-\!\!\overset{\overset{Y^1}{\|}}{\underset{}{C}}\!\!-\!\!Y^2\!\!-\!\!\right)_{M1d}\!\!R^y$$

wherein:

each M1a, M1c, and M1d is independently 0 or 1;

M12c is 0, 1, 2, 3, 4, 5, 6, 7, 8, 9, 10, 11 or 12;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —SO$_2$NR$_2$, —CN, —N$_3$, —NO$_2$, —OR, or $W^3$; or when taken together, two $R^y$ on the same carbon atom form a carbocyclic ring of 3 to 7 carbon atoms;

each R is independently H, $(C_1-C_8)$ alkyl, $(C_1-C_8)$ substituted alkyl, $(C_2-C_8)$alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, arylalkyl or substituted arylalkyl;

$W^3$ is $W^4$ or $W^5$; $W^4$ is R, —C($Y^1$)R$^y$, —C($Y^1$)$W^5$, —SO$_2$R$^y$, or —SO$_2W^5$; and $W^5$ is a carbocycle or a heterocycle wherein $W^5$ is independently substituted with 0 to 3 R$^y$ groups;

each $R^8$ is halogen, N$R^{11}R^{12}$, N($R^{11}$)O$R^{11}$, N$R^{11}$N$R^{11}R^{12}$, N$_3$, NO, NO$_2$, CHO, CN, —CH(=N$R^{11}$), —CH=NNH$R^{11}$, —CH=N(O$R^{11}$), —CH(O$R^{11}$)$_2$, —C(=O)N$R^{11}R^{12}$, —C(=S)N$R^{11}R^{12}$, —C(=O)O$R^{11}$, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)($C_1-C_8$)alkyl, —S(O)$_n$($C_1-C_8$)alkyl, aryl($C_1-C_8$)alkyl, O$R^{11}$ or S$R^{11}$;

each $R^9$ is independently H, halogen, N$R^{11}R^{12}$, N($R^{11}$)O$R^{11}$, N$R^{11}$N$R^{11}R^{12}$, N$_3$, NO, NO$_2$, CHO, CN, —CH(=N$R^{11}$), —CH=NHN$R^{11}$, —CH=N(O$R^{11}$), —CH(O$R^{11}$)$_2$, —C(=O)N$R^{11}R^{12}$, —C(=S)N$R^{11}R^{12}$, —C(=O)O$R^{11}$, $R^{11}$, O$R^{11}$ or S$R^{11}$; and each $R^{11}$ or $R^{12}$ is independently H, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)($C_1-C_8$)alkyl, —S(O)$_n$($C_1-C_8$)alkyl or aryl($C_1-C_8$)alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —N$R^a$—; and wherein each $(C_1-C_8)$alkyl, $(C_2-C_8)$alkenyl, $(C_2-C_8)$alkynyl or aryl($C_1-C_8$)alkyl of each $R^6$, $R^{11}$ or $R^{12}$ is, independently, optionally substituted with one or more halo, hydroxy, CN, N$_3$, N($R^a$)$_2$ or O$R^a$; and wherein one or more of the non-terminal carbon atoms of each said $(C_1-C_8)$alkyl may be optionally replaced with —O—, —S— or —N$R^a$—.

In one embodiment of the method of treating a Paramyxoviridae infection comprising administering a compound of Formula III, $R^6$ of Formula III is N$_3$, CN, halogen, $(C_1-C_8)$ alkyl, $(C_1-C_8)$ substituted alkyl, $(C_2-C_8)$alkenyl, $(C_2-C_8)$ substituted alkenyl, $(C_2-C_8)$alkynyl, or $(C_2-C_8)$ substituted alkynyl. In another aspect of this embodiment, $R^6$ of Formula III is CN, methyl, ethenyl, or ethynyl. In another aspect of this embodiment, $R^6$ of Formula III is CN. In another aspect of this embodiment, $R^6$ of Formula III is methyl. In another aspect of this embodiment, $R^2$ of Formula III is O$R^a$. In another aspect of this embodiment, $R^2$ of Formula III is OH. In another aspect of this embodiment, $R^2$ of Formula III is F. In another aspect of this embodiment, $R^3$ of Formula III is OH, —OC(=O)$R^{11}$, or —OC(=O)O$R^{11}$. In another aspect of this embodiment, $R^3$ of Formula III is OH. In another aspect of this embodiment, $R^8$ of Formula III is N$R^{11}R^{12}$. In another aspect of this embodiment, $R^8$ of Formula III is NH$_2$. In another aspect of this embodiment, $R^8$ of Formula III is O$R^{11}$. In another aspect of this embodiment, $R^8$ of Formula III is OH. In another aspect of this embodiment, $R^9$ of Formula III is H. In another aspect of this embodiment, $R^9$ of Formula III is N$R^{11}R^{12}$. In another aspect of this embodiment, $R^9$ of Formula III is NH$_2$. In another aspect of this embodiment, $R^7$ of Formula III is H, —C(=O)$R^{11}$, —C(=O)O$R^{11}$ or $$W^1\!\!-\!\!\overset{\overset{O}{\|}}{\underset{W^2}{P}}\!\!-.$$

In another aspect of this embodiment, $R^7$ of Formula III is H. In another aspect of this embodiment, $R^7$ of Formula III is $$W^1-\overset{\overset{O}{\|}}{\underset{W^2}{P}}-\xi$$

In another embodiment of the method of treating a Paramyxoviridae infection comprising administering a compound of Formula III, $R^6$ of Formula III is $N_3$, CN, halogen, $(C_1\text{-}C_8)$alkyl, $(C_1\text{-}C_8)$ substituted alkyl, $(C_2\text{-}C_8)$alkenyl, $(C_2\text{-}C_8)$ substituted alkenyl, $(C_2\text{-}C_8)$alkynyl, or $(C_2\text{-}C_8)$ substituted alkynyl and $R^8$ is $NH_2$. In another aspect of this embodiment, $R^6$ of Formula III is CN, methyl, ethenyl, or ethynyl. In another aspect of this embodiment, $R^6$ of Formula III is CN. In another aspect of this embodiment, $R^6$ of Formula III is methyl. In another aspect of this embodiment, $R^2$ of Formula III is $OR^a$. In another aspect of this embodiment, $R^2$ of Formula III is OH, $-OC(=O)R^{11}$, or $-OC(=O)OR^{11}$. In another aspect of this embodiment, $R^2$ of Formula III is OH. In another aspect of this embodiment, $R^2$ of Formula III is F. In another aspect of this embodiment, $R^3$ of Formula III is OH, $-OC(=O)R^{11}$, or $-OC(=O)OR^{11}$. In another aspect of this embodiment, $R^3$ of Formula III is OH. In another aspect of this embodiment, $R^9$ of Formula III is H. In another aspect of this embodiment, $R^9$ of Formula III is $NR^{11}R^{12}$. In another aspect of this embodiment, $R^9$ of Formula III is $NH_2$. In another aspect of this embodiment, $R^7$ of Formula III is H, $-C(=O)R^{11}$, $-C(=O)OR^{11}$ or $$W^1-\overset{\overset{O}{\|}}{\underset{W^2}{P}}-\xi$$

In another aspect of this embodiment, $R^7$ of Formula III is H. In another aspect of this embodiment, $R^7$ of Formula III is $$W^1-\overset{\overset{O}{\|}}{\underset{W^2}{P}}-\xi$$

In another embodiment of the method of treating a Paramyxoviridae infection comprising administering a compound of Formula III, $R^6$ of Formula III is CN, methyl, ethenyl, or ethynyl, $R^8$ is $NH_2$, and $R^9$ is H. In another aspect of this embodiment, $R^6$ of Formula III is CN. In another aspect of this embodiment, $R^6$ of Formula III is methyl. In another aspect of this embodiment, $R^2$ of Formula III is $OR^a$. In another aspect of this embodiment, $R^2$ of Formula III is OH, $-OC(=O)R^{11}$, or $-OC(=O)OR^{11}$. In another aspect of this embodiment, $R^2$ of Formula III is OH. In another aspect of this embodiment, $R^2$ of Formula III is F. In another aspect of this embodiment, $R^3$ of Formula III is OH, $-OC(=O)R^{11}$, or $-OC(=O)OR^{11}$. In another aspect of this embodiment, $R^3$ of Formula III is OH. In another aspect of this embodiment, $R^7$ of Formula III is H, $-C(=O)R^{11}$, $-C(=O)OR^{11}$ or $$W^1-\overset{\overset{O}{\|}}{\underset{W^2}{P}}-\xi$$

In another aspect of this embodiment, $R^7$ of Formula III is H. In another aspect of this embodiment, $R^7$ of Formula III is $$W^1-\overset{\overset{O}{\|}}{\underset{W^2}{P}}-\xi$$

In another embodiment of the method of treating a Paramyxoviridae infection comprising administering a compound of Formula III, the Paramyxoviridae infection is caused by a Paramyxovirina virus. In another aspect of this embodiment, the Paramyxovirina virus is a parainfluenza, measles or mumps virus. In another aspect of this embodiment, the Paramyxovirina virus is a Respirovirus virus. In another aspect of this embodiment, the Paramyxovirina virus is a type 1 or 3 Human parainfluenza virus.

In another embodiment of the method of treating a Paramyxoviridae infection comprising administering a compound of Formula III, the Paramyxoviridae infection is caused by a Pneumovirinae virus. In another aspect of this embodiment, the Pneumovirinae virus is a respiratory syncytial virus. In another aspect of this embodiment, the Pneumovirinae virus is a Human respiratory syncytial virus.

In one embodiment, provided is a compound of Formula IV:

Formula IV

[Structure of Formula IV showing a pyrrolo[2,1-f][1,2,4]triazine substituted furanose, with substituents $R^1$, $R^3$, $R^5$, $R^6$, $R^7$, $R^8$, $R^9$, and F on the sugar ring]

or a pharmaceutically acceptable salt or ester, thereof;
wherein:
each $R^1$ is H or halogen;
each $R^3$ or $R^5$ is independently H, $OR^a$, $N(R^a)_2$, $N_3$, CN, $NO_2$, $S(O)_nR^a$, halogen, $(C_1\text{-}C_8)$alkyl, $(C_4\text{-}C_8)$carbocyclylalkyl, $(C_1\text{-}C_8)$ substituted alkyl, $(C_2\text{-}C_8)$alkenyl, $(C_2\text{-}C_8)$ substituted alkenyl, $(C_2\text{-}C_8)$alkynyl or $(C_2\text{-}C_8)$ substituted alkynyl;
$R^6$ is $OR^a$, $N(R^a)_2$, $N_3$, CN, $S(O)_nR^a$, $-C(=O)R^{11}$, $-C(=O)OR^{11}$, $-C(=O)NR^{11}R^{12}$, $-C(=O)SR^{11}$, $-S(O)R^{11}$, $-S(O)_2R^{11}$, $-S(O)(OR^{11})$, $-S(O)_2(OR^{11})$, $-SO_2NR^{11}R^{12}$, halogen, $(C_1\text{-}C_8)$alkyl, $(C_4\text{-}C_8)$carbocyclylalkyl, $(C_1\text{-}C_8)$ substituted alkyl, $(C_2\text{-}C_8)$alkenyl, $(C_2\text{-}C_8)$ substituted alkenyl, $(C_2\text{-}C_8)$alkynyl, or $(C_2\text{-}C_8)$ substituted alkynyl;
each n is independently 0, 1, or 2;

each $R^a$ is independently H, $(C_1$-$C_8)$alkyl, $(C_2$-$C_8)$alkenyl, $(C_2$-$C_8)$alkynyl, aryl$(C_1$-$C_8)$alkyl, $(C_4$-$C_8)$carbocyclylalkyl, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), or —SO$_2$N$R^{11}R^{12}$;

$R^7$ is H, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), —SO$_2$N$R^{11}R^{12}$, or

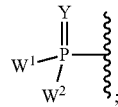

each Y or $Y^1$ is, independently, O, S, NR, $^+$N(O)(R), N(OR), $^+$N(O)(OR), or N—NR$_2$;

$W^1$ and $W^2$, when taken together, are —$Y^3$(C(R$^y$)$_2$)$_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of the Formula Ia:

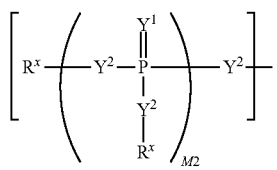

Formula Ia wherein:
each $Y^2$ is independently a bond, O, CR$_2$, NR, $^+$N(O)(R), N(OR), $^+$N(O)(OR), N—NR$_2$, S, S—S, S(O), or S(O)$_2$;
each $Y^3$ is independently O, S, or NR;
M2 is 0, 1 or 2;
each $R^x$ is independently $R^y$ or the formula:

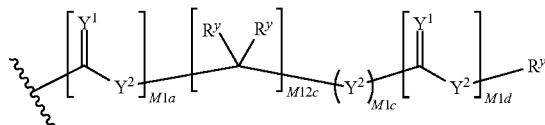

wherein:
each M1a, M1c, and M1d is independently 0 or 1;
M12c is 0, 1, 2, 3, 4, 5, 6, 7, 8, 9, 10, 11 or 12;
each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —SO$_2$NR$_2$, —CN, —N$_3$, —NO$_2$, —OR, or $W^3$; or when taken together, two $R^y$ on the same carbon atom form a carbocyclic ring of 3 to 7 carbon atoms;
each R is independently H, $(C_1$-$C_8)$ alkyl, $(C_1$-$C_8)$ substituted alkyl, $(C_2$-$C_8)$alkenyl, $(C_2$-$C_8)$ substituted alkenyl, $(C_2$-$C_8)$ alkynyl, $(C_2$-$C_8)$ substituted alkynyl, $C_6$-$C_{20}$ aryl, $C_6$-$C_{20}$ substituted aryl, $C_2$-$C_{20}$ heterocyclyl, $C_2$-$C_{20}$ substituted heterocyclyl, arylalkyl or substituted arylalkyl;
$W^3$ is $W^4$ or $W^5$; $W^4$ is R, —C($Y^1$)$R^y$, —C($Y^1$)$W^5$, —SO$_2R^y$, or —SO$_2W^5$; and $W^5$ is a carbocycle or a heterocycle wherein $W^5$ is independently substituted with 0 to 3 $R^y$ groups;

each $R^8$ is halogen, N$R^{11}R^{12}$, N($R^{11}$)O$R^{11}$, N$R^{11}$N$R^{11}R^{12}$, N$_3$, NO, NO$_2$, CHO, CN, —CH(=N$R^{11}$), —CH=NNHR$^{11}$, —CH=N(OR$^{11}$), —CH(OR$^{11}$)$_2$, —C(=O)N$R^{11}R^{12}$, —C(=S)N$R^{11}R^{12}$, —C(=O)O$R^{11}$, $(C_1$-$C_8)$alkyl, $(C_2$-$C_8)$alkenyl, $(C_2$-$C_8)$alkynyl, $(C_4$-$C_8)$carbocyclylalkyl, optionally substituted aryl, optionally substituted heteroaryl, —C(=O)$(C_1$-$C_8)$alkyl, —S(O)$_n(C_1$-$C_8)$alkyl, aryl$(C_1$-$C_8)$alkyl, O$R^{11}$ or S$R^{11}$;

each $R^9$ is independently H, halogen, N$R^{11}R^{12}$, N($R^{11}$)O$R^{11}$, N$R^{11}$N$R^{11}R^{12}$, N$_3$, NO, NO$_2$, CHO, CN, —CH(=N$R^{11}$), —CH=NHN$R^{11}$, —CH=N(OR$^{11}$), —CH(OR$^{11}$)$_2$, —C(=O)N$R^{11}R^{12}$, —C(=S)N$R^{11}R^{12}$, —C(=O)O$R^{11}$, $R^{11}$, O$R^{11}$ or S$R^{11}$;

each $R^{11}$ or $R^{12}$ is independently H, $(C_1$-$C_8)$alkyl, $(C_2$-$C_8)$alkenyl, $(C_2$-$C_8)$alkynyl, $(C_4$-$C_8)$carbocyclylalkyl, optionally substituted aryl, optionally substituted heteroaryl, —C(=O)$(C_1$-$C_8)$alkyl, —S(O)$_n(C_1$-$C_8)$alkyl or aryl$(C_1$-$C_8)$ alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —N$R^a$—; and wherein each $(C_1$-$C_8)$alkyl, $(C_2$-$C_8)$alkenyl, $(C_2$-$C_8)$alkynyl or aryl$(C_1$-$C_8)$alkyl of each $R^3$, $R^5$, $R^6$, $R^{11}$ or $R^{12}$ is, independently, optionally substituted with one or more halo, hydroxy, CN, N$_3$, N($R^a$)$_2$ or O$R^a$; and wherein one or more of the non-terminal carbon atoms of each said $(C_1$-$C_8)$alkyl may be optionally replaced with —O—, —S— or —N$R^a$—.

In one embodiment of the compound of Formula IV, $R^6$ is N$_3$, CN, halogen, $(C_1$-$C_8)$alkyl, $(C_1$-$C_8)$ substituted alkyl, $(C_2$-$C_8)$alkenyl, $(C_2$-$C_8)$ substituted alkenyl, $(C_2$-$C_8)$alkynyl, or $(C_2$-$C_8)$ substituted alkynyl. In another aspect of this embodiment, $R^6$ is CN, methyl, ethenyl, or ethynyl. In another aspect of this embodiment, $R^6$ is CN. In another aspect of this embodiment, $R^6$ is methyl. In another aspect of this embodiment, $R^1$ is H. In another aspect of this embodiment, $R^3$ is OH, —OC(=O)$R^{11}$, or —OC(=O)O$R^{11}$. In another aspect of this embodiment, $R^3$ is OH. In another aspect of this embodiment, $R^8$ is N$R^{11}R^{12}$. In another aspect of this embodiment, $R^8$ is NH$_2$. In another aspect of this embodiment, $R^8$ is O$R^{11}$. In another aspect of this embodiment, $R^8$ is OH. In another aspect of this embodiment, $R^9$ is H. In another aspect of this embodiment, $R^9$ is N$R^{11}R^{12}$. In another aspect of this embodiment, $R^9$ is NH$_2$. In another aspect of this embodiment, $R^7$ is H, —C(=O)$R^{11}$, —C(=O)O$R^{11}$ or

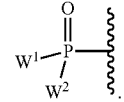

In another aspect of this embodiment, $R^7$ is H. In another aspect of this embodiment, $R^7$ is

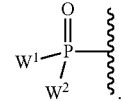

In another embodiment of a compound of Formula IV, $R^6$ is N$_3$, CN, halogen, $(C_1$-$C_8)$alkyl, $(C_1$-$C_8)$ substituted alkyl, $(C_2$-$C_8)$alkenyl, $(C_2$-$C_8)$ substituted alkenyl, $(C_2$-$C_8)$alkynyl, or (C$_2$-C$_8$) substituted alkynyl and R$^8$ is NH$_2$. In another aspect of this embodiment, R$^6$ is CN, methyl, ethenyl, or ethynyl. In another aspect of this embodiment, R$^6$ is CN. In another aspect of this embodiment, R$^6$ is methyl. In another aspect of this embodiment, R$^1$ is H. In another aspect of this embodiment, R$^3$ is OH, —OC(=O)R$^{11}$, or —OC(=O)OR$^{11}$. In another aspect of this embodiment, R$^3$ is OH. In another aspect of this embodiment, R$^9$ is H. In another aspect of this embodiment, R$^9$ is NR$^{11}$R$^{12}$. In another aspect of this embodiment, R$^9$ is NH$_2$. In another aspect of this embodiment, R$^7$ is H, —C(=O)R$^{11}$, —C(=O)OR$^{11}$ or $$\underset{W^2}{\overset{O}{\underset{\|}{W^1-P-}}}$$

In another aspect of this embodiment, R$^7$ is H. In another aspect of this embodiment, R$^7$ is $$\underset{W^2}{\overset{O}{\underset{\|}{W^1-P-}}}$$

In another embodiment of the compound of Formula IV, R$^6$ is CN, methyl, ethenyl, or ethynyl, R$^8$ is NH$_2$, and R$^9$ is H. In another aspect of this embodiment, R$^1$ is H. In another aspect of this embodiment, R$^6$ is CN. In another aspect of this embodiment, R$^6$ is methyl. In another aspect of this embodiment, R$^3$ is OH, —OC(=O)R$^{11}$, or —OC(=O)OR$^{11}$. In another aspect of this embodiment, R$^3$ is OH. In another aspect of this embodiment, R$^7$ is H, —C(=O)R$^{11}$, —C(=O)OR$^{11}$ or $$\underset{W^2}{\overset{O}{\underset{\|}{W^1-P-}}}$$

In another aspect of this embodiment, R$^7$ is H. In another aspect of this embodiment, R$^7$ is $$\underset{W^2}{\overset{O}{\underset{\|}{W^1-P-}}}$$

In another embodiment, provided is a method of treating a Paramyxoviridae infection in a mammal in need thereof comprising administering a therapeutically effective amount of a compound of Formulas I-IV, wherein R$^{11}$ or R$^{12}$ is independently H, (C$_1$-C$_8$)alkyl, (C$_2$-C$_8$)alkenyl, (C$_2$-C$_8$) alkynyl, (C$_4$-C$_8$)carbocyclylalkyl, optionally substituted aryl, optionally substituted heteroaryl, —C(=O)(C$_1$-C$_8$) alkyl, —S(O)$_n$(C$_1$-C$_8$)alkyl or aryl(C$_1$-C$_8$)alkyl. In another embodiment, R$^{11}$ and R$^{12}$ taken together with a nitrogen to which they are both attached, form a 3 to 7 membered heterocyclic ring wherein any one carbon atom of said heterocyclic ring can optionally be replaced with —O—, —S— or —NR$^a$—. Therefore, by way of example and not limitation, the moiety NR$^{11}$R$^{12}$ can be represented by the heterocycles:

and the like.

In another embodiment, provided is a method of treating a Paramyxoviridae infection in a mammal in need thereof comprising administering a therapeutically effective amount of a compound of Formula I-IV, wherein each R$^3$, R$^4$, R$^5$, R$^6$, R$^{11}$ or R$^{12}$ is, independently, (C$_1$-C$_8$)alkyl, (C$_2$-C$_8$) alkenyl, (C$_2$-C$_8$)alkynyl or aryl(C$_1$-C$_8$)alkyl, wherein said (C$_1$-C$_8$)alkyl, (C$_2$-C$_8$)alkenyl, (C$_2$-C$_8$)alkynyl or aryl(C$_1$-C$_8$)alkyl are, independently, optionally substituted with one or more halo, hydroxy, CN, N$_3$, N(R$^a$)$_2$ or OR$^a$. Therefore, by way of example and not limitation, R$^3$, R$^4$, R$^5$, R$^6$, R$^{11}$ or R$^{12}$ could represent moieties such as —CH(NH$_2$)CH$_3$, —CH(OH)CH2CH3, —CH(NH$_2$)CH(CH$_3$)$_2$, —CH$_2$CF$_3$, —(CH$_2$)$_2$CH(N$_3$)CH$_3$, —(CH$_2$)$_6$NH$_2$ and the like.

In another embodiment, provided is a method of treating a Paramyxoviridae infection in a mammal in need thereof comprising administering a therapeutically effective amount of a compound of Formula I-IV, wherein R$^3$, R$^4$, R$^5$, R$^6$, R$^{11}$ or R$^{12}$ is (C$_1$-C$_8$)alkyl wherein one or more of the non-terminal carbon atoms of each said (C$_1$-C$_8$)alkyl may be optionally replaced with —O—, —S— or —NR$^a$—. Therefore, by way of example and not limitation, R$^3$, R$^4$, R$^5$, R$^6$, R$^{11}$ or R$^{12}$ could represent moieties such as —CH$_2$OCH$_3$, —CH$_2$OCH$_2$CH$_3$, —CH$_2$OCH(CH$_3$)$_2$, —CH$_2$SCH$_3$, —(CH$_2$)$_6$OCH$_3$, —(CH$_2$)$_6$N(CH$_3$)$_2$ and the like.

In another embodiment, provided is a method of treating a Paramyxoviridae infection in a sample comprising administering an effective amount of a compound of Formula I selected from the group consisting of:

-continued
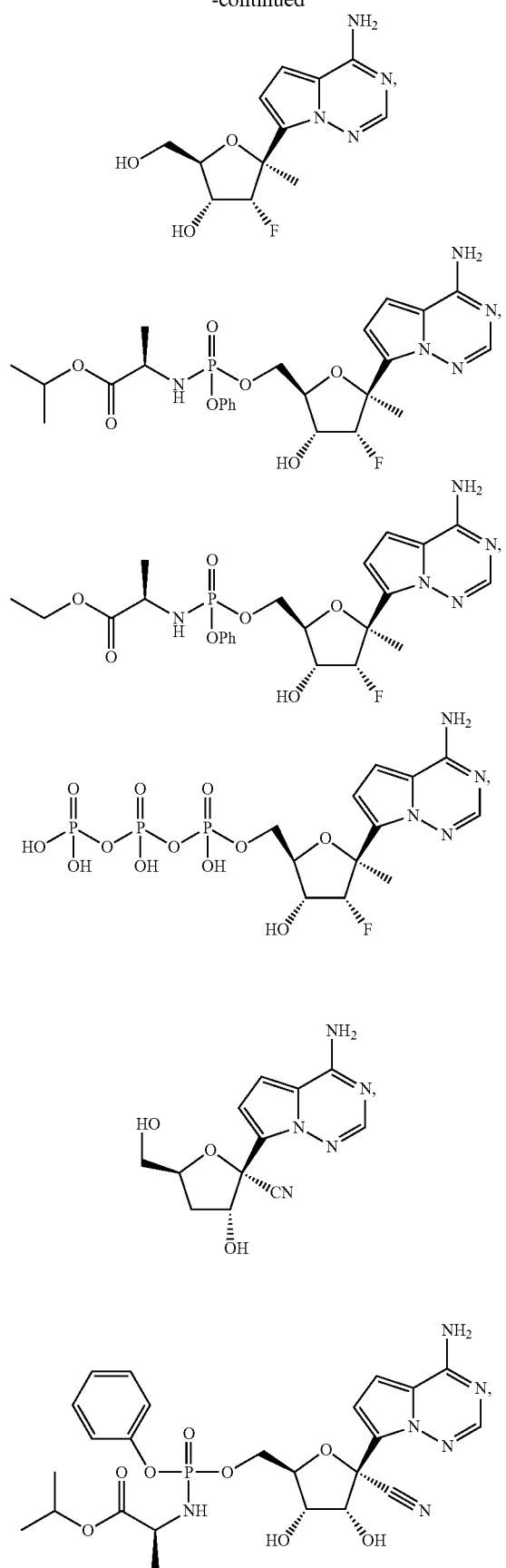
-continued
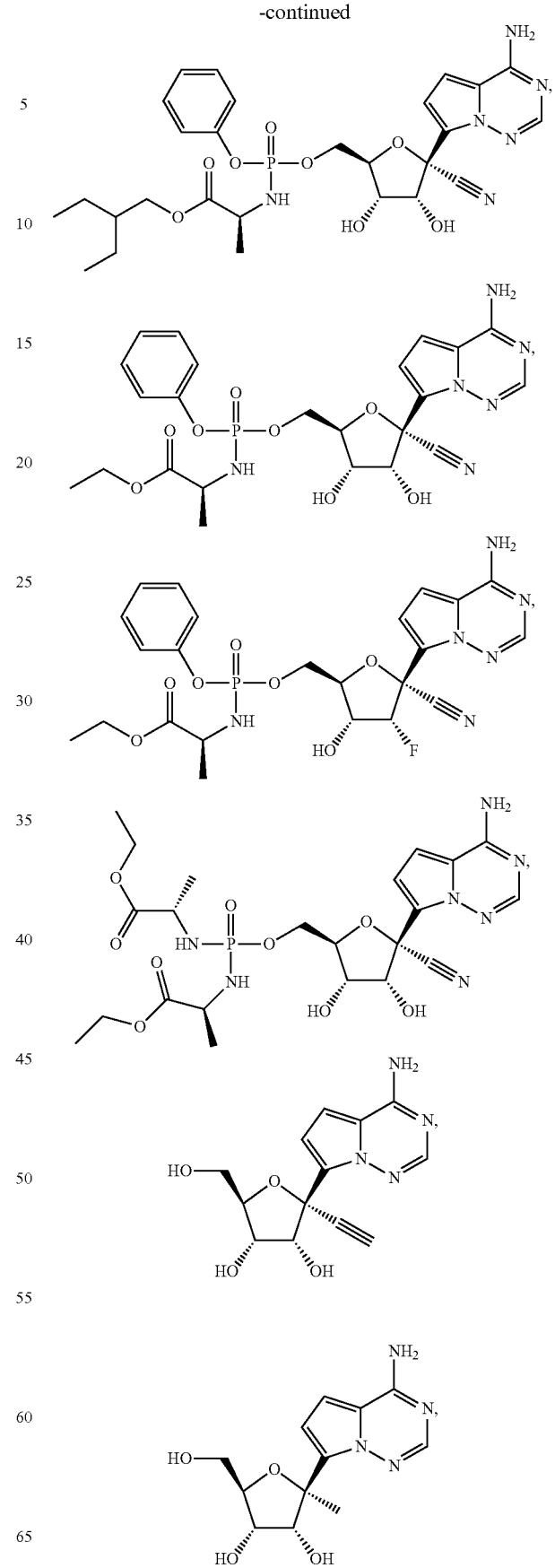

-continued
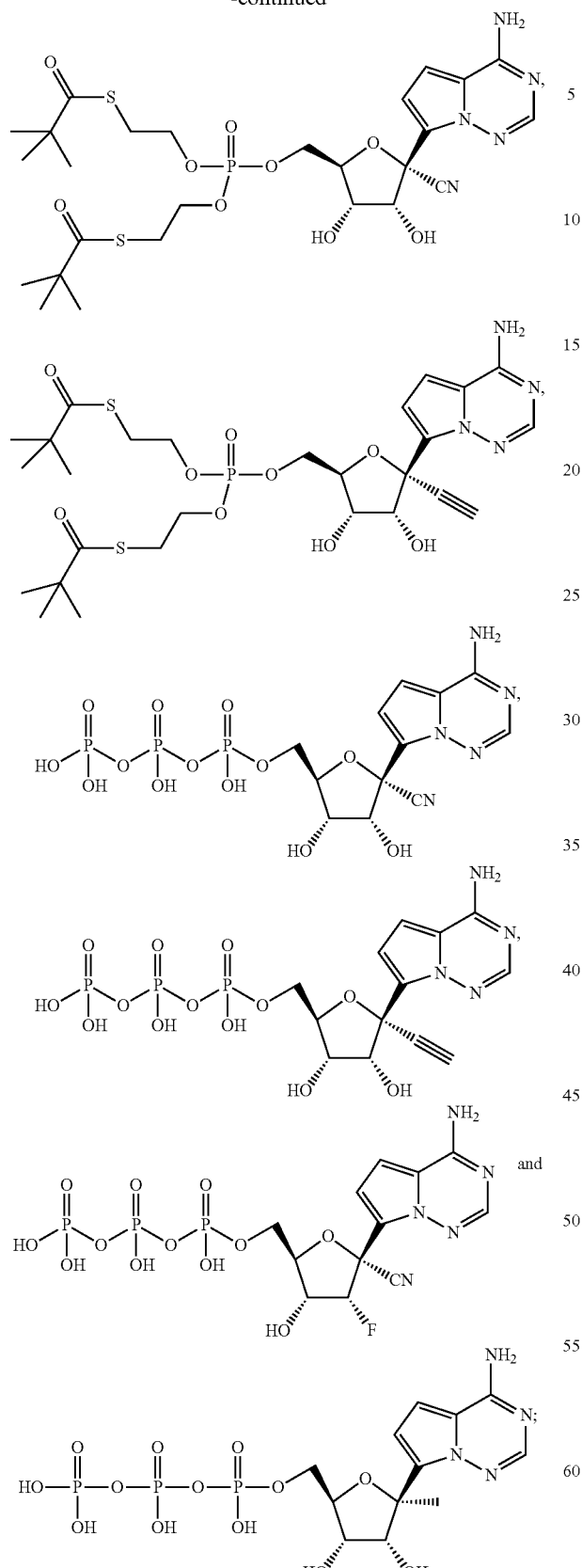
or a pharmaceutically acceptable salt or ester thereof.
In another embodiment, provided is a compound of Formula IV that is
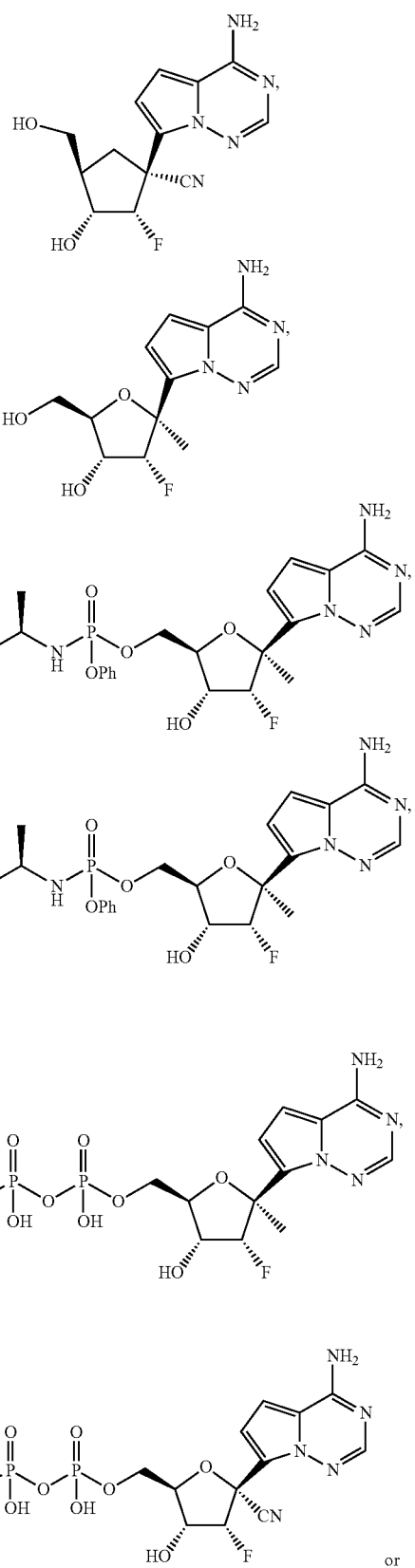
or

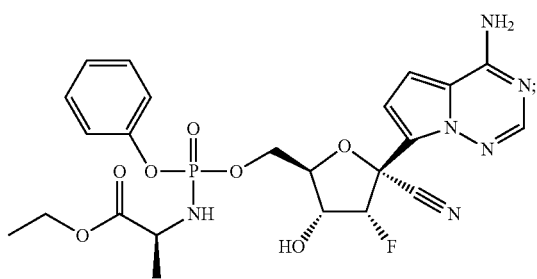 [SMILES: CCOC(=O)[C@H](C)NP(=O)(OC[C@H]1O[C@@](C#N)(c2ccc3c(N)ncnn23)[C@H](F)[C@@H]1O)Oc1ccccc1]
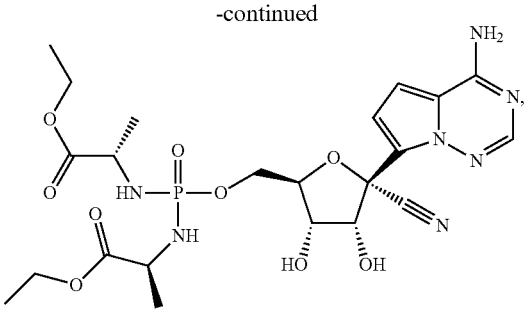
or a pharmaceutically acceptable salt or ester thereof.
In another embodiment, provided is a compound of Formula I that is
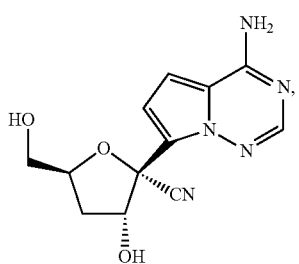
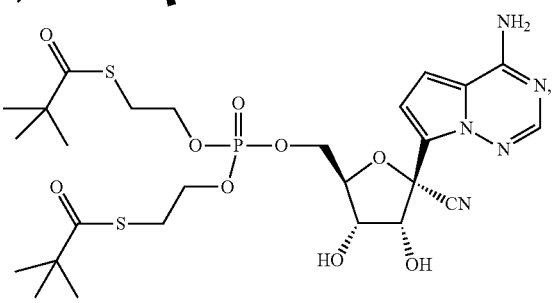
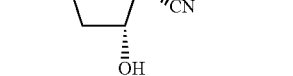
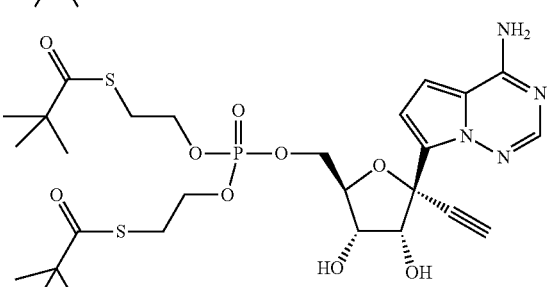
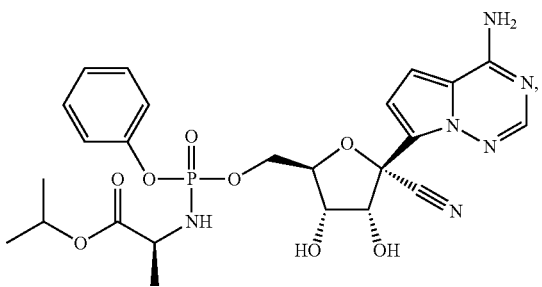
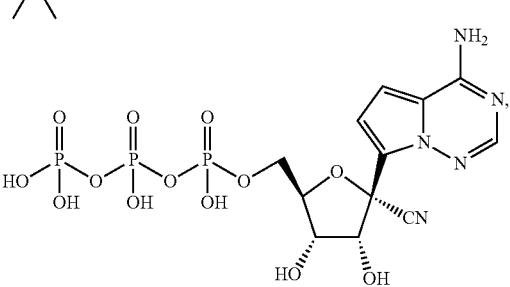
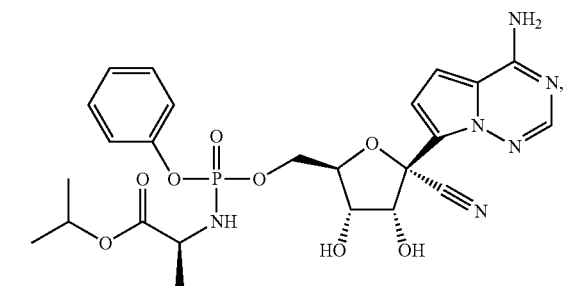
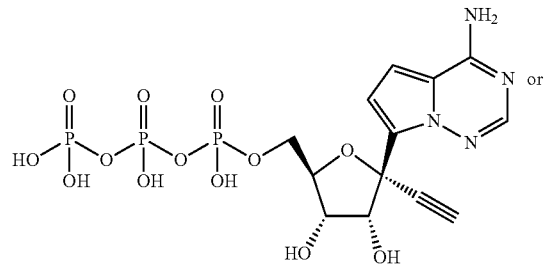
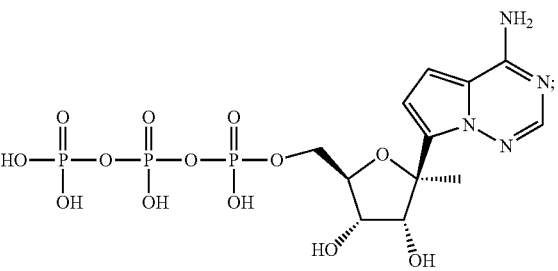
or a pharmaceutically acceptable salt or ester thereof.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Amino" refers generally to a nitrogen radical which can be considered a derivative of ammonia, having the formula —$N(X)_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —$NH_2$, —NH($CH_3$), —N($CH_3$)$_2$, —NH($CH_2CH_3$), —N($CH_2CH_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b_2$, —N$^+$R$^b_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b_2$, —S(=O)$_2$—, —S(=O)$_2$OH, —S(=O)$_2$R$^b$, —OS(=O)$_2$OR$^b$, —S(=O)$_2$NR$^b_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O$^-$), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b_2$, —C(S)NR$^b_2$, —C(=NR$^b$)NR$^b_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-IV should be selected in order to provide a compound which is sufficiently stable to provide a pharmaceutically useful compound which can be formulated into an acceptably stable pharmaceutical composition. Compounds of Formula I-IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

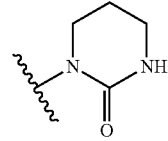 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

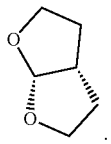

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to to an acyclic akyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I-III (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-III (e.g., the carbon atoms of said (C$_1$-C$_8$)alkyl may be optionally replaced by —O—, —S—, or —NR$^a$—) means that one or more of the methylene groups of the (C$_1$-C$_8$)alkyl may be replaced by 0, 1, 2, or more of the groups specified (e.g., —O—, —S—, or —NR$^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*)H$_2$(C*)H$_2$CH$_3$ or alkylene moiety —CH$_2$(C*)H$_2$(C*)H$_2$CH$_2$— the C* atoms would be considered to be the non-terminal carbon atoms.

Certain Y and Y$^1$ alternatives are nitrogen oxides such as $^+$N(O)(R) or $^+$N(O)(OR). These nitrogen oxides, as shown here attached to a carbon atom, can also be represented by charge separated groups such as

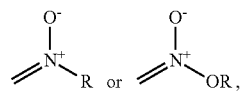

respectively, and are intended to be equivalent to the aforementioned representations for the purposes of describing this invention.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

In some embodiments of the compounds of Formula I-IV, one or more of W$^1$ or W$^2$ are independently a radical of a nitrogen-linked naturally occurring α-amino acid ester. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substitutent R, particularly those in which R is optionally substituted (C$_1$-C$_8$)alkyl.

The term "purine" or "pyrimidine" base comprises, but is not limited to, adenine, N$^6$-alkylpurines, N$^6$-acylpurines (wherein acyl is C(O)(alkyl, aryl, alkylaryl, or arylalkyl), N$^6$-benzylpurine, N$^6$-halopurine, N$^6$-vinylpurine, N$^6$-acetylenic purine, N$^6$-acyl purine, N$^6$-hydroxyalkyl purine, N$^6$-allylaminopurine, N$^6$-thioallyl purine, N$^2$-alkylpurines, N$^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-hydroxyalkyl purine, C$^5$-amidopyrimidine, C$^5$-cyanopyrimidine, C$^5$-5-iodopyrimidine, C$^6$-iodo-pyrimidine, C$^5$—Br-vinyl pyrimidine, C$^6$—Br-vinyl pyriniidine, C$^5$-nitropyrimidine, C$^5$-amino-pyrimidine, N$^2$-alkylpurines, N$^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. The purine and pyrimidine bases of Formula I-III are linked to the ribose sugar, or analog thereof, through a nitrogen atom of the base. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

Unless otherwise specified, the carbon atoms of the compounds of Formula I-IV are intended to have a valence of four. In some chemical structure representations where carbon atoms do not have a sufficient number of variables attached to produce a valence of four, the remaining carbon substituents needed to provide a valence of four should be assumed to be hydrogen. For example,

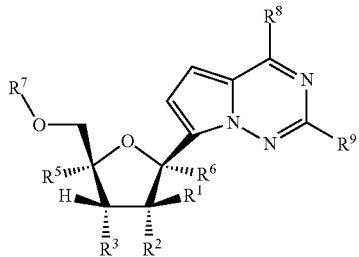

has the same meaning as

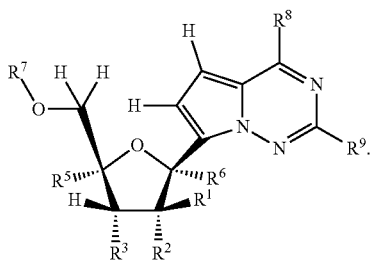

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

A prodrug moiety may include an active metabolite or drug itself.

Exemplary prodrug moieties include the hydrolytically sensitive or labile acyloxymethyl esters —$CH_2OC(=O)R^{30}$ and acyloxymethyl carbonates —$CH_2OC(=O)OR^{30}$ where $R^{30}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was used as a prodrug strategy for carboxylic acids and then applied to phosphates and phosphonates by Farquhar et al (1983) *J. Pharm. Sci.* 72: 324; also U.S. Pat. Nos. 4,816,570, 4,968,788, 5,663,159 and 5,792,756. In certain compounds of the invention, a prodrug moiety is part of a phosphate group. The acyloxyalkyl ester may be used to deliver phosphoric acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

The phosphate group may be a phosphate prodrug moiety. The prodrug moiety may be sensitive to hydrolysis, such as, but not limited to those comprising a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert et al (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans.* 12345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide.

Deesterification or reduction of the disulfide generates the free thio intermediate which subsequently breaks down to the phosphoric acid and episulfide (Puech et al (1993) *Antiviral Res.*, 22: 155-174; Benzaria et al (1996) *J. Med. Chem.* 39: 4958). Cyclic phosphonate esters have also been described as prodrugs of phosphorus-containing compounds (Erion et al, U.S. Pat. No. 6,312,662).

It is to be noted that all enantiomers, diastereomers, and racemic mixtures, tautomers, polymorphs, pseudopolymorphs of compounds within the scope of Formula I-IV and pharmaceutically acceptable salts thereof are embraced by the present invention. All mixtures of such enantiomers and diastereomers are within the scope of the present invention.

A compound of Formula I-IV and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-III and their pharmaceutically acceptable salts.

A compound of Formula I-IV and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-IV and their pharmaceutically acceptable salts.

Selected substituents comprising the compounds of Formula I-IV are present to a recursive degree. In this context, "recursive substituent" means that a substituent may recite another instance of itself. Because of the recursive nature of such substituents, theoretically, a large number of compounds may be present in any given embodiment. For example, $R^x$ comprises a $R^y$ substituent. $R^y$ can be R. R can be $W^3$. $W^3$ can be $W^4$ and $W^4$ can be R or comprise substituents comprising $R^y$. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $W^3$ and $R^y$ are recursive substituents in certain embodiments. Typically, each recursive substituent can independently occur 20, 19, 18, 17, 16, 15, 14, 13, 12, 11, 10, 9, 8, 7, 6, 5, 4, 3, 2, 1, or 0, times in a given embodiment. More typically, each recursive substituent can independently occur 12 or fewer times in a given embodiment. Even more typically, each recursive substituent can independently occur 3 or fewer times in a given embodiment. For example, $W^3$ will occur 0 to 8 times, $R^y$ will occur 0 to 6 times in a given embodiment.

Even more typically, $W^3$ will occur 0 to 6 times and $R^y$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I-IV present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I-IV, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

The compounds of the Formula I-IV may comprise a phosphate group as $R^7$, which may be a prodrug moiety

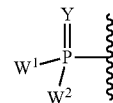

wherein each Y or $Y^1$ is, independently, O, S, NR, $^+$N(O)(R), N(OR), $^+$N(O)(OR), or N—$NR_2$; $W^1$ and $W^2$, when taken together, are —$Y^3(C(R^y)_2)_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of Formula Ia:

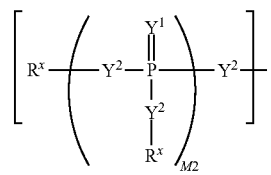

wherein:
each $Y^2$ is independently a bond, O, $CR_2$, NR, $^+$N(O)(R), N(OR), $^+$N(O)(OR), N—$NR_2$, S, S—S, S(O), or $S(O)_2$;

each $Y^3$ is independently O, S, or NR;

M2 is 0, 1 or 2;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$)N(R)$_2$, —SO$_2$NR$_2$, —CN, —N$_3$, —NO$_2$, —OR, a protecting group or $W^3$; or when taken together, two $R^y$ on the same carbon atom form a carbocyclic ring of 3 to 7 carbon atoms;

each $R^x$ is independently $R^y$, a protecting group, or the formula:

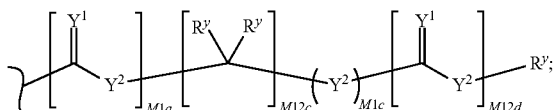

wherein:

M1a, M1c, and M1d are independently 0 or 1;

M12c is 0, 1, 2, 3, 4, 5, 6, 7, 8, 9, 10, 11 or 12;

each R is H, halogen, (C$_1$-C$_8$) alkyl, (C$_1$-C$_8$) substituted alkyl, (C$_2$-C$_8$) alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, C$_2$-C$_{20}$ heterocycle, C$_2$-C$_{20}$ substituted heterocyclyl, arylalkyl, substituted arylalkyl or a protecting group;

$W^3$ is $W^4$ or $W^5$; $W^4$ is R, —C($Y^1$)R$^y$, —C($Y^1$)W$^5$, —SO$_2$R$^y$, or —SO$_2$W$^5$; and $W^5$ is a carbocycle or a heterocycle wherein $W^5$ is independently substituted with 0 to 3 $R^y$ groups.

$W^5$ carbocycles and $W^5$ heterocycles may be independently substituted with 0 to 3 $R^y$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

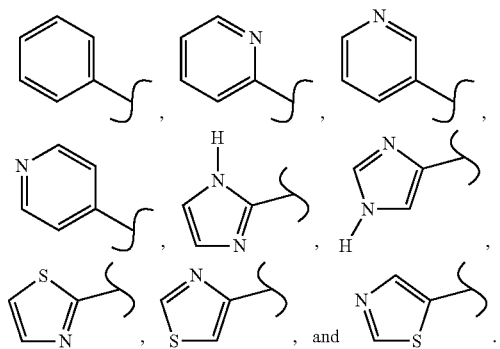

$W^5$ carbocycles and heterocycles may be independently substituted with 0 to 3 R groups, as defined above. For example, substituted $W^5$ carbocycles include:

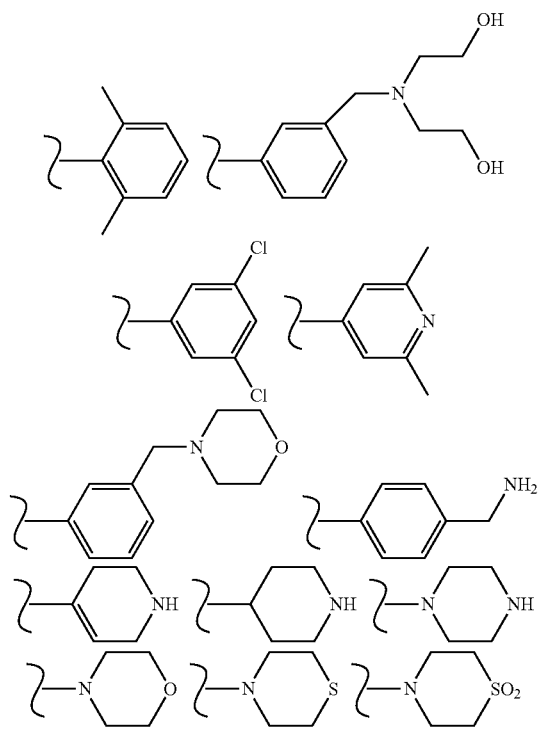

Examples of substituted phenyl carbocycles include:

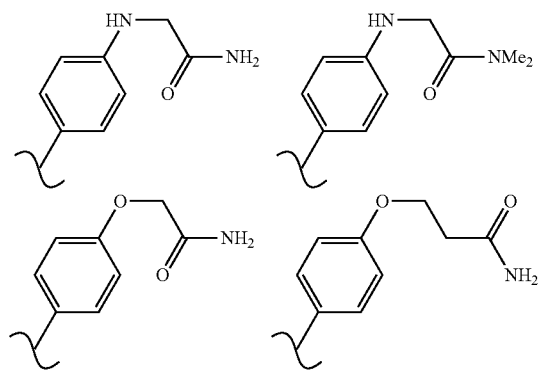

-continued

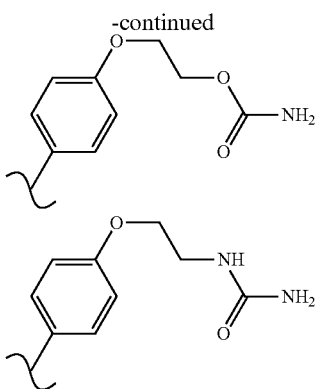

Embodiments of

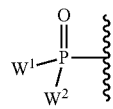

of Formula I-IV compounds include substructures such as:

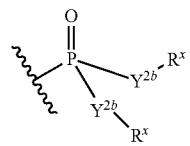

wherein each $Y^{2b}$ is, independently, O or N(R). In another aspect of this embodiment, each $Y^{2b}$ is O and each $R^x$ is independently:

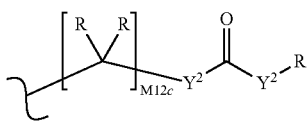

wherein M12c is 1, 2 or 3 and each $Y^2$ is independently a bond, O, $CR_2$, or S. In another aspect of this embodiment, one $Y^{2b}$—$R^x$ is NH(R) and the other $Y^{2b}$—$R^x$ is O—$R^x$ wherein $R^x$ is:

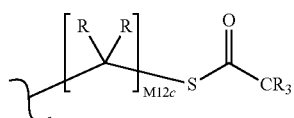

wherein M12c is 2. In another aspect of this embodiment, each $Y^{2b}$ is O and each $R^x$ is independently:

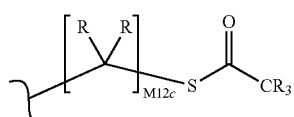

wherein M12c is 2. In another aspect of this embodiment, each $Y^{2b}$ is O and each $R^x$ is independently:

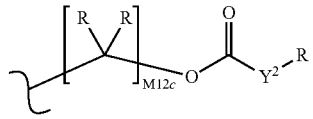

wherein M12c is 1 and $Y^2$ is a bond, O, or $CR_2$.

Other embodiments of

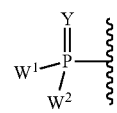

of Formulas I-IV compounds include substructures such as:

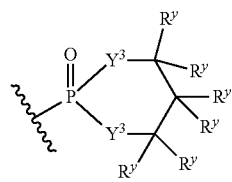

wherein each $Y^3$ is, independently, O or N(R). In another aspect of this embodiment, each $Y^3$ is O. In another aspect of this embodiment, the substructure is:

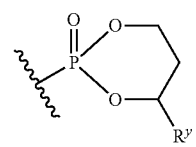

wherein $R^y$ is $W^5$ as defined herein.

Another embodiment of

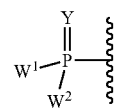

of Formula I-IV includes the substructures:

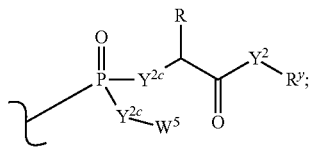

wherein each $Y^{2c}$ is, independently, O, N($R^y$) or S.

Another embodiment of

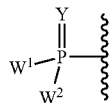

of Formula I-IV compounds includes the substructures wherein one of $W^1$ or $W^2$ together with either $R^3$ or $R^4$ is —$Y^3$— and the other of $W^1$ or $W^2$ is Formula Ia. Such an embodiment is represented by a compound of Formula Ib selected from:

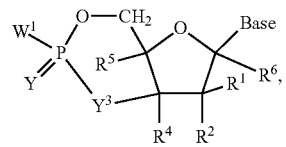

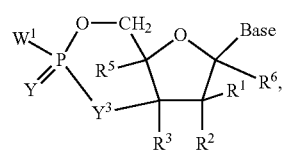

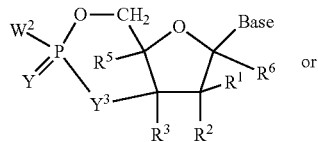

or

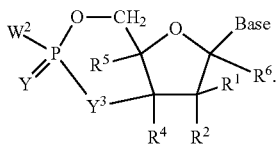

Formula Ib

In another aspect of the embodiment of Formula Ib, each Y and $Y^3$ is O. In another aspect of the embodiment of Formula Ib, $W^1$ or $W^2$ is $Y^{2b}$—$R^x$; each Y, $Y^3$ and $Y^{2b}$ is O and $R^x$ is:

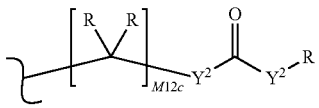

wherein M12c is 1, 2 or 3 and each $Y^2$ is independently a bond, O, $CR_2$, or S. In another aspect of the embodiment of Formula Ib, $W^1$ or $W^2$ is $Y^{2b}$—$R^x$; each Y, $Y^3$ and $Y^{2b}$ is O and $R^x$ is:

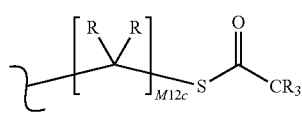

wherein M12c is 2. In another aspect of the embodiment of Formula Ib, $W^1$ or $W^2$ is $Y^{2b}$—$R^x$; each Y, $Y^3$ and $Y^{2b}$ is O and $R^x$ is:

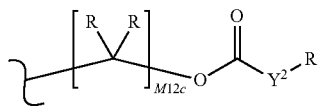

wherein M12c is 1 and $Y^2$ is a bond, O, or $CR_2$.

Another embodiment of

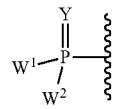

of Formula I-IV compounds includes a substructure:

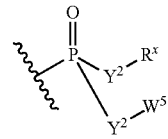

wherein $W^5$ is a carbocycle such as phenyl or substituted phenyl. In another aspect of this embodiment, the substructure is:

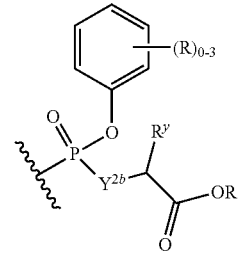

wherein $Y^{2b}$ is O or N(R) and the phenyl carbocycle is substituted with 0 to 3 R groups. In another aspect of this embodiment of the substructure, $R^x$ is:

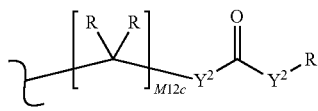

wherein M12c is 1, 2 or 3 and each $Y^2$ is independently a bond, O, $CR_2$, or S.

Another embodiment of

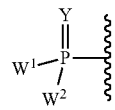

of Formula I-IV includes substructures:

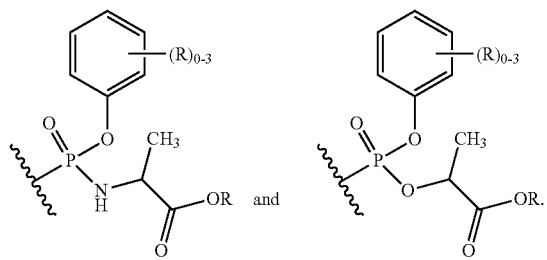

The chiral carbon of the amino acid and lactate moieties may be either the R or S configuration or the racemic mixture.

Another embodiment of

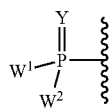

of Formula I-IV is substructure

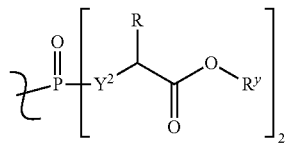

wherein each $Y^2$ is, independently, —O— or —NH—. In another aspect of this embodiment, $R^y$ is $(C_1$-$C_8)$ alkyl, $(C_1$-$C_8)$ substituted alkyl, $(C_2$-$C_8)$ alkenyl, $(C_2$-$C_8)$ substituted alkenyl, $(C_2$-$C_8)$ alkynyl or $(C_2$-$C_8)$ substituted alkynyl. In another aspect of this embodiment, $R^y$ is $(C_1$-$C_8)$ alkyl, $(C_1$-$C_8)$ substituted alkyl, $(C_2$-$C_8)$ alkenyl, $(C_2$-$C_8)$ substituted alkenyl, $(C_2$-$C_8)$ alkynyl or $(C_2$-$C_8)$ substituted alkynyl; and R is $CH_3$. In another aspect of this embodiment, $R^y$ is $(C_1$-$C_8)$ alkyl, $(C_1$-$C_8)$ substituted alkyl, $(C_2$-$C_8)$ alkenyl, $(C_2$-$C_8)$ substituted alkenyl, $(C_2$-$C_8)$ alkynyl or $(C_2$-$C_8)$ substituted alkynyl; R is $CH_3$; and each $Y^2$ is —NH—. In another aspect of this embodiment, $W^1$ and $W^2$ are, independently, nitrogen-linked, naturally occurring amino acids or naturally occurring amino acid esters. In another aspect of this embodiment, $W^1$ and $W^2$ are, independently, naturally-occurring 2-hydroxy carboxylic acids or naturally-occurring 2-hydroxy carboxylic acid esters wherein the acid or ester is linked to P through the 2-hydroxy group.

Another embodiment of

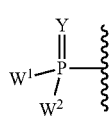

of Formula I-IV is substructure:

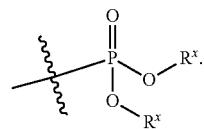

In one aspect of this embodiment, each $R^x$ is, independently, $(C_1$-$C_8)$ alkyl. In another aspect of this embodiment, each $R^x$ is, independently, $C_6$-$C_{20}$ aryl or $C_6$-$C_{20}$ substituted aryl.

In a preferred embodiment,

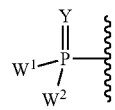

is selected from

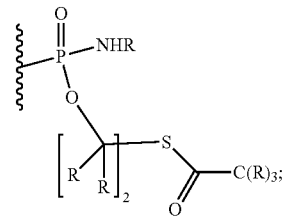

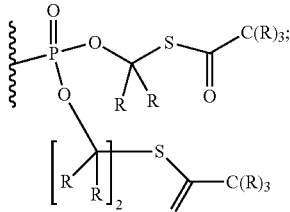

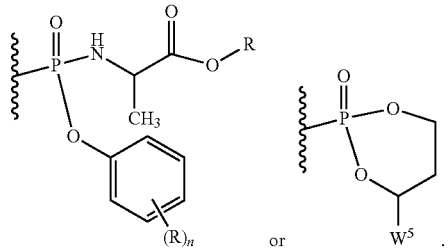

Another embodiment of

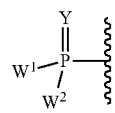

of Formulas I-IV is substructure

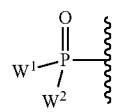

wherein $W^1$ and $W^2$ are independently selected from one of the formulas in Tables 20.1-20.37 and Table 30.1 below. The variables used in Tables 20.1-20.37 (e.g., $W^{23}$, $R^{21}$, etc.) pertain only to Tables 20.1-20.37, unless otherwise indicated.

The variables used in Tables 20.1 to 20.37 have the following definitions:

each $R^{21}$ is independently H or ($C_1$-$C_8$)alkyl;

each $R^{22}$ is independently H, $R^{21}$, $R^{23}$ or $R^{24}$ wherein each $R^{24}$ is independently substituted with 0 to 3 $R^{23}$;

each $R^{23}$ is independently $R^{23a}$, $R^{23b}$, $R^{23c}$ or $R^{23d}$, provided that when $R^{23}$ is bound to a heteroatom, then $R^{23}$ is $R^{23c}$ or $R^{23d}$;

each $R^{23a}$ is independently F, Cl, Br, I, —CN, $N_3$ or —$NO_2$;

each $R^{23b}$ is independently $Y^{21}$;

each $R^{23c}$ is independently —$R^{2x}$, —N($R^{2x}$)($R^{2x}$), —$SR^{2x}$, —S(O)$R^{2x}$, —S(O)$_2R^{2x}$, —S(O)(O$R^{2x}$), —S(O)$_2$(O$R^{2x}$), —OC(=$Y^{21}$)$R^{2x}$, —OC(=$Y^{21}$)O$R^{2x}$, —OC(=$Y^{21}$)(N($R^{2x}$)($R^{2x}$)), —SC(=$Y^{21}$)$R^{2x}$, —SC(=$Y^{21}$)O$R^{2x}$, —SC(=$Y^{21}$)(N($R^{2x}$)($R^{2x}$)), —N($R^{2x}$)(C(=$Y^{21}$)$R^{2x}$, —N($R^{2x}$)C(=$Y^{21}$)O$R^{2x}$, or —N($R^{2x}$)C(=$Y^{21}$)(N($R^{2x}$)($R^{2x}$));

each $R^{23d}$ is independently —C(=$Y^{21}$)$R^{2x}$, —C(=$Y^{21}$)O$R^{2x}$ or —C(=$Y^{21}$)(N($R^{2x}$)($R^{2x}$));

each $R^{2x}$ is independently H, ($C_1$-$C_8$)alkyl, ($C_2$-$C_8$)alkenyl, ($C_2$-$C_8$)alkynyl, aryl, heteroaryl; or two $R^{2x}$ taken together with a nitrogen to which they are both attached form a 3 to 7 membered heterocyclic ring wherein any one carbon atom of said heterocyclic ring can optionally be replaced with —O—, —S— or —$NR^{21}$—; and wherein one or more of the non-terminal carbon atoms of each said ($C_1$-$C_8$)alkyl may be optionally replaced with —O—, —S— or —$NR^{21}$—;

each $R^{24}$ is independently ($C_1$-$C_8$)alkyl, ($C_2$-$C_8$)alkenyl, or ($C_2$-$C_8$)alkynyl;

each $R^{25}$ is independently $R^{24}$ wherein each $R^{24}$ is substituted with 0 to 3 $R^{23}$ groups;

each $R^{25a}$ is independently ($C_1$-$C_8$)alkylene, ($C_2$-$C_8$)alkenylene, or ($C_2$-$C_8$)alkynylene any one of which said ($C_1$-$C_8$)alkylene, ($C_2$-$C_8$)alkenylene, or ($C_2$-$C_8$)alkynylene is substituted with 0-3 $R^{23}$ groups;

each $W^{23}$ is independently $W^{24}$ or $W^{25}$;

each $W^{24}$ is independently $R^{25}$, —C(=$Y^{21}$)$R^{25}$, —C(=$Y^{21}$)$W^{25}$, —$SO_2R^{25}$, —$SO_2W^{25}$;

each $W^{25}$ is independently carbocycle or heterocycle wherein $W^{25}$ is independently substituted with 0 to 3 $R^{22}$ groups; and each $Y^{21}$ is independently O or S.

TABLE 20.1

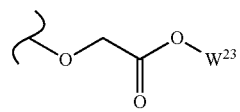

1

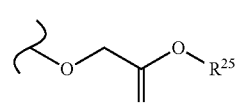

2

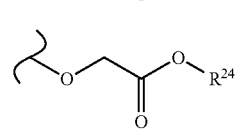

3

TABLE 20.1-continued

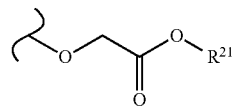

4

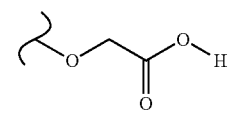

5

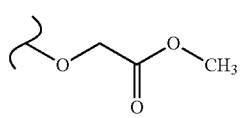

6

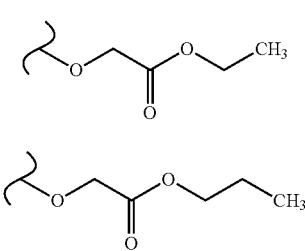

7

8

TABLE 20.2

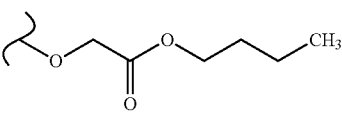

9

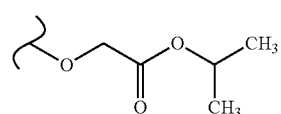

10

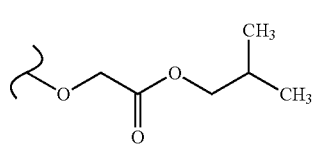

11

TABLE 20.3

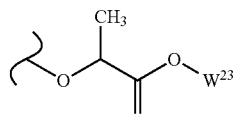

12

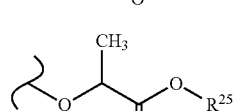

13

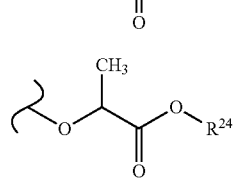

14

TABLE 20.3-continued
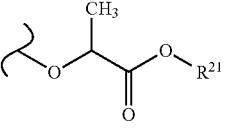 15
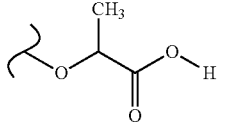 16
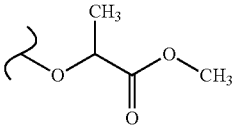 17
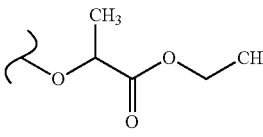 18
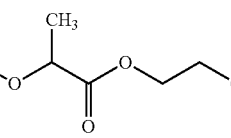 19
TABLE 20.4
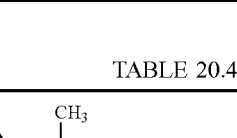 20
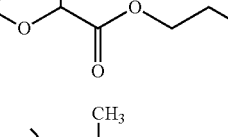 21
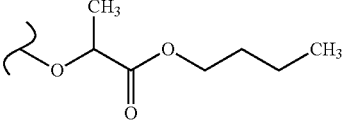 22
TABLE 20.5
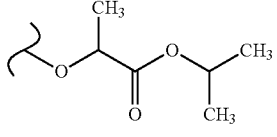 23
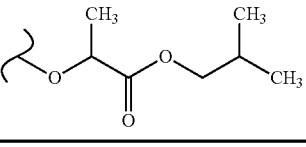 24
TABLE 20.5-continued
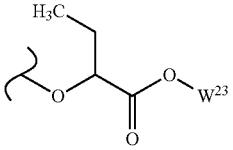 25
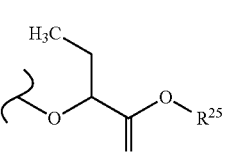 26
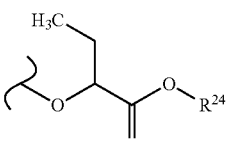 27
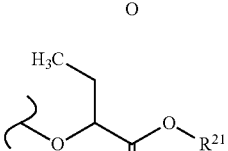 28
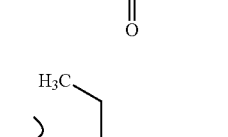 29
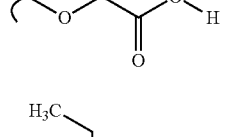 30
TABLE 20.6
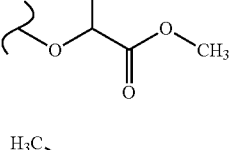 31
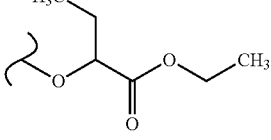 32
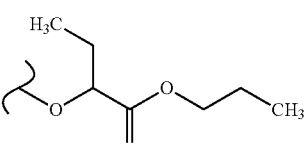 33

TABLE 20.7
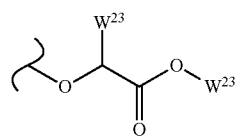 34
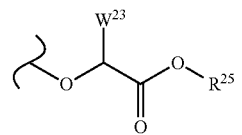 35
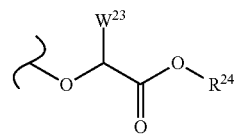 36
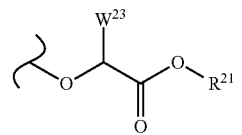 37
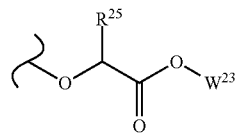 38
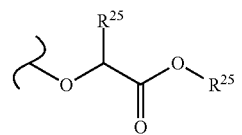 39
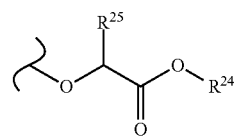 40
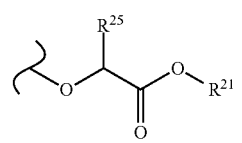 41
TABLE 20.8
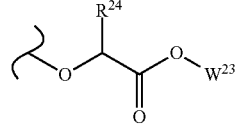 42
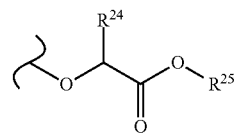 43
TABLE 20.8-continued
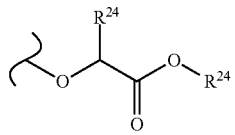 44
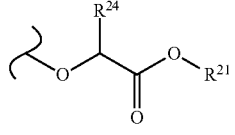 45
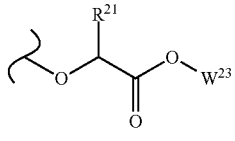 46
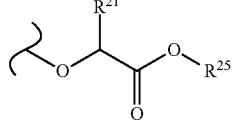 47
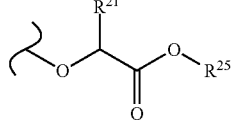 48
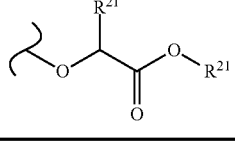 49
TABLE 20.9
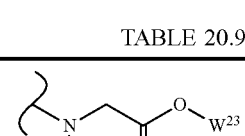 50
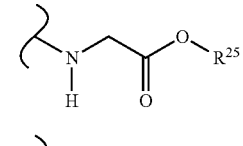 51
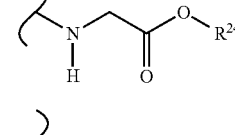 52
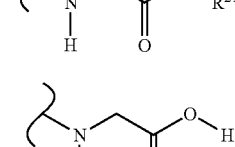 53
 54

TABLE 20.9-continued
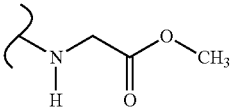 55
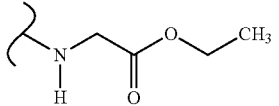 56
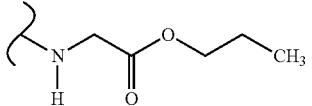 57
TABLE 20.10
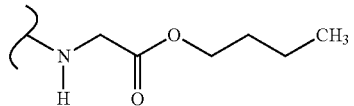 58
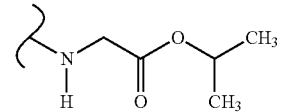 59
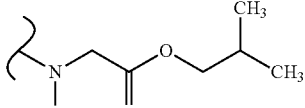 60
TABLE 20.11
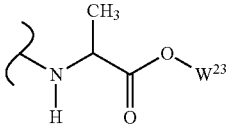 61
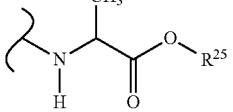 62
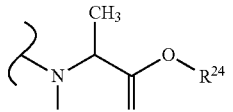 63
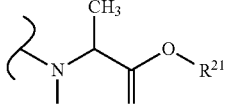 64
TABLE 20.11-continued
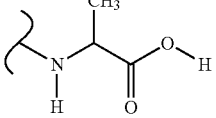 65
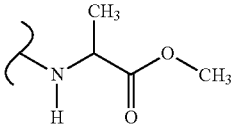 66
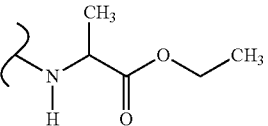 67
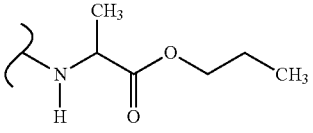 68
TABLE 20.12
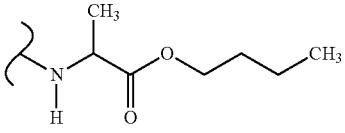 69
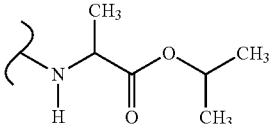 70
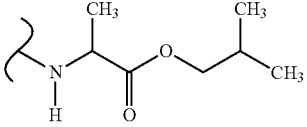 71
TABLE 20.13
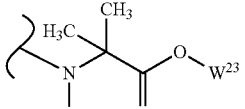 72
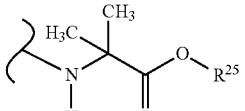 73
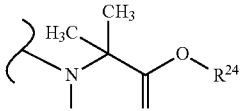 74

TABLE 20.13-continued

| Structure | # |
|---|---|
| (amino acid ester with CH₃, CH₃, OR²¹) | 75 |
| (amino acid with CH₃, CH₃, OH) | 76 |
| (amino acid methyl ester with CH₃, CH₃, OCH₃) | 77 |
| (amino acid ethyl ester with CH₃, CH₃, OCH₂CH₃) | 78 |
| (amino acid propyl ester with CH₃, CH₃, OCH₂CH₂CH₃) | 79 |

TABLE 20.14

| Structure | # |
|---|---|
| (amino acid butyl ester) | 80 |
| (amino acid isopropyl ester) | 81 |
| (amino acid isobutyl ester) | 82 |

TABLE 20.15

| Structure | # |
|---|---|
| (W²³, O-W²³) | 83 |
| (W²³, O-R²⁵) | 84 |
| (W²³, O-R²⁴) | 85 |
| (W²³, O-R²¹) | 86 |
| (R²⁵, O-W²³) | 87 |
| (R²⁵, O-R²⁵) | 88 |
| (R²⁵, O-R²⁴) | 89 |
| (R²⁵, O-R²¹) | 90 |

TABLE 20.16

| Structure | # |
|---|---|
| (R²⁴, O-W²³) | 91 |
| (R²⁴, O-R²⁵) | 92 |
| (R²⁴, O-R²⁴) | 93 |
| (R²⁴, O-R²¹) | 94 |

TABLE 20.16-continued
| | |
|---|---|
| 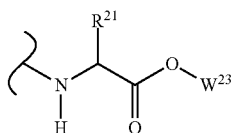 | 95 |
| 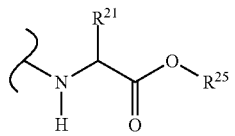 | 96 |
| 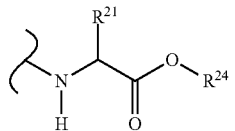 | 97 |
| 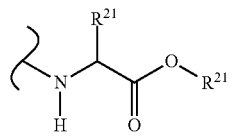 | 98 |
TABLE 20.17
| | |
|---|---|
| 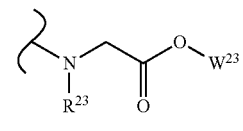 | 99 |
| 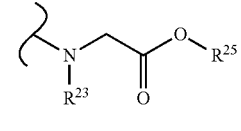 | 100 |
| 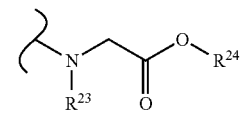 | 101 |
| 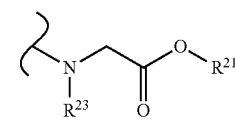 | 102 |
| 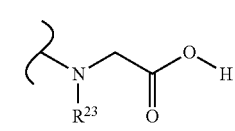 | 103 |
| 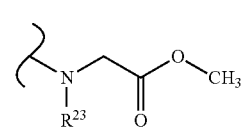 | 104 |
| 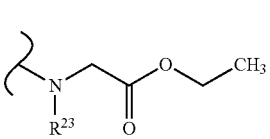 | 105 |
TABLE 20.17-continued
| | |
|---|---|
| 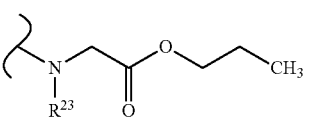 | 106 |
TABLE 20.18
| | |
|---|---|
| 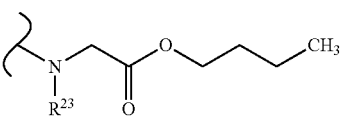 | 107 |
| 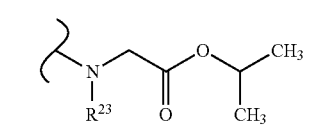 | 108 |
| 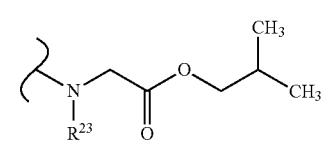 | 109 |
TABLE 20.19
| | |
|---|---|
| 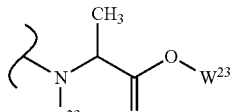 | 110 |
| 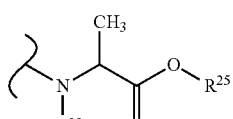 | 111 |
| 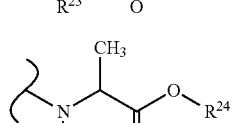 | 112 |
| 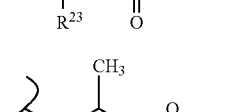 | 113 |
| 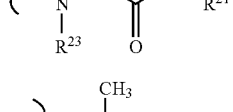 | 114 |
| 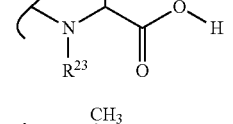 | 115 |
| 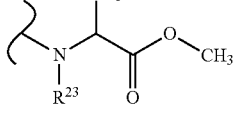 | |

TABLE 20.19-continued
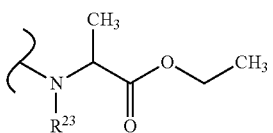 116
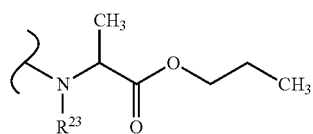 117
TABLE 20.20
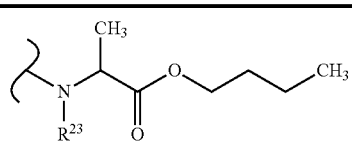 118
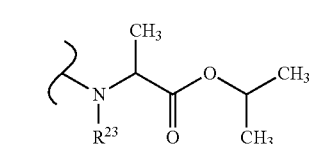 119
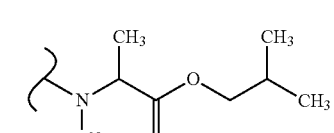 120
TABLE 20.21
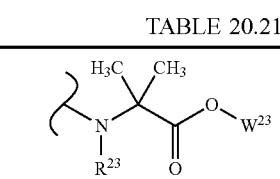 121
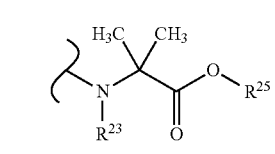 122
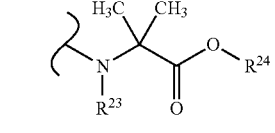 123
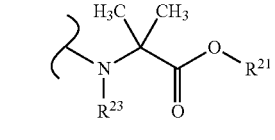 124
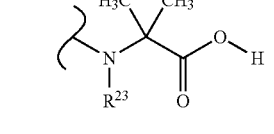 125
TABLE 20.21-continued
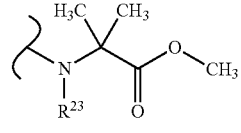 126
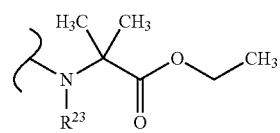 127
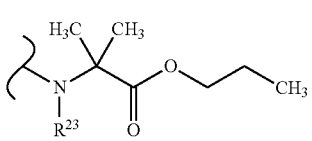 128
TABLE 20.22
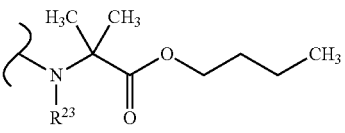 129
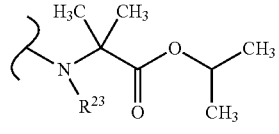 130
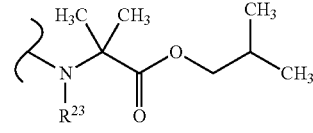 131
TABLE 20.23
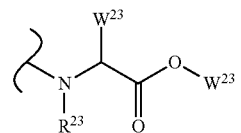 132
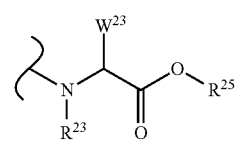 133
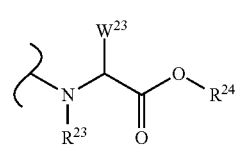 134
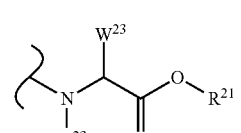 135

TABLE 20.23-continued
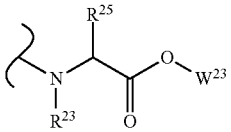 136
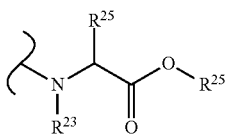 137
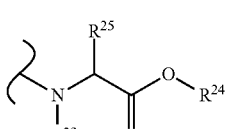 138
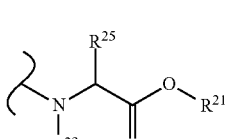 139
TABLE 20.24
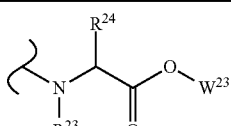 140
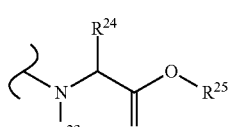 141
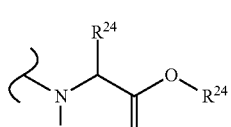 142
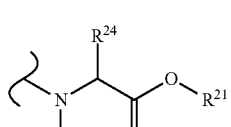 143
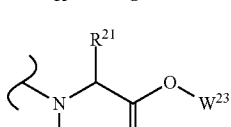 144
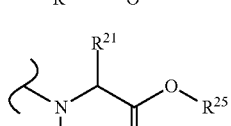 145
TABLE 20.24-continued
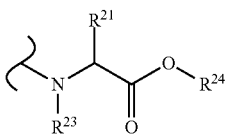 146
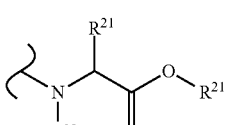 147
TABLE 20.25
 148
 149
 150
 151
 152
 153
 154
 155
 156
 157
 158
 159
TABLE 20.26
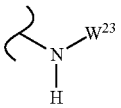 160
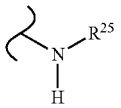 161

TABLE 20.26-continued

| Structure | # |
|---|---|
| -N(H)R²⁴ | 162 |
| -N(H)R²¹ | 163 |
| -N(H)H (i.e., -NH₂) | 164 |
| -N(H)R²³ | 165 |
| -N(R²³)W²³ | 166 |
| -N(R²³)R²⁵ | 167 |
| -N(R²³)R²⁴ | 168 |
| -N(R²³)R²¹ | 169 |
| -N(R²³)H | 170 |
| -N(R²³)R²³ | 171 |

TABLE 20.27

| Structure | # |
|---|---|
| -O-R²⁵ᵃ-O-C(O)-W²³ | 172 |
| -O-R²⁵ᵃ-O-C(O)-R²⁵ | 173 |
| -O-R²⁵ᵃ-O-C(O)-R²⁴ | 174 |

TABLE 20.27-continued

| Structure | # |
|---|---|
| -O-R²⁵ᵃ-O-C(O)-R²¹ | 175 |
| -O-R²⁵ᵃ-O-C(O)-H | 176 |
| -O-R²⁵ᵃ-O-C(O)-CH₃ | 177 |
| -O-R²⁵ᵃ-O-C(O)-CH₂CH₃ | 178 |
| -O-R²⁵ᵃ-O-C(O)-CH₂CH₂CH₃ | 179 |

TABLE 20.28

| Structure | # |
|---|---|
| -O-R²⁵ᵃ-O-C(O)-CH₂CH₂CH₂CH₃ | 180 |
| -O-R²⁵ᵃ-O-C(O)-CH(CH₃)₂ | 181 |
| -O-R²⁵ᵃ-O-C(O)-C(CH₃)₃ | 182 |
| -O-R²⁵ᵃ-O-C(O)-CH₂CH(CH₃)₂ | 183 |
| -O-R²⁵ᵃ-O-C(O)-C₆H₅ | 184 |
| -O-R²⁵ᵃ-O-C(O)-CH₂-C₆H₅ | 185 |

TABLE 20.29

| Structure | # |
|---|---|
| -O-CH₂-O-C(O)-W²³ | 186 |

TABLE 20.29-continued
| | |
|---|---|
| 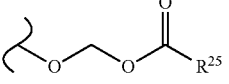 | 187 |
| 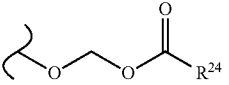 | 188 |
| 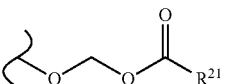 | 189 |
| 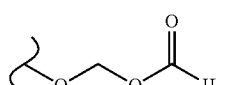 | 190 |
| 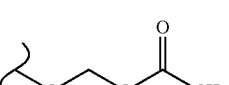 | 191 |
| 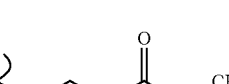 | 192 |
| 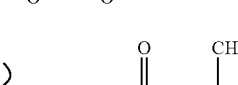 | 193 |
TABLE 20.30
| | |
|---|---|
| 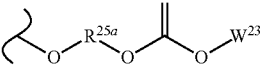 | 194 |
| 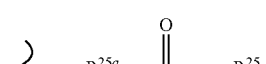 | 195 |
| 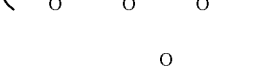 | 196 |
| 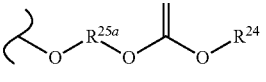 | 197 |
| 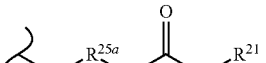 | 198 |
|  | 199 |
TABLE 20.31
| | |
|---|---|
| 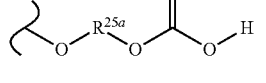 | 200 |
| 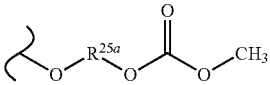 | 201 |
| 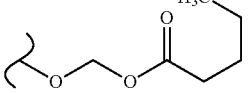 | 202 |
| 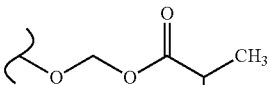 | 203 |
| 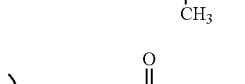 | 204 |
| 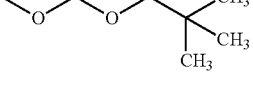 | 205 |
| 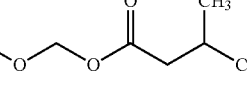 | 206 |
| 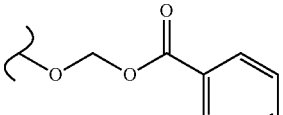 | 207 |
TABLE 20.32
| | |
|---|---|
|  | 208 |
| 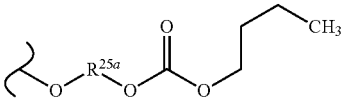 | 209 |
| 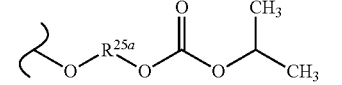 | 210 |
| 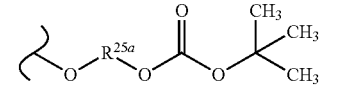 | 211 |
| 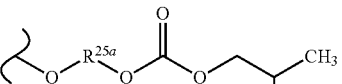 | 212 |

TABLE 20.32-continued
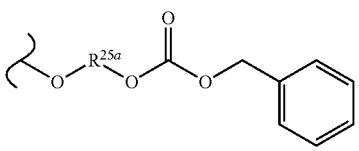
213
TABLE 20.33
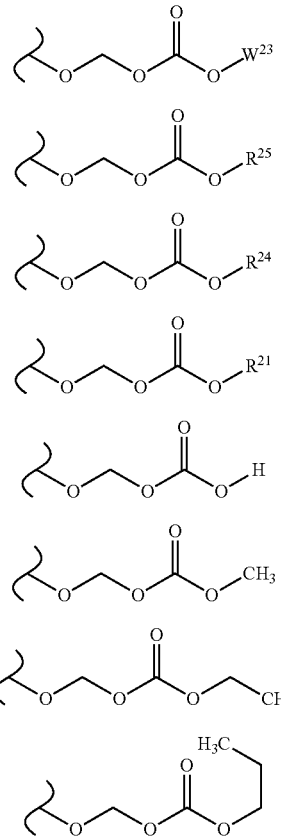
214
215
216
217
218
219
220
221
TABLE 20.34
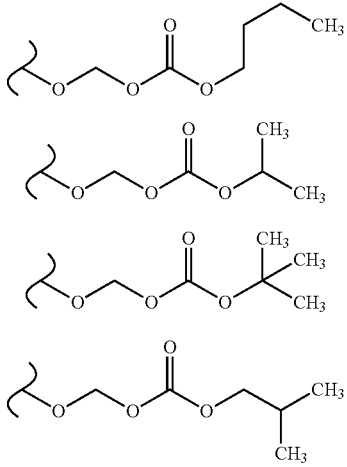
222
223
224
225
TABLE 20.34-continued
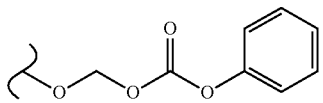
226
227
TABLE 20.35
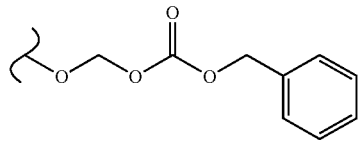
228
229
230
231
232
233
234
235
TABLE 20.36
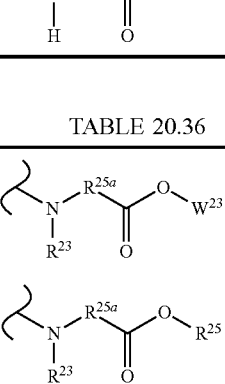
236
237

TABLE 20.36-continued
| | |
|---|---|
| 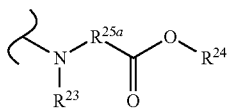 | 238 |
| 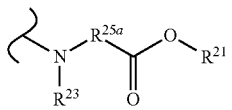 | 239 |
| 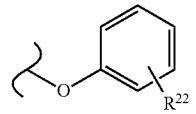 | 240 |
| 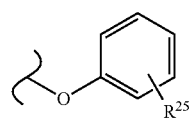 | 241 |
| 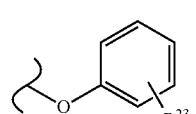 | 242 |
| 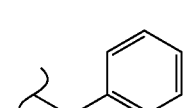 | 243 |
TABLE 20.37
| | |
|---|---|
|  | 244 |
| 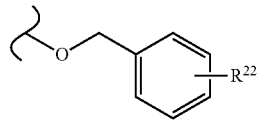 | 245 |
| 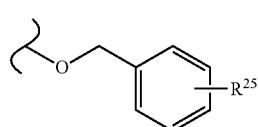 | 246 |
| 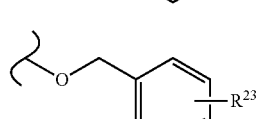 | 247 |
TABLE 30.1
| | |
|---|---|
| 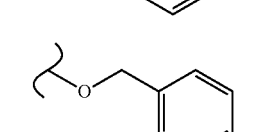 | 67 |
TABLE 30.1-continued
| | |
|---|---|
| 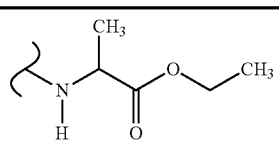 | 68 |
| 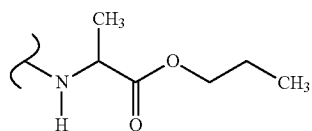 | 69 |
| 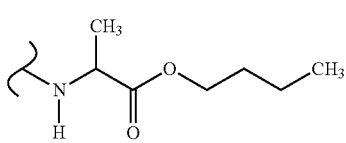 | 70 |
| 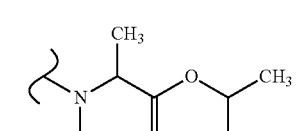 | 71 |
| 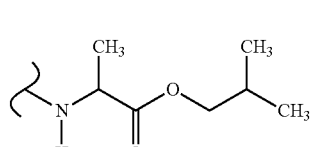 | 258 |
| 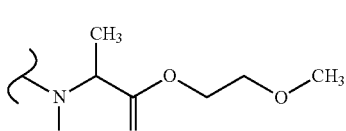 | 248 |
| 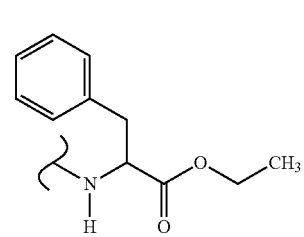 | 249 |
| 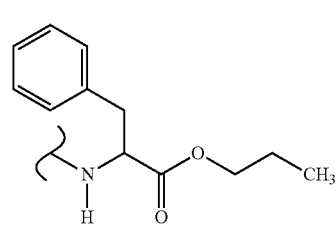 [SMILES: CCCOC(=O)C(Cc1ccccc1)NC] | 250 |
| 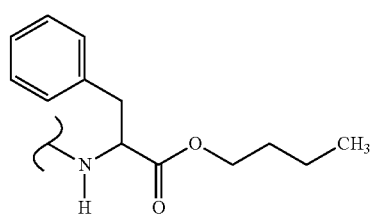 [SMILES: CCCCOC(=O)C(Cc1ccccc1)NC] | 251 |

TABLE 30.1-continued

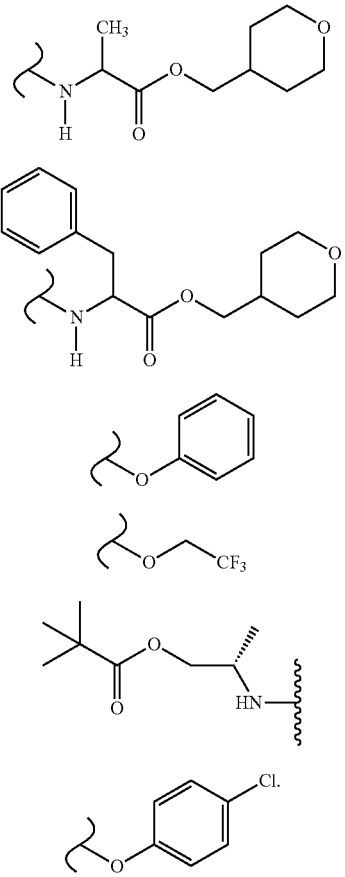

Embodiments of $R^x$ include esters, carbamates, carbonates, thioesters, amides, thioamides, and urea groups:

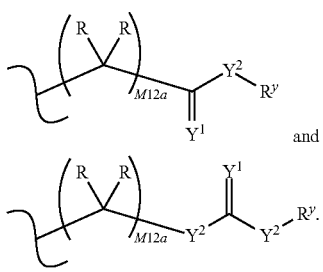

Any reference to the compounds of the invention described heerein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

The compounds of the invention, exemplified by Formula I-IV may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula I-IV may have a chiral phosphorus atom when $R^7$ is

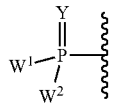

and $W^1$ and $W^2$ are different. When at least one of either $W^1$ or $W^2$ also has a chiral center, for example with $W^1$ or $W^2$ is a nitrogen-linked, chiral, naturally occurring α-amino acid ester, then the compound of Formula I-IV will exists as diastereomers because there are two centers of chirality in the molecule. All such diastereomers and their uses described herein are encompassed by the instant invention. Mixtures of diastereomers may be separate under high resolution analytical procedures such as electrophoresis, crystallization and/or chromatography. Diastereomeres may have different physical attributes such as, but not limited to, solubility, chemical stabilities and crystallinity and may also have different biological properties such as, but not limited to, enzymatic stability, absorption and metabolic stability.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "R" or "$R^1$", then it will be understood that the groups may be the same or different, i.e., each group is independently selected. Wavy lines, ⁓⁓⁓⁓, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Methods of Inhibition of a Paramyxoviridae Polymerase

Another aspect of the invention relates to methods of inhibiting the activity of Paramyxoviridae polymerase comprising the step of treating a sample suspected of containing Paramyxoviridae with a composition of the invention.

Compositions of the invention may act as inhibitors of Paramyxoviridae polymerase, as intermediates for such inhibitors or have other utilities as described below. The inhibitors will bind to locations on the surface or in a cavity of Paramyxoviridae polymerase having a geometry unique to Paramyxoviridae polymerase. Compositions binding Paramyxoviridae polymerase may bind with varying degrees of reversibility. Those compounds binding substantially irreversibly are ideal candidates for use in this method of the invention. Once labeled, the substantially irreversibly binding compositions are useful as probes for the detection of Paramyxoviridae polymerase. Accordingly, the invention relates to methods of detecting Paramyxoviridae polymerase in a sample suspected of containing Paramyxoviridae polymerase comprising the steps of: treating a sample suspected of containing Paramyxoviridae polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing Paramyxoviridae polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces Paramyxoviridae polymerase, frequently a pathogenic organism such as a Paramyxoviridae virus. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of Paramyxoviridae polymerase after application of the composition can be observed by any method including direct and indirect methods of detecting Paramyxoviridae polymerase activity. Quantitative, qualitative, and semiquantitative methods of determining Paramyxoviridae polymerase activity are all contemplated. Typically one of the screening methods described above are applied, however, any other method such as observation of the physiological properties of a living organism are also applicable.

Organisms that contain Paramyxoviridae polymerase include the Paramyxoviridae virus. The compounds of this invention are useful in the treatment or prophylaxis of Paramyxoviridae infections in animals or in man.

However, in screening compounds capable of inhibiting human Paramyxoviridae viruses, it should be kept in mind that the results of enzyme assays may not correlate with cell culture assays. Thus, a cell based assay should be the primary screening tool.

Screens for Paramyxoviridae Polymerase Inhibitors.

Compositions of the invention are screened for inhibitory activity against Paramyxoviridae polymerase by any of the conventional techniques for evaluating enzyme activity. Within the context of the invention, typically compositions are first screened for inhibition of Paramyxoviridae polymerase in vitro and compositions showing inhibitory activity are then screened for activity in vivo. Compositions having in vitro Ki (inhibitory constants) of less then about $5\times10^{-6}$ M and preferably less than about $1\times10^{-7}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Paramyxoviridae infections as described below.

In another aspect, the invention is a novel, efficacious, safe, nonirritating and physiologically compatible inhalable composition comprising a compound of Formula I-IV, or a pharmaceutically acceptable salt thereof, suitable for treating Paramyxoviridae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 µm. Preferably, the compound of Formula I-IV is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 µm and about 5 µm using a nebulizer able to aerosolize the formulation of the compound of Formula I-IV into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µm, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method of the invention, the aerosol formulation for nebulization delivers a therapeutically efficacious dose of the compound of Formula I-IV to the site of Paramyxoviridae infection sufficient to treat the Paramyxoviridae infection. The amount of drug administered must be adjusted to reflect the efficiency of the delivery of a therapeutically efficacious dose of the compound of Formula I-IV. In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formula I-IV into the airways. In a preferred embodiment, at least about 30 to about 50% of the active compound is delivered. More preferably, about 70 to about 90% of the active compound is delivered.

In another embodiment of the instant invention, a compound of Formula I-IV or a pharmaceutically acceptable salt thereof, is delivered as a dry inhalable powder. The compounds of the invention are administered endobronchially as a dry powder formulation to efficacious deliver fine particles of compound into the endobronchial space using dry powder or metered dose inhalers. For delivery by DPI, the compound of Formula I-IV is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well know in the art. In one embodiment, excipients are added to the compound of Formula I-IV before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formula I-IV is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm, and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formula I-IV, or a pharmaceutically acceptable salt thereof, is delivered as a dry powder using either type of dry powder inhaler as described herein, wherein the MMAD of the dry powder, exclusive of any excipients, is predominantly in the range of 1 µm to about 5 µm.

In another preferred embodiment, a compound of Formula I-IV is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In preferred embodiments, a compound of Formula I-IV, or a pharmaceutically acceptable salt thereof, is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. For the treatment of Paramyxoviridae virus infections, preferably, the other active therapeutic agent is active against Paramyxoviridae virus infections, particularly respiratory syncytial virus infections and/or parainfluenza virus infections. Non-limiting examples of these other active therapeutic agents are ribavirin, palivizumab, motavizumab, RSV-IGIV (RespiGam®), MEDI-557, A-60444, MDT-637, BMS-433771, and mixtures thereof.

Many of the infections of the Paramyxoviridae viruses are respiratory infections. Therefore, additional active therapeutics used to treat respiratory symptoms and sequelae of infection may be used in combination with the compounds of Formula I-IV. The additional agents are preferably administered orally or by direct inhalation. For example, other preferred additional therapeutic agents in combination with the compounds of Formula I-IV for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formula I-IV are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflammatory agents working through anti-inflammatory cascade mechanisms are also useful as additional therapeutic agents in combination with the compounds of Formula I-IV for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast);

4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethyl amino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of Formula I-IV are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formula I-IV are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formula I-IV for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of Formula I-IV may also be combined with mucolytic agents to treat both the infection and symptoms of respiratory infections. A non-limiting example of a mucolytic agent is ambroxol. Similarly, the compounds of Formula I-IV may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). The compounds of Formula I-IV may also be combined with nebulized hypertonic saline particularly when the Paramyxoviridae virus infection is complicated with bronchiolitis. The combination of the compounds of Formula I-IV with hypertonic saline may also comprise any of the additional agents discussed above. In a preferred aspect, nebulized about 3% hypertonic saline is used.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting Paramyxoviridae polymerase in a cell, comprising: contacting a cell infected with HCV with an effective amount of a compound of Formula I-IV, or a pharmaceutically acceptable salt, solvate, and/or ester thereof, whereby Paramyxoviridae polymerase is inhibited.

In still yet another embodiment, the present application provides for methods of inhibiting Paramyxoviridae polymerase in a cell, comprising: contacting a cell infected with HCV with an effective amount of a compound of Formula I-IV, or a pharmaceutically acceptable salt, solvate, and/or ester thereof, and at least one additional active therapeutic agent, whereby Paramyxoviridae polymerase is inhibited.

In still yet another embodiment, the present application provides for methods of inhibiting Paramyxoviridae polymerase in a cell, comprising: contacting a cell infected with Paramyxoviridae virus with an effective amount of a compound of Formula I-IV, or a pharmaceutically acceptable salt, solvate, and/or ester thereof, and at least one additional active therapeutic agent selected In still yet another embodiment, the present application provides for methods of treating Paramyxoviridae virus infection in a patient, comprising: administering to the patient a therapeutically effective amount of a compound of Formula I-IV, or a pharmaceutically acceptable salt, solvate, and/or ester thereof.

In still yet another embodiment, the present application provides for methods of treating Paramyxoviridae virus infection in a patient, comprising: administering to the patient a therapeutically effective amount of a compound of Formula I-IV, or a pharmaceutically acceptable salt, solvate, and/or ester thereof, and at least one additional active therapeutic agent, whereby Paramyxoviridae polymerase is inhibited.

In still yet another embodiment, the present application provides for methods of treating Paramyxoviridae virus infection in a patient, comprising: administering to the patient a therapeutically effective amount of a compound of Formula I-IV, or a pharmaceutically acceptable salt, solvate, and/or ester thereof, and at least one additional active therapeutic agent.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| Ac$_2$O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |

TABLE 1-continued

List of abbreviations and acronyms.

| Abbreviation | Meaning |
| --- | --- |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH+ | mass plus 1 |
| MH− | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

Preparation of Compounds (2S)-ethyl 2-(chloro(phenoxy)phosphorylamino)propanoate (Chloridate A

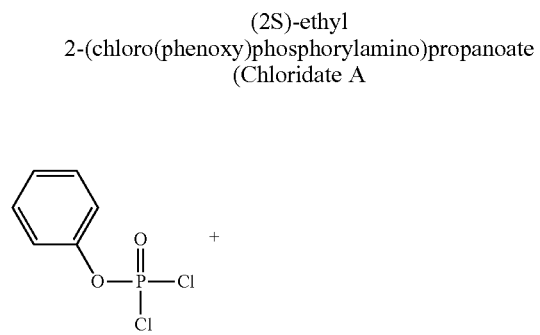

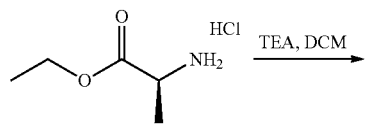

-continued

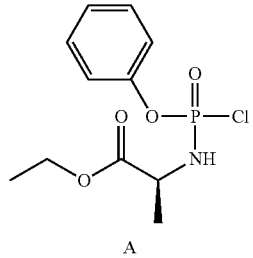

A

Ethyl alanine ester hydrochloride salt (1.69 g, 11 mmol) was dissolved in anhydrous $CH_2Cl_2$ (10 mL) and the mixture stirred with cooling to 0° C. under $N_2(g)$. Phenyl dichlorophosphate (1.49 mL, 10 mmol) was added followed by dropwise addition of $Et_3N$ over 10 min. The reaction mixture was then slowly warmed to RT and stirred for 12 h. Anhydrous $Et_2O$ (50 mL) was added and the mixture stirred for 30 min. The solid that formed was removed by filtration, and the filtrate concentrated under reduced pressure. The residue was subjected to silica gel chromatography eluting with 0-50% EtOAc in hexanes to provide intermediate A (1.13 g, 39%).

$^1$H NMR (300 MHz, $CDCl_3$) δ 7.39-7.27 (m, 5H), 4.27 (m, 3H), 1.52 (m, 3H), 1.32 (m, 3H).

$^{31}$P NMR (121.4 MHz, $CDCl_3$) δ 8.2, 7.8.

(2S)-2-ethylbutyl 2-(chloro(phenoxy)phosphorylamino)propanoate (Chloridate B

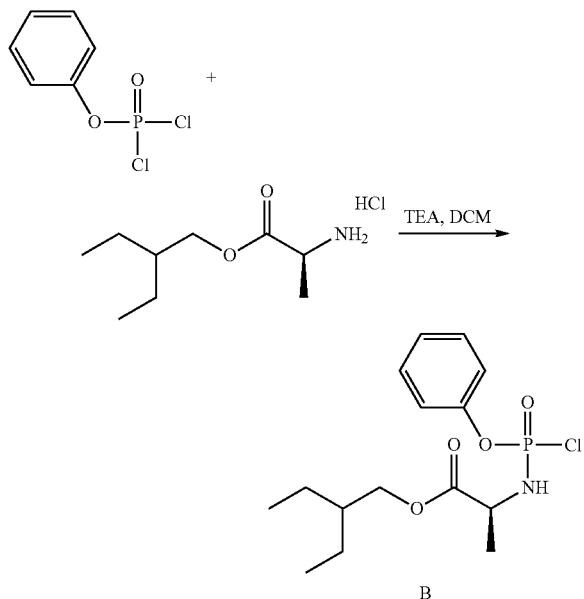

The 2-ethylbutyl alanine chlorophosphoramidate ester B was prepared using the same procedure as chloridate A except substituting 2-ethylbutyl alanine ester for ethyl alanine ester. The material is used crude in the next reaction. Treatment with methanol or ethanol forms the displaced product with the requisite LCMS signal.

(2S)-isopropyl 2-(chloro(phenoxy)phosphorylamino)propanoate (Chloridate C

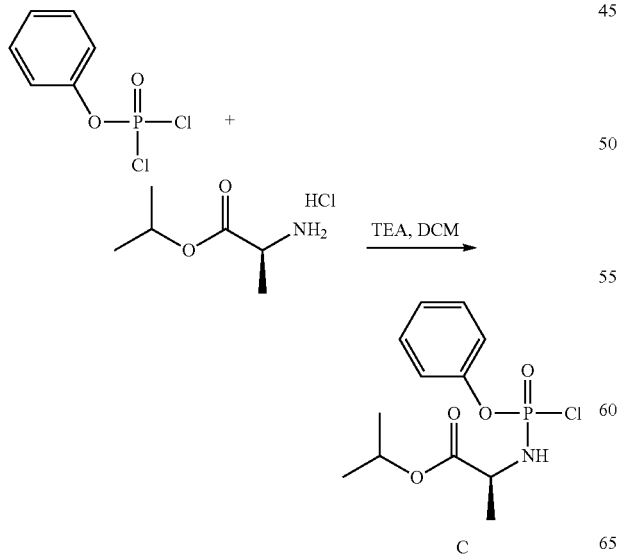

The isopropyl alanine chlorophosphoramidate ester C was prepared using the same procedure as chloridate A except substituting isopropyl alanine ester for the ethyl alanine ester. The material is used crude in the next reaction. Treatment with methanol or ethanol forms the displaced product with the requisite LCMS signal.

(2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile (Compound 1)

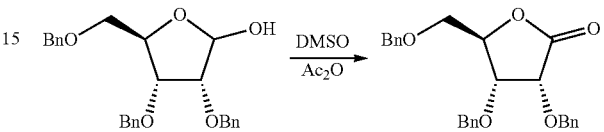

The commercially available lactol (10 g, 23.8 mmol) was dissolved in anhydrous DMSO (30 mL) under $N_2$(g). $Ac_2O$ (20 mL) was added and the resultant reaction mixture stirred at RT for 48 h. The reaction mixture was poured onto ice $H_2O$ (500 mL) and the mixture stirred for 20 min. The mixture was extracted with EtOAc (3×200 mL) and the combined organic extracts were then washed with $H_2O$ (3×200 mL). The organic extract was dried over anhydrous $MgSO_4$, filtered and concentrated under reduced pressure. The residue was dissolved in $CH_2Cl_2$ and subjected to silica gel chromatography eluting with 25% EtOAc in hexanes to provide the lactone (9.55 g, 96%).

$^1$H NMR (400 MHz, DMSO) δ☐☐ 7.30-7.34 (m, 13H), 7.19-7.21 (m, 2H), 4.55-4.72 (m, 6H), 4.47 (s, 2H), 4.28 (d, J=3.9 Hz, 1H), 3.66 (m, 2H).

LCMS m/z 436.1 [M+$H_2O$], 435.2 [M+OH]– Tr=2.82 min

HPLC Tr=4.59 [2-98% ACN in H2) over 5 min @2 ml/min flow.

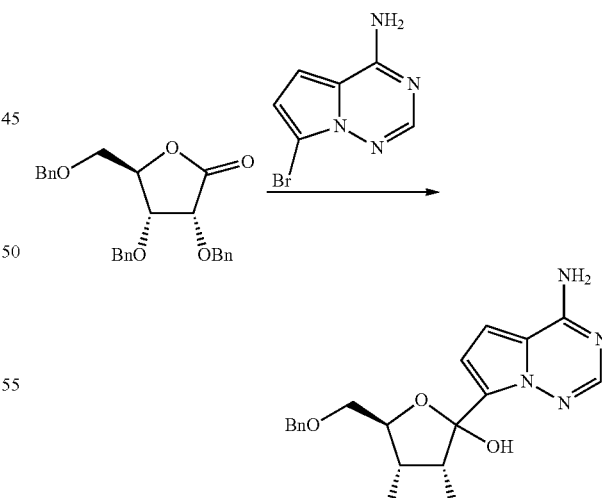

The bromopyrazole (prepared according to WO2009/132135) (0.5 g, 2.4 mmol) was suspended in anhydrous THF (10 mL) under $N_2$(g). The suspension was stirred and TMSCl (0.67 mL, 5.28 mmol) was added. The mixture was stirred for 20 min. at RT and then cooled to −78° C. after which time a solution of n-BuLi (6 mL, 1.6 N in hexanes, 9.6 mmol) was added slowly. The reaction mixture was stirred for 10 min. at −78° C. and then the lactone (1 g, 2.4 mmol) was added via syringe. When the reaction was complete as measured by LCMS, AcOH was added to quench the reaction. The mixture was concentrated under reduced pressure and the residue dissolved in a mixture of CH$_2$Cl$_2$ and H$_2$O (100 mL, 1:1). The organic layer was separated and washed with H$_2$O (50 mL). The organic layer was then dried over anhydrous MgSO$_4$, filtered and concentrated under reduced pressure. The residue was subjected to silica gel chromatography eluting with 0-50% EtOAc in hexanes to provide the product as a 1:1 mixture of anomers (345 mg, 26% yield).

LCMS m/z 553 [M+H].

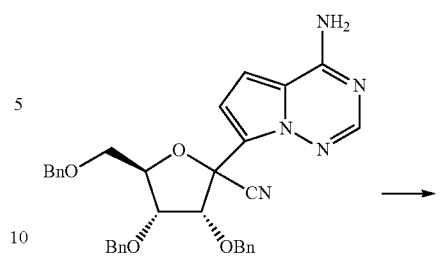

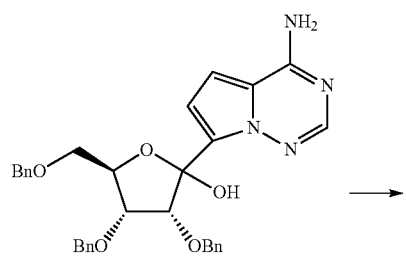

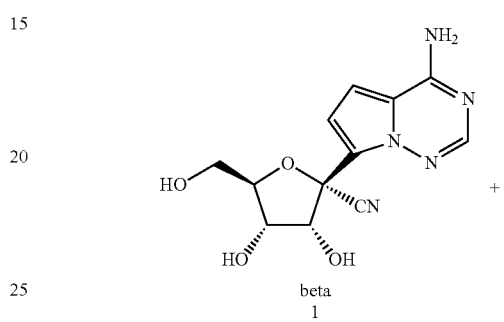

The hydroxy nucleoside (1.1 g, 2.0 mmol) was dissolved in anhydrous CH$_2$Cl$_2$ (40 mL) and the solution cooled with stirring to 0° C. under N$_2$(g). TMSCN (0.931 mL, 7 mmol) was added and the mixture stirred for a further 10 min. TMSOTf (1.63 mL, 9.0 mmol) was slowly added to the reaction and the mixture stirred for 1 h. The reaction mixture was then diluted with CH$_2$Cl$_2$ (120 mL) and aqueous NaHCO$_3$ (120 mL) was added to quench the reaction. The reaction mixture was stirred for a further 10 min and the organic layer separated. The aqueous layer was extracted with CH$_2$Cl$_2$ (150 mL) and the combined organic extracts dried over anhydrous MgSO$_4$, filtered and concentrated under reduced pressure. The residue was dissolved in a minimal amount of CH$_2$Cl$_2$ and subjected to silica gel chromatography eluting with a gradient of 0-75% EtOAc and hexanes to provide the tribenzyl cyano nucleoside as a mixture of anomers. (0.9 g, 80%).

$^1$H NMR (300 MHz, CD$_3$CN) δ 7.94 (s, 0.5H), 7.88 (s, 0.5H), 7.29-7.43 (m, 13H), 7.11-7.19 (m, 1H), 6.82-6.88 (m, 1H), 6.70-6.76 (m, 1H), 6.41 (bs, 2H), 5.10 (d, J=3.9 Hz, 0.5H), 4.96 (d, J=5.1 Hz, 0.5H), 4.31-4.85 (m, 7H), 4.09-4.18 (m, 2H), 3.61-3.90 (m, 2H).

LCMS m/z 562 [M+H].

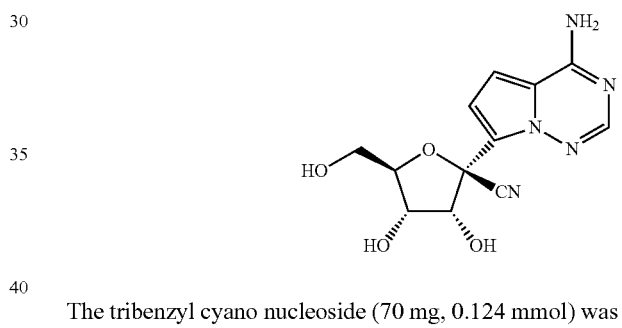

The tribenzyl cyano nucleoside (70 mg, 0.124 mmol) was dissolved in anhydrous CH$_2$Cl$_2$ (2 mL) and cooled to −78° C. under N$_2$(g). A solution of BCl$_3$ (1N in CH$_2$Cl$_2$, 0.506 mL, 0.506 mmol) was added and the reaction mixture stirred for 1 h. at −78° C. When the reaction was complete by LC/MS, MeOH was added to quench the reaction. The reaction mixture was allowed to warm to room RT and the solvent removed under reduced pressure. The residue was subjected to C18 reverse phase HPLC, eluting for 5 min with H$_2$O (0.1% TFA), followed by a gradient of 0-70% MeCN in H$_2$O (0.1% TFA) over 35 min, to elute the α-anomer (20 mg, 37%), and β-anomer 1 (20 mg, 37%).

(α-anomer)

$^1$H NMR (300 MHz, D$_2$O) δ 7.96 (s, 1H), 7.20 (d, J=4.8 Hz, 1H), 6.91 (d, J=4.8 Hz, 1H), 4.97 (d, J=4.4 Hz, 1H), 4.56-4.62 (m, 1H), 4.08-4.14 (m, 1H), 3.90 (dd, J=12.9, 2.4 Hz, 1H), 3.70 (dd, J=13.2, 4.5 Hz, 1H).

(β-anomer)

$^1$H NMR (400 MHz, DMSO) δ 7.91 (s, 1H), 7.80-8.00 (br s, 2H), 6.85-6.89 (m, 2H), 6.07 (d, J=6.0 Hz, 1H), 5.17 (br s, 1H), 4.90 (br s, 1H), 4.63 (t, J=3.9 Hz, 1H), 4.02-4.06 (m, 1H), 3.94 (br s, 1H), 3.48-3.64 (m, 2H).

LCMS m/z 292.2 [M+H], 290.0 [M−H]. Tr=0.35 min.

13C NMR (400 MHZ, DMSO), 156.0, 148.3, 124.3, 117.8, 117.0, 111.2, 101.3, 85.8, 79.0, 74.7, 70.5, 61.4

HPLC Tr=1.32 min

(2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile (Compound 2)

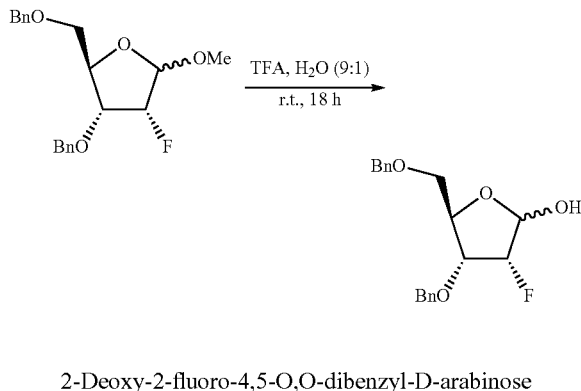

2-Deoxy-2-fluoro-4,5-O,O-dibenzyl-D-arabinose

1′-Methoxy-2-deoxy-2-fluoro-4,5-O,O-dibenzyl-D-arabinose (1.0 g, 2.88 mmol) in TFA (13.5 mL) was treated with H$_2$O (1.5 mL) and the resultant mixture stirred for 5 h. The mixture was then diluted with EtOAc (100 mL) and treated with saturated NaHCO$_3$ (50 mL). The organic layer was separated and washed with NaCl (50 mL), dried over anhydrous MgSO$_4$, filtered and concentrated under reduced pressure. The residue was subjected to silica gel chromatography (80 g SiO$_2$ Combiflash HP Gold Column) eluting with 0-100% EtOAc in hexanes to afford 2-deoxy-2-fluoro-4,5-O,O-dibenzyl-D-arabinose (695 mg, 72%) as a white solid: R$_f$=0.52 (25% EtOAc in hexanes);

$^1$H NMR (300 MHz, CDCl$_3$) δ 7.30 (m, 10H), 5.35 (m, 1H), 4.68-4.29 (m, 7H), 3.70 (d, J=10.5 Hz, 1H), 3.50 (d, J=10.5 Hz, 2H).
$^{19}$F NMR (282.2 MHz, CDCl$_3$) δ −207 (m), −211 (m).
LCMS m/z 350 [M+H$_2$O].

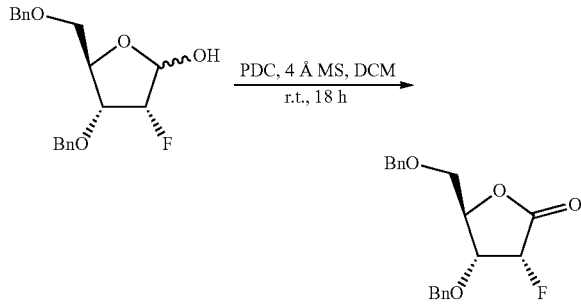

(3R,4R,5R)-4-(benzyloxy)-5-(benzyloxymethyl)-3-fluorodihydrofuran-2(3H)-one

2-Deoxy-2-fluoro-4,5-O,O-dibenzyl-D-arabinose (4.3 g, 12.8 mmol) was dissolved in CH$_2$Cl$_2$ (85 mL) was treated with 4 Å MS (10 g) and pyridinium dichromate (14.4 g, 38.3 mmol). The resultant mixture was stirred for 24 h and then filtered through a pad of Celite. The eluant was concentrated under reduced pressure and the residue subjected to silica gel chromatography (120 g SiO$_2$ HP Gold Combiflash Column) eluting with 0-100% EtOAc in hexanes to afford (3R,4R,5R)-4-(benzyloxy)-5-(benzyloxymethyl)-3-fluorodihydrofuran-2(3H)-one as a clear oil (3.5 g, 83%): R$_f$=0.25 (25% EtOAc in hexanes).

$^1$H NMR (300 MHz, CDCl$_3$) δ 7.37 (m, 10H), 5.45 (dd, J=49, 5.7, Hz, 1H), 4.85 (d, J=11.7 Hz, 1H), 4.52 (m, 4H), 4.29 (d, J=5.4 Hz, 1H), 2.08 (dd, J=15.3, 10.2 Hz, 2H).
$^{19}$F NMR (282.2 MHz, CDCl$_3$) δ −216.
LCMS m/z 348 [M+H$_2$O].
HPLC (6-98% MeCN—H$_2$O gradient, 0.05% TFA modifier) t$_R$=5.29 min.
Phenomenex Synergi 4 m Hydro-RP 80 A, 50×4.60 mm, 4 micron; 2 mL/min flow rate

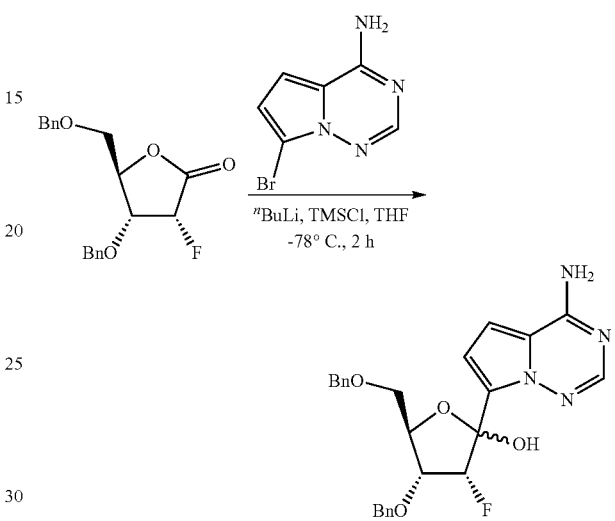

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol 7-Bromopyrrolo[1,2-f][1,2,4]-triazin-4-amine (68 mg, 0.319 mmol) in THF (1.4 mL) was treated with TMSCl (89 µL, 0.703 mmol) and the mixture stirred for 2 h. The mixture was then cooled to −78° C. and treated with nBuLi (1.0 M in hexanes, 1.09 mL, 1.09 mmol). The solution was stirred for 30 min and then treated with (3R,4R,5R)-4-(benzyloxy)-5-(benzyloxymethyl)-3-fluorodihydrofuran-2(3H)-one (106 mg, 0.319 mmol) dropwise in THF (1.4 mL). The resultant mixture was stirred for 30 min and then AcOH (83 µL, 1.44 mmol) in THF (1.0 mL) was added to quench the reaction. The mixture was warmed to RT and then concentrated under reduced pressure. The residue was diluted with EtOAc (100 mL) and washed with saturated NaCl solution (50 mL). The organic layer was dried over anhydrous MgSO$_4$, filtered and concentrated under reduced pressure. The residue was subjected to silica gel chromatography (40 g SiO$_2$ HP Gold Combiflash Column) eluting with 0-100% EtOAc in hexanes followed by a 0-100% gradient of (20% MeOH in EtOAc) in EtOAc to afford (3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol as a white solid (68 mg, 44%, 60/40 mixture of α/β isomers). R$_f$=0.32 (EtOAc).

$^1$H NMR (300 MHz, CDCl$_3$) δ 8.05 (s, 1H), 7.86 (s, 1H), 7.81 (s, 1H), 7.64 (s, 1H), 7.26 (m, 10H), 6.95 (m, 1H), 6.71 (m, 1H), 6.08 (m, 1H), 5.34 (m, 1H), 4.65 (m, 6H), 4.71 (m, 2H).
$^{19}$F NMR (282.2 MHz, CDCl$_3$) δ −211 (m).
LCMS m/z 465 [M+H].
HPLC (6-98% MeCN—H$_2$O gradient, 0.05% TFA modifier) t$_R$=4.37 min. (α-isomer), 4.54 min. (β-isomer).

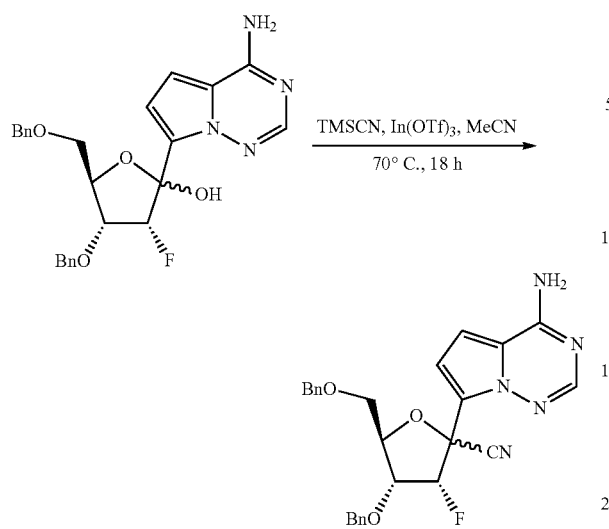

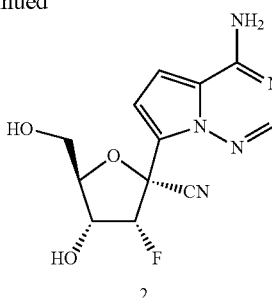

(2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile (2)

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile (110 mg, 0.23 mmol) was dissolved in $CH_2Cl_2$ (1.5 mL) and cooled to 0° C. The reaction mixture was treated with $BCl_3$ (1.0 M in $CH_2Cl_2$, 766 µL, 0.77 mmol) and stirred for 2 h. The mixture was then cooled to −78° C. and treated with $Et_3N$ (340 µL, 2.44 mmol) followed by MeOH (2 mL) before allowing to warm to RT. The reaction was concentrated under reduced pressure and then co-evaporated with MeOH (3×5 mL). The residue was then suspended in $H_2O$ (5 mL) and treated with $NaHCO_3$ (1 g). The solution was stirred for 10 min and then concentrated under reduced pressure. The residue was filtered and washed with MeOH (3×10 mL) on a fritted glass funnel (coarse) and the eluant concentrated under reduced pressure. The residue was subjected to reverse phase HPLC (6-98% MeCN in $H_2O$ gradient with 0.05% TFA modifier) to afford (2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile 2 as a white solid (16.8 mg, 25%) and the α-isomer.

Data for the β-isomer: $R_f$=0.13 (10% MeOH in EtOAc).

$^1H$ NMR (300 MHz, $CD_3OD$) δ 8.09 (s, 1H), 7.28 (d, J=5.1 Hz, 1H), 7.17 (d, J=5.1 Hz, 1H), 5.42 (dd, J=53, 3.3 Hz, 1H), 4.20 (m, 2H), 3.99 (d, J=3.6 Hz, 1H), 3.77 (d, J=3.6 Hz, 1H).

$^{19}F$ NMR (282.2 MHz, $CDCl_3$) δ −197 (m).

LCMS m/z 294 [M+H].

HPLC (2-98% MeCN—$H_2O$ gradient, 0.05% TFA modifier) $t_R$=1.49 min.

(2R,3R,4R,5S)-5-(4-aminopyrrolo[1,2-f][1,2,4]triazin-7-yl)-4-fluoro-2-(hydroxymethyl)-5-methyltetrahydrofuran-3-ol (Compound 3)

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile (3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol (195 mg, 0.42 mmol) was dissolved in MeCN (1.4 mL) was treated with TMSCN (336 µL, 2.52 mmol) and $In(OTf)_3$ (708 mg, 1.26 mmol). The solution was stirred at 70° C. for 18 h and then cooled to 0° C. The mixture was treated with saturated $NaHCO_3$ solution (20 drops) then warmed to RT and diluted with EtOAc (100 mL) and $H_2O$ (50 mL). The organic layer was separated and washed with saturated NaCl solution (50 mL), dried over $MgSO_4$, filtered and concentrated under reduced pressure. The residue was subjected to silica gel chromatography (40 g $SiO_2$ HP Gold Combiflash Column) eluting with 0-100% EtOAc in hexanes to afford (3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile as a white solid (110 mg, 55%, 60/40 mixture of α/β isomers). Data for both isomers: $R_f$=0.53 (EtOAc).

$^1H$ NMR (300 MHz, $CDCl_3$) δ 8.01 (s, 1H), 7.94 (s, 1H), 7.30 (m, 10H), 7.00 (d, J=4.5 Hz, 1H), 6.93 (d, J=4.8 Hz, 1H), 6.87 (d, J=5.4 Hz, 1H), 6.70 (d, J=4.8 Hz, 1H), 5.85 (dd, J=52, 3.3 Hz, 1H), 5.55 (dd, J=53, 4.5 Hz, 1H), 4.71 (m, 7H), 3.87 (m, 2H), 3.72 (m, 2H).

$^{19}F$ NMR (282.2 MHz, $CDCl_3$) δ −196 (m), 203 (m).

LCMS m/z 474 [M+H].

HPLC (6-98% MeCN—$H_2O$ gradient, 0.05% TFA modifier) $t_R$=4.98 min.

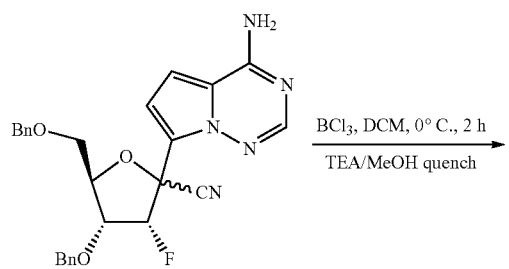

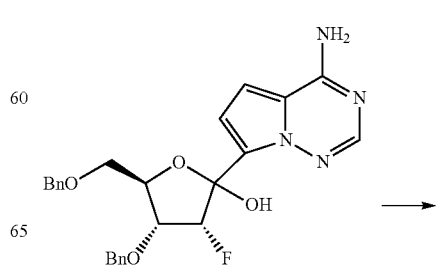

-continued

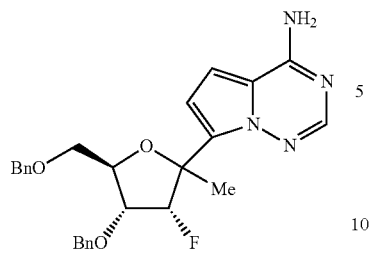

The starting nucleoside (prepared as described in the synthesis of compound 2) (0.355 g, 0.765 mmol) was dissolved in anhydrous THF (35 mL) and cooled to 0° C. with stirring under $N_2(g)$. A solution of methyl magnesium chloride (2 mL, 6 mmol) (3N in THF) was added and the resultant mixture stirred overnight. Acetic acid (7 mmol) was added to quench the reaction and then the solvents were removed by rotory under reduced pressure. The residue was re-dissolved in $CH_2Cl_2$ and the solution subjected to a plug of silica gel to isolate the product (0.355 g) as a crude mixture. LC/MS (m/z: 480, M$^{+1}$). The crude material was dissolved in anhydrous $CH_2Cl_2$ (20 mL) and placed under $N_2(g)$. The solution was stirred and treated with methanesulfonic acid (0.2 mL, 2.74 mmol). The reaction mixture was stirred for 12 h at RT and then quenched by the addition of $Et_3N$ (3.5 mmol). The mixture was concentrated under reduced pressure and the residue subjected to silica gel chromatography to provide the methyl substituted nucleoside (0.174 g, 0.377 mmol, 44% yield) as a 4:1 mixture of beta- and alpha-anomers respectively.

$^1$H NMR (300 MHz, CD$_3$CN) major anomer δ 7.87 (s, 1H), 7.27-7.40 (m, 10H), 6.77 (d, J=4.5 HZ, 1H), 6.70 (d, J=4.5 Hz, 1H), 6.23 (br s, 2H), 5.53 (dd, J=55, 3.3 Hz, 1H), 4.42-4.75 (m, 4H), 4.19-4.26 (m, 1H), 3.65-4.00 (m, 3H), 1.74 (d, J=3.9 Hz, 3H).

$^{19}$F NMR (282.2 MHz, CD$_3$CN) major anomer δ −207 (m, 1F)

LCMS m/z 463 [M+H].

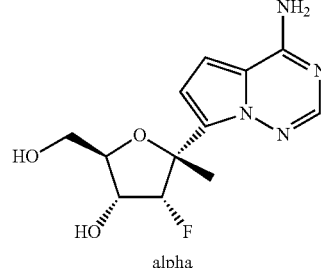

alpha

The benzylated nucleoside material (0.134 g, 0.290 mmol), Degussa catalyst (0.268 g) and AcOH (30 mL) were mixed together. The reaction atmosphere was charged with H$_2$ (g) and the reaction stirred for 2 h. The catalyst was removed by filtration and the mixture concentrated under reduced pressure. The residue was dissolved in a minimal amount of H$_2$O and subjected to reverse phase HPLC (C$^{18}$ hydro RP column) to isolate the β-anomer 3 (0.086 g, 0.217 mmol, 57% yield).

$^1$H NMR (300 MHz, D$_2$O) δ 7.87 (s, 1H), 7.22 (d, J=4.8 Hz, 1H), 6.87 (d, J=4.8 Hz, 1H), 5.35 (dd, J=54, 3.6 Hz, 1H), 3.97-4.10 (m, 2H), 3.81 (dd, J=12.6, 2.1 Hz, 1H), 3.64 (dd, J=12.6, 4.8 Hz, 1H), 1.65 (d, J=4.2 Hz, 3H).

$^{19}$F NMR (282.2 MHz, CD$_3$CN) δ −207 (m, 1F).

A small amount of alpha anomer was characterized as follows.

$^1$H NMR (300 MHz, D$_2$O) δ 7.86 (s, 1H), 7.26 (d, J=4.8 Hz, 1H), 6.85 (d, J=4.8 Hz, 1H), 5.31 (dd, J=54, 3.9 Hz, 1H), 4.39 (ddd, J=26.1, 9.9, 3.6 Hz, 2H), 4.00-4.05 (m, 1H), 3.90 (dd, J=12.3, 2.1 Hz, 1H), 3.66 (dd, J=12.6, 4.8, 1H), 1.56 (s, 3H).

$^{19}$F NMR (282.2 MHz, CD$_3$CN) δ −198 (dd, J=54, 26 Hz, 1F).

(2R)-isopropyl 2-((((2R,3R,4R,5S)-5-(4-aminopyrrolo[1,2-f][1,2,4]triazin-7-yl)-4-fluoro-3-hydroxy-5-methyltetrahydrofuran-2-yl)methoxy)-(phenoxy)phosphorylamino)propanoate (Compound 4)

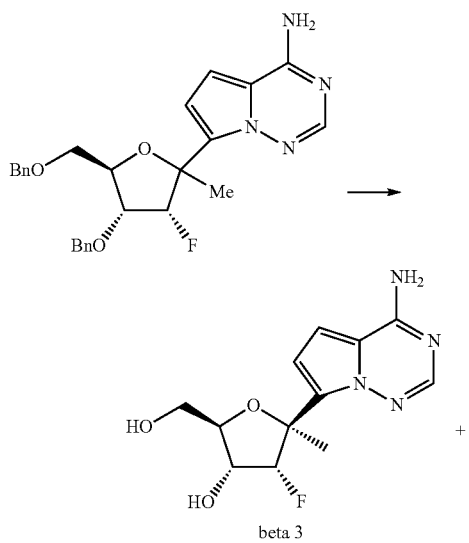

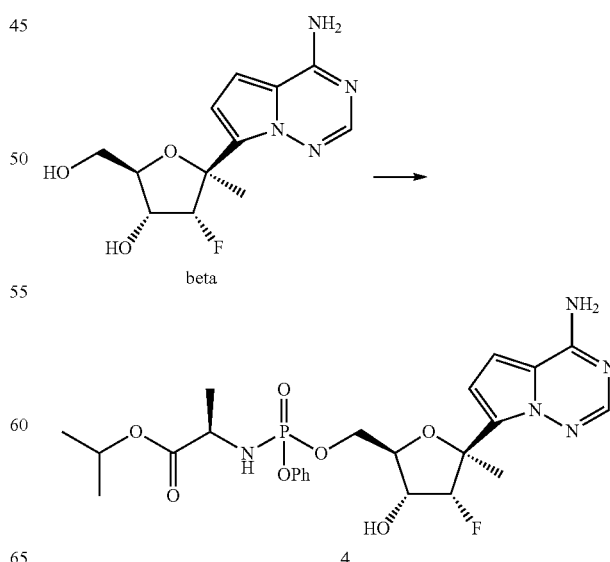

The nucleoside 3 (0.011 g, 0.04 mmol) was dissolved in trimethylphosphate (2 mL) and cooled to 0° C. The mixture was stirred under an atmosphere of N₂(g) and 1-Methylimidazole (0.320 mL, 5 mmol) followed by the alaninylmonoisopropyl, monophenol phosphorchloridate C (0.240 mL, 4.4 mmol) was added. The reaction mixture was stirred for 2 h. at 0° C. and then allowed to warm slowly to RT. while monitoring by LC/MS. When complete by LCMS, the reaction mixture was treated with H₂O (5 mL) and then concentrated under reduced pressure. The residue was dissolved in CH₂Cl₂ and subjected to silica gel chromatography eluting with 0-100% EtOAc in hexanes. The product fractions were collected and concentrated. The residue was subjected to prep HPLC to yield the alanine isopropyl monoamidate prodrug 4 as a mixture of isomers (4.7 mg, 0.003 mmol, 6%).

$^1$H NMR (300 MHz, CD3CN) δ 7.87 (s, 1H), 7.17-7.44 (m, 5H), 6.71-6.83 (m, 2H), 6.14 (br, s, 2H), 5.38 (dd, J=56, 3.3 Hz, 1H), 4.92-5.01 (m, 1H), 3.86-4.46 (m, 6H), 3.58 (m, 1H), 1.73 (m, 3H), 1.18-1.34 (m, 9H)

LCMS m/z 552 [M+H].

(2R)-ethyl 2-((((2R,3R,4R,5S)-5-(4-aminopyrrolo[1,2-f][1,2,4]triazin-7-yl)-4-fluoro-3-hydroxy-5-methyltetrahydrofuran-2-yl)methoxy)(phenoxy)phosphorylamino)propanoate (Compound 5)

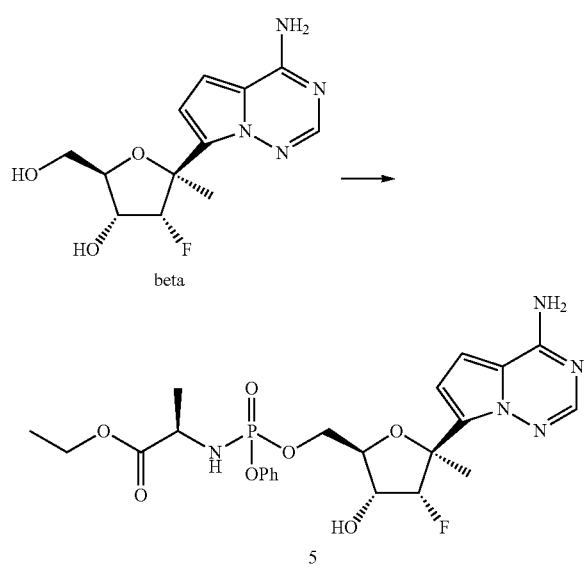

The nucleoside 3 (0.026 g, 0.092 mmol) was dissolved in trimethylphosphate (2 mL) and cooled to 0° C. The mixture was stirred under N₂(g) and 1-methylimidazole (0.062 mL, 0.763 mmol) followed by the chloridate A (0.160 g, 0.552 mmol) were added. The reaction mixture was stirred for 2 h. at 0° C. and then allowed to warm slowly to RT. H₂O (5 mL) was added to quench the reaction and then the mixture concentrated under reduced pressure. The residue was dissolved in CH₂Cl₂ and subjected to silica gel chromatography eluting with 0-100% EtOAc in hexanes. The product fractions were collected and concentrated. Crude product was eluted using 0 to 100 percent EtOAc in hexanes. The crude product was collected and concentrated under reduced pressure. The residue was subjected to prep HPLC to yield 5 (2.0 mg, 4% yield).

LCMS m/z 538 [M+H].

((2R,3R,4R,5S)-5-(4-aminopyrrolo[1,2-f][1,2,4]triazin-7-yl)-4-fluoro-3-hydroxy-5-methyltetrahydrofuran-2-yl)methyl tetrahydrogen triphosphate (Compound 6)

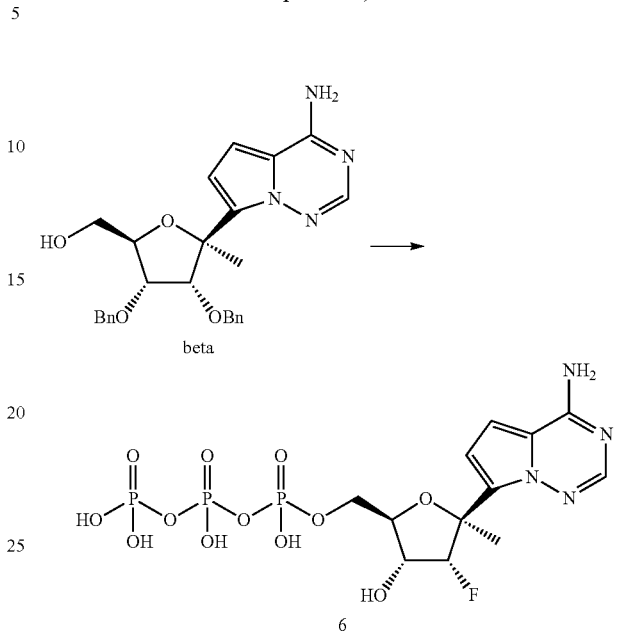

The nucleoside 3 (0.022 g, 0.056 mmol) was dissolved in trimethylphosphate (1 mL) and stirred under N₂(g). Phosphorous oxychloride (0.067 mL, 0.73 mmol) was added and the mixture stirred for 2 h. Monitoring by analytical ion-exchange column determined the time at which >80 percent of monophosphate was formed. A solution of tributylamine (0.44 mL, 1.85 mmol) and triethylammonium pyrophosphate (0.327 g, 0.72 mmol) dissolved in anhydrous DMF (1 mL) was added. The reaction mixture was stirred for 20 min and then quenched by the addition of 1N triethylammonium bicarbonate solution in H₂O (5 mL). The mixture was concentrated under reduced pressure and the residue re-dissolved in H₂O. The solution was subjected to ion exchange chromatography to yield the title product 6 (1.7 mg, 6% yield).

LCMS m/z 521 [M−H]. Tr=0.41
HPLC ion exchange TR=9.40 min (2R,3R,5S)-2-(4-aminopyrrolo[1,2-f][1,2,4]triazin-7-yl)-3-hydroxy-5-(hydroxymethyl)-tetrahydrofuran-2-carbonitrile (Compound 7)

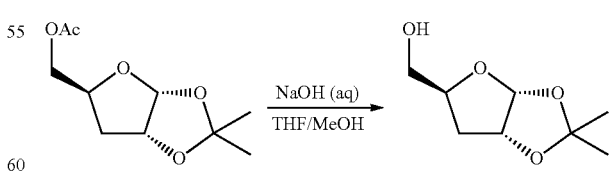

((3αR,5S,6αR)-2,2-dimethyl-tetrahydrofuro[2,3-d][1,3]dioxol-5-yl)methanol

The acetate material (1.2 g, 5.5 mmol) (J. Org. Chem. 1985, 50, 3547, De Bernardo et al) was dissolved in a 1:1 mixture MeOH and THF (10 mL). A 1N solution of NaOH (aq) (10 mL) was added until the pH was 13. The reaction mixture was stirred for 2 h and then neutralized to pH 8-9 by the addition of AcOH. The mixture was extracted with EtOAc (10×30 mL) and the combined organic extracts dried over anhydrous Na$_2$SO$_4$, filtered and concentrated under reduced pressure. The residue was subjected to silica gel chromatography eluting with 0-70% EtOAc in hexanes to give the desired product (866 mg, 90%).

$^1$H NMR (300 MHz, CDCl$_3$) δ 5.84 (d, J=3.6 Hz, 1H), 4.78 (t, J=4.5 Hz, 1H), 4.38 (m, 1H), 3.93-3.54 (m, 2H), 2.04-1.84 (m, 2H), 1.52 (s, 3H), 1.33 (s, 3H).

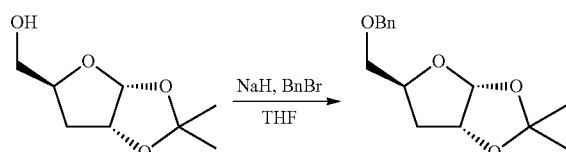

(3αR,5S,6αR)-5-(benzyloxymethyl)-2,2-dimethyl-tetrahydrofuro[2,3-d][1,3]dioxole

Sodium hydride (188 mg, 7.46 mmol) was dissolved in anhydrous THF (5 mL) and stirred under N$_2$(g) at RT. The alcohol (866 mg, 4.97 mmol) was dissolved in anhydrous THF (3 mL) and then added in portions over 5 min. to the sodium hydride mixture. The resultant mixture was stirred for 20 min. and then benzyl bromide (892 μL, 7.46 mmol) was added. The reaction was stirred for 2 h and then poured onto a mixture of ice cold aqueous NaHCO$_3$ and EtOAc (30 mL). The organic layer was separated and then the aqueous layer re-extracted with EtOAc (30 mL). The combined organic extracts were dried over anhydrous Na$_2$SO$_4$, filtered and concentrated under reduced pressure. The residue was subjected to silica gel chromatography eluting with 0-40% EtOAc in hexanes to give the benzyl ether product (912 mg, 69%).

$^1$H NMR (300 MHz, CDCl$_3$) δ 7.35-7.27 (m, 5H), 5.86 (d, J=3.6 Hz, 1H), 4.74 (t, J=4.2 Hz, 1H), 4.60 (s, 2H), 4.42 (m, 1H), 3.69-3.53 (m, 2H), 2.10-2.04 (m, 1H), 1.83-1.77 (m, 1H), 1.52 (s, 3H), 1.33 (s, 3H).

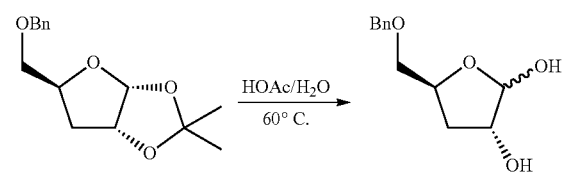

(3R,5S)-5-(benzyloxymethyl)-tetrahydrofuran-2,3-diol

The benzyl ether (910 mg, 3.44 mmol) was dissolved in a 1:1 AcOH and H$_2$O (20 mL) mixture and stirred at 60° C. for 7 h. The mixture was concentrated under reduced pressure and the residue subjected to silica gel chromatography eluting with 0-70% EtOAc in hexanes to give the diol product (705 mg, 91%).

$^1$H NMR (300 MHz, CDCl$_3$) δ 7.36-7.27 (m, 5H), 5.40 (d, J=3.9 Hz, 0.5H), 5.17 (s, 0.5H), 4.67-4.56 (m, 3H), 4.33 (m, 0.5H), 4.24 (d, J=4.8 Hz, 0.5H), 3.71-3.67 (m, 1H), 3.56-3.42 (m, 2H), 2.31-2.22 (m, 1H), 2.08-1.89 (m, 2H).

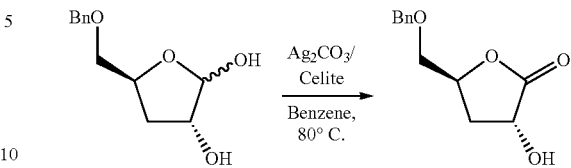

(3R,5S)-5-(benzyloxymethyl)-3-hydroxy-dihydro-furan-2(3H)-one

The diol (705 mg, 3.14 mmol) was dissolved in benzene (30 mL) and treated with a silver carbonate celite mixture (3.46 g, 6.28 mmol). The resultant mixture was stirred at 80° C. under N$_2$(g) for 2 h. The mixture was then cooled to RT, filtered and concentrated under reduced pressure. The residue was subjected to silica gel chromatography eluting with 0-70% EtOAc in hexanes to give the lactone product (600 mg, 86%).

$^1$H NMR (300 MHz, CDCl$_3$) δ 7.39-7.27 (m, 5H), 4.75-4.68 (m, 1H), 4.60-4.49 (m, 2H), 3.74-3.54 (m, 2H), 2.61-2.35 (m, 2H), 2.38-2.28 (m, 1H).

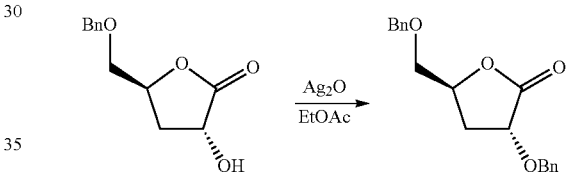

(3R,5S)-3-(benzyloxy)-5-(benzyloxymethyl)-dihydrofuran-2(3H)-one

The lactone (600 mg, 2.7 mmol) was dissolved in EtOAc (30 mL) and treated with silver oxide (626 mg, 2.7 mmol) followed by benzyl bromide (387 μL, 3.24 mmol). The reaction mixture was then stirred at 50° C. under N$_2$(g) for 8 h. Additional silver oxide (300 mg) was then added and the resultant mixture stirred at 50° C. for 16 h. Additional benzyl bromide (50 uL) and silver oxide (150 mg) were added and the mixture stirred for an additional 8 h. The reaction mixture was allowed to cool, filtered and then concentrated under reduced pressure. The residue was subjected to silica gel chromatography eluting with 0-20% EtOAc in hexanes to give the title product (742 mg, 88%).

$^1$H NMR (300 MHz, CDCl$_3$) δ 7.39-7.27 (m, 10H), 4.99 (d, J=11.4 Hz, 1H), 4.72 (m, 2H), 4.56 (m, 2H), 4.39 (t, J=8.1 Hz, 1H), 3.72-3.51 (m, 2H), 2.42-2.25 (m, 2H).

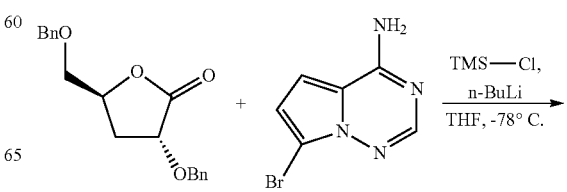

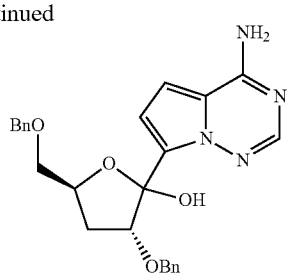

(3R,5S)-2-(4-aminopyrrolo[1,2-f][1,2,4]triazin-7-yl)-3-(benzyloxy)-5-(benzyloxymethyl)-tetrahydrofuran-2-ol The 7-bromopyrrolo[1,2-f][1,2,4]triazin-4-amine (607 mg, 2.85 mmol) was dissolved in anhydrous THF (10 mL) and stirred under Ar(g) at RT. TMSCl (1.1 mL, 8.55 mmol) was added dropwise and the mixture stirred for 2 h. The reaction was concentrated under reduced pressure and then dried under high vacuum. The residue was suspended in THF (20 mL) and stirred under Ar(g) at −78° C. A 2.5M n-BuLi solution in hexane (2.28 mL, 5.7 mmol) was added dropwise over 10 min. and the resultant mixture stirred for 60 min. The lactone (742 mg, 2.37 mmol) dissolved in anhydrous THF (7 mL) was added to the above mixture over 20 min. The reaction mixture was stirred for 2 h. and then quenched with AcOH until pH was 5-6. The mixture was allowed to warm to RT and then diluted with EtOAc. The solution was washed with saturated NaHCO$_3$ solution, saturated NaCl, dried over anhydrous Na$_2$SO$_4$ and concentrated under reduced pressure. The residue was subjected to silica gel chromatography eluting with 0-80% EtOAc in hexanes to give the title product (250 mg, 24%).

LCMS m/z 447.2 [M+H], 445.1 [M−H].

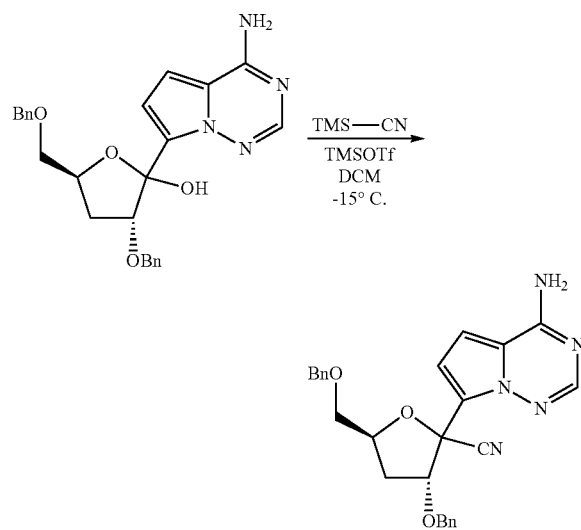

(3R,5S)-2-(4-aminopyrrolo[1,2-f][1,2,4]triazin-7-yl)-3-(benzyloxy)-5-(benzyloxymethyl)-tetrahydrofuran-2-carbonitrile The alcohol (250 mg, 0.56 mmol) was dissolved in anhydrous CH$_2$Cl$_2$ (10 mL) and stirred under Ar(g) at −15° C. TMSCN (448 μL, 3.36 mmol) was added dropwise and the mixture stirred for 10 min. TMSOTf (466 μL, 2.58 mmol) was added dropwise over 10 min and the resultant mixture stirred for 90 min. at −15° C. Additional TMSCN (224 μL, 3 eq.) and TMSOTf (202 μL, 2 eq.) was added and stirring continued for 5 h. Saturated aqueous NaHCO$_3$ solution was added to quench the reaction and the mixture stirred for 10 min. The organic layer was separated and washed with saturated aqueous NaHCO$_3$ solution, saturated NaCl solution, dried over anhydrous Na$_2$SO$_4$, filtered and concentrated under reduced pressure. The residue was subjected to silica gel chromatography eluting with 0-70% EtOAc in hexanes to give the title product (150 mg, 59%).

LCMS m/z 456.3 [M+H], 454.1 [M−H].

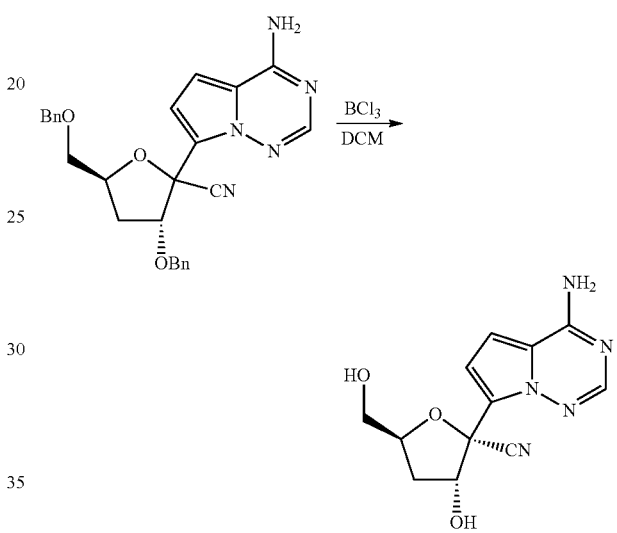

(2R,3R,5S)-2-(4-aminopyrrolo[1,2-f][1,2,4]triazin-7-yl)-3-hydroxy-5-(hydroxymethyl)-tetrahydrofuran-2-carbonitrile (7)

The benzyl ether (150 mg, 0.329 mmol) was dissolved in anhydrous CH$_2$Cl$_2$ (2 mL) and the mixture stirred under Ar(g) at −20° C. A 1M BCl$_3$ solution in CH$_2$Cl$_2$ (724 μL, 0.724 mmol) was added dropwise and the resultant mixture stirred for 2 h. Additional 1M BCl$_3$ in CH$_2$Cl$_2$ (724 μL, 0.724 mmol) was added and stirring continued for 2 h. The mixture was then cooled to −78° C. and slowly treated with a 2:1 mixture of Et$_3$N and MeOH (3 mL). The mixture was stirred for 10 min and then treated with MeOH (10 mL). The reaction was allowed to warm to RT and then concentrated under reduced pressure. The residue was dissolved in MeOH and concentrated under reduced pressure. The residue was dissolved in MeOH again and treated with solid NaHCO$_3$. The mixture was stirred for 5 min and then the solid removed by filtration. The solution was concentrated under reduced pressure and subjected to preparative HPLC to provide the desired product 7 (10 mg, 11%).

$^1$H NMR (300 MHz, D$_2$O) δ 7.71 (s, 1H), 6.75 (d, J=4.5 Hz, 1H), 6.65 (d, J=4.8 Hz, 1H), 4.91 (t, J=6.3 Hz, 1H), 4.57 (m, 1H), 3.67-3.47 (m, 2H), 2.18 (m, 2H).

LCMS m/z 276.1 [M+H], 274.0 [M−H].

(2S)-isopropyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)-phosphorylamino)propanoate (Compound 8)

(2S)-2-ethylbutyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate (Compound 9)

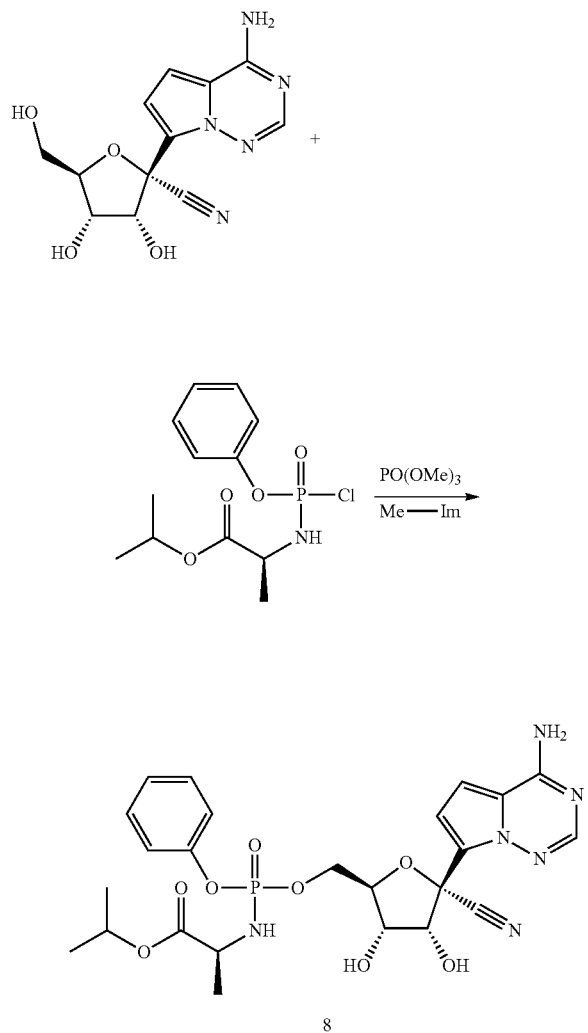

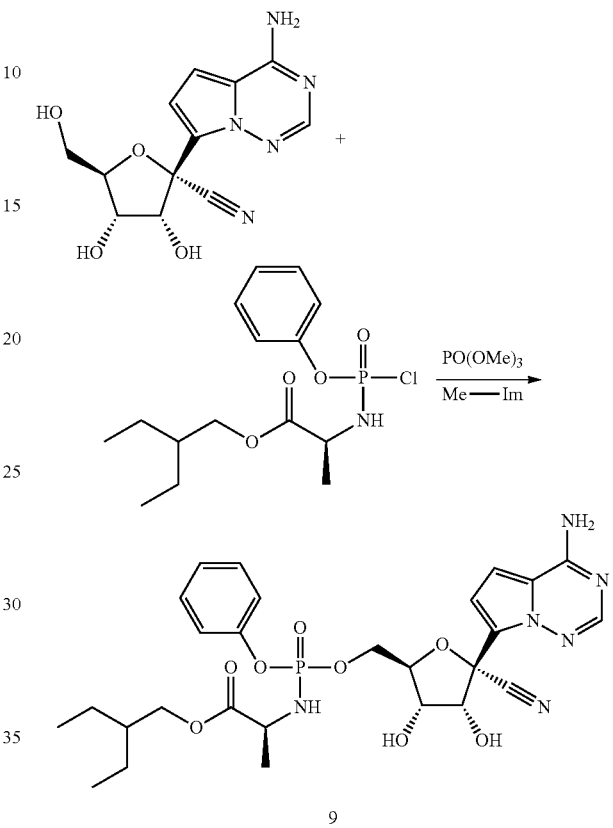

The nucleoside 1 (45 mg, 0.15 mmol) was dissolved in anhydrous trimethyl phosphate (0.5 mL) and the solution stirred under N₂(g) at 0° C. Methyl imidazole (36 μL, 0.45 mmol) was added to the solution. Chlorophosphoramidate C (69 mg, 0.225 mmol) was dissolved in anhydrous THF (0.25 mL) and added dropwise to the nucleoside mixture. When the reaction was complete by LCMS, the reaction mixture was diluted with EtOAc and washed with saturated aqueous NaHCO₃ solution, saturated NaCl, dried over anhydrous Na₂SO₄, filtered and concentrated under reduced pressure. The residue was subjected to silica gel chromatography eluting with 0-5% MeOH in CH₂Cl₂ followed by preparative HPLC to give the product (20.9 mg, 25%).

$^1$H NMR (300 MHz, CD$_3$OD) δ 7.95 (m, 1H), 7.31-6.97 (m, 7H), 4.94 (m, 1H), 4.78 (m, 1H), 4.43 (m, 3H), 4.20 (m, 1H), 3.80 (d, 1H), 1.30-1.18 (m, 9H);

$^{31}$P NMR (121.4 MHz, CD$_3$OD) δ 3.8.

LCMS m/z 561.0 [M+H], 559.0 [M−H].

Prepared from Compound 1 and chloridate B according to the same method as for the preparation of compound 8.

$^1$H NMR (300 MHz, CD$_3$OD) δ 7.87 (m, 1H), 7.31-7.16 (m, 5H), 6.92-6.89 (m, 2H), 4.78 (m, 1H), 4.50-3.80 (m, 7H), 1.45-1.24 (m, 8H), 0.95-0.84 (m, 6H).

$^{31}$P NMR (121.4 MHz, CD$_3$OD) δ 3.7.

LCMS m/z 603.1 [M+H], 601.0 [M−H].

(2S)-ethyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate (Compound 10)

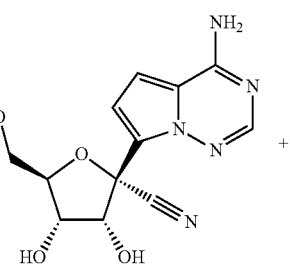

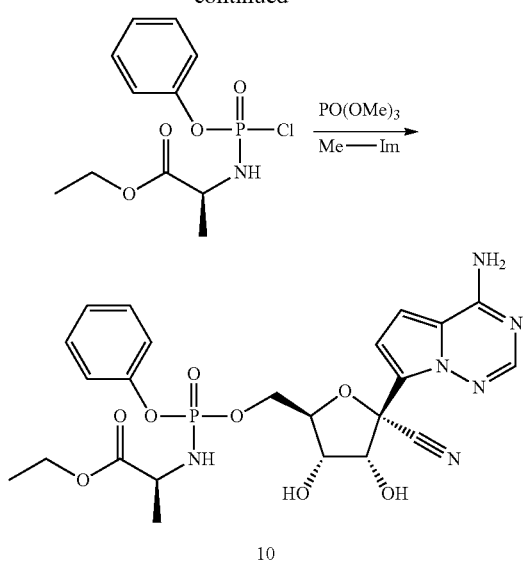

Prepared from Compound 1 and chloridate A using same method as for the preparation of compound 8.

$^1$H NMR (300 MHz, CD$_3$OD) δ 7.95 (m, 1H), 7.32-6.97 (m, 7H), 4.78 (m, 1H), 4.43-4.08 (m, 6H), 3.83 (m, 1H), 1.31-1.18 (m, 6H).

$^{31}$P NMR (121.4 MHz, CD$_3$OD) δ 3.7.

LCMS m/z 547.0 [M+H], 545.0 [M−H].

(2S)-ethyl 2-((((2R,3R,4R,5R)-5-(4-aminopyrrolo[1,2-f][1,2,4]triazin-7-yl)-5-cyano-4-fluoro-3-hydroxytetrahydrofuran-2-yl)methoxy)(phenoxy)phosphorylamino)propanoate (Compound 11)

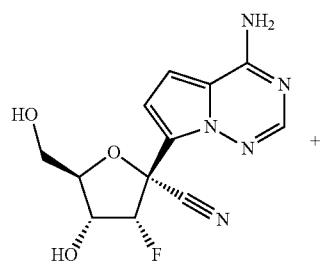

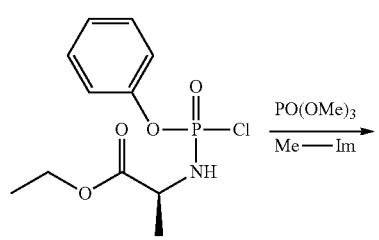

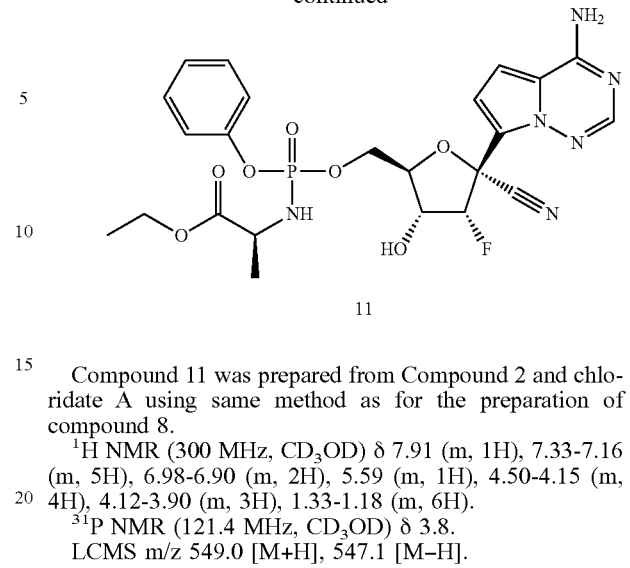

Compound 11 was prepared from Compound 2 and chloridate A using same method as for the preparation of compound 8.

$^1$H NMR (300 MHz, CD$_3$OD) δ 7.91 (m, 1H), 7.33-7.16 (m, 5H), 6.98-6.90 (m, 2H), 5.59 (m, 1H), 4.50-4.15 (m, 4H), 4.12-3.90 (m, 3H), 1.33-1.18 (m, 6H).

$^{31}$P NMR (121.4 MHz, CD$_3$OD) δ 3.8.

LCMS m/z 549.0 [M+H], 547.1 [M−H].

(2S,2'S)-diethyl 2,2'-((((2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(azanediyl)dipropanoate (Compound 12)

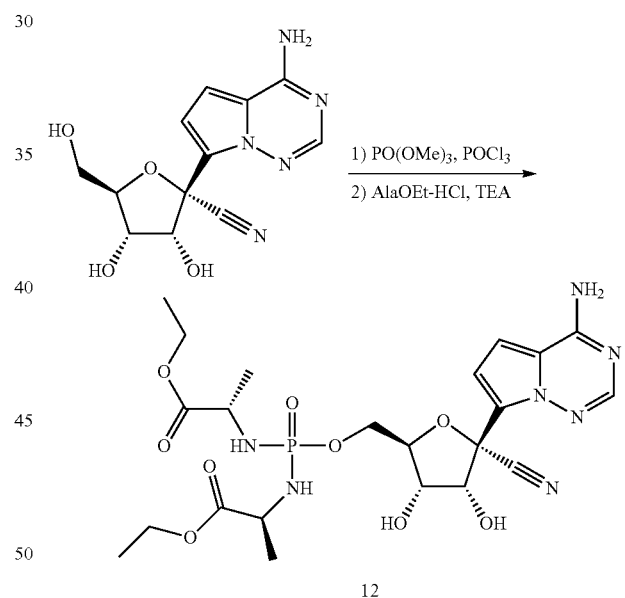

The nucleoside 1 (14.6 mg, 0.05 mmol) was dissolved in anhydrous trimethyl phosphate (0.5 mL) and stirred under N$_2$(g) at RT. POCl$_3$ (9.2 μL, 0.1 mmol) was added and the mixture stirred for 60 min. Alanine ethyl ester hydrochloride (61 mg, 0.4 mmol) and then Et$_3$N (70 μL, 0.5 mmol) was added. The resultant mixture was stirred for 15 min. and then additional Et$_3$N (70 μl, 0.5 mmol) was added to give a solution pH of 9-10. The mixture was stirred for 2 h. and then diluted with EtOAc, washed with saturated aqueous NaHCO$_3$ solution followed by saturated aqueous NaCl solution. The organic layer was dried over anhydrous Na$_2$SO$_4$ and concentrated under reduced pressure. The residue was subjected to preparative HPLC (C$_{18}$ column) to yield the product 12 (5.5 mg, 16%).

¹H NMR (400 MHz, CD₃OD) δ 8.13 (s, 1H), 7.41 (d, J=4.8 Hz, 1H), 7.18 (d, J=4.8 Hz, 1H), 4.78 (d, J=5.6 Hz, 1H), 4.36 (m, 1H), 4.25-4.08 (m, 7H), 3.83 (m, 2H), 1.33-1.23 (m, 12H).

³¹P NMR (121.4 MHz, CD₃OD) δ 13.8.

LCMS m/z 570.0 [M+H], 568.0 [M−H].

(2S,3R,4S,5R)-2-(4-aminopyrrolo[1,2-f][1,2,4]triazin-7-yl)-2-ethynyl-5-(hydroxymethyl)tetrahydrofuran-3,4-diol (Compound 13)

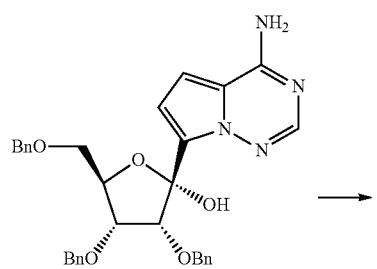

The nucleoside alcohol (0.6 g, 1.08 mmol) (prepared as described in Compound 1 synthesis) was dissolved in anhydrous THF (8 mL) and placed under N₂(g). The reaction mixture was stirred and cooled to 0° C. and then treated with a 0.5N solution of ethynyl magnesium bromide in THF (17.2 mL, 17.2 mmol). The reaction mixture was stirred overnight at RT. AcOH (1.5 mL) was added to quench the reaction. The mixture was concentrated under reduced pressure and the residue redissolved in CH₂Cl₂. The solution subjected to a plug of silica gel eluting with 0 to 80% EtOAc in Hexanes to provide the title product as a crude mixture.

LCMS m/z 579 [M+H].

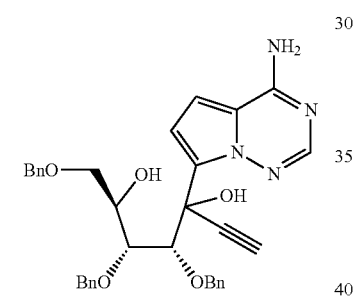

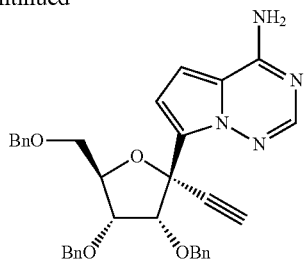

The crude ethynyl alcohol (0.624 g, 1.08 mmol) was dissolved in anhydrous CH₂Cl₂ (10 mL) and placed under N₂(g). The mixture was stirred and sulfonic acid (0.2 mL, 2.74 mmol) was added. The reaction mixture was stirred for 12 h. at RT. When complete by LCMS, Et₃N (0.56 mL) was added to quench the reaction. The reaction was concentrated under reduced pressure and the residue subjected to silica gel chromatography eluting with 0 to 75% EtOAc in Hexanes to yield the ethynyl nucleoside as a mixture of anomers (0.200 g, 33% over 2 steps).

LCMS m/z 561 [M+H].

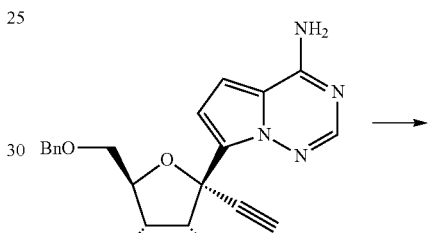

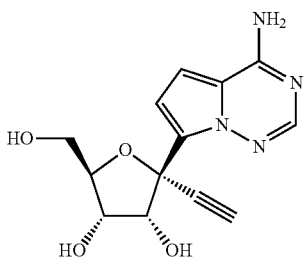

13

The tribenzyl nucleoside (0.650 g, 1.16 mmol) was dissolved in anhydrous CH₂Cl₂ (30 mL) and cooled to −78° C. under N₂(g). A solution of boron tribromide (1 N in CH₂Cl₂, 5.5 mL) was added and the reaction mixture stirred for 1 h. at −78° C. A solution of MeOH (10 mL) and pyridine (2 mL) was added to quench the reaction and the mixture was allowed to rise to RT. The mixture was concentrated under reduced pressure and subjected to preparative HPLC to provide the α-anomer (20 mg) and β-anomer 13 (110 mg)

(β-anomer) ¹H NMR (300 MHz, DMSO) δ 7.81 (s, 1H), 7.76 (br s, 2H), 6.80-6.85 (m, 2H), 5.11 (d, J=7.2 Hz, 1H), 4.90 (d, J=6.0 Hz, 1H), 4.82 (dd, J=7.2, 4.8 Hz, 1H), 4.62 (t, J=6.3 Hz, 1H), 3.95-3.99 (m, 1H), 3.85-3.91 (dd, J=11.4, 5.7 Hz, 1H), 3.61-3.67 (m, 1H), 3.47-3.55 (m, 1H), 3.52 (d, J=0.9 Hz, 1H).

(α-anomer) ¹H NMR (300 MHz, DMSO) δ 7.80 (s, 1H), 7.59 (bs, 2H), 6.80 (d, J=4.5 Hz, 1H), 6.54 (d, J=4.2 Hz, 1H), 5.00 (d, J=7.2 Hz, 1H), 4.89 (d, J=4.8 Hz, 1H), 4.74 (t, J=5.7 Hz, 1H), 4.58 (t, J=4.5 Hz, 1H), 4.27 (m, 1H), 3.88 (m, 1H), 3.64-3.72 (m, 1H), 3.51-3.59 (m, 1H), 3.48 (d, J=0.6 Hz, 1H)

LCMS m/z 291 [M+H].

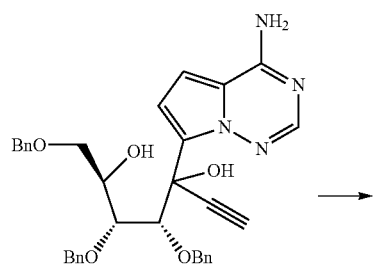

(2R,3R,4R)-5-(4-aminopyrrolo[1,2-f][1,2,4]triazin-7-yl)-1,3,4-tris(benzyloxy)hexane-2,5-diol (Compound 14)

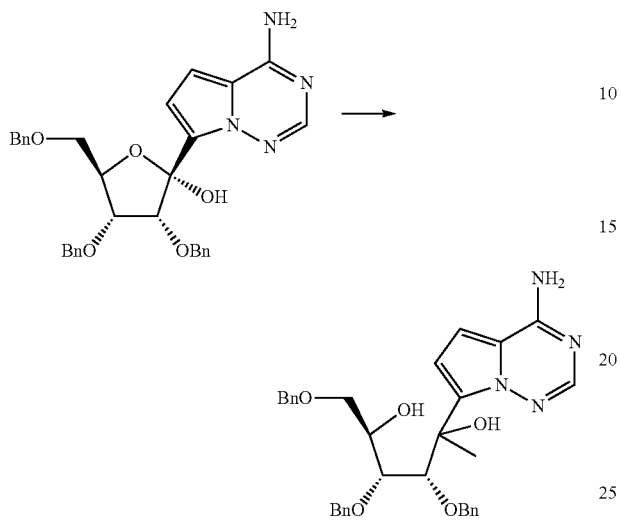

The tribenzyl alcohol from Compound 1 synthesis (0.250 g, 0.453 mmol) was dissolved in anhydrous THF (25 mL) and stirred under N₂(g). The reaction mixture was cooled to 0° C. and then a 3.0 N solution of methyl magnesium chloride in THF (1.2 mL, 3.62 mmol) was added. The reaction mixture was stirred overnight at RT. Acetic acid (1.5 mL) was added to quench the reaction and then the mixture was concentrated under reduced pressure. The residue was redissolved in CH₂Cl₂ and subjected to a plug of silica gel eluting with 0 to 80% EtOAc in hexanes. The crude product (0.452 g) was then used in the next reaction without further purification.

LCMS m/z 569 [M+H].

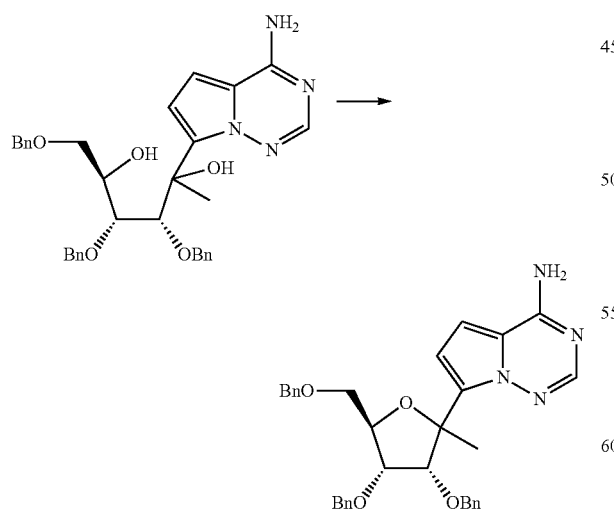

The crude methyl nucleoside (0.452 g, 0.796 mmol) was dissolved in anhydrous CH₂Cl₂ (20 mL) and stirred under N₂(g). Methanesulfonic acid (0.2 mL, 2.78 mmol) was added and the reaction stirred for 12 hr at RT. Et₃N (0.56 mL) was added to quench the reaction and then the mixture concentrated under reduced pressure. The residue was subjected to silica gel chromatography eluting with 0 to 75% EtOAc in Hexanes to yield the product as a mixture of anomers (0.20 g, 46% over 2 steps).

LCMS m/z 551 [M+H].

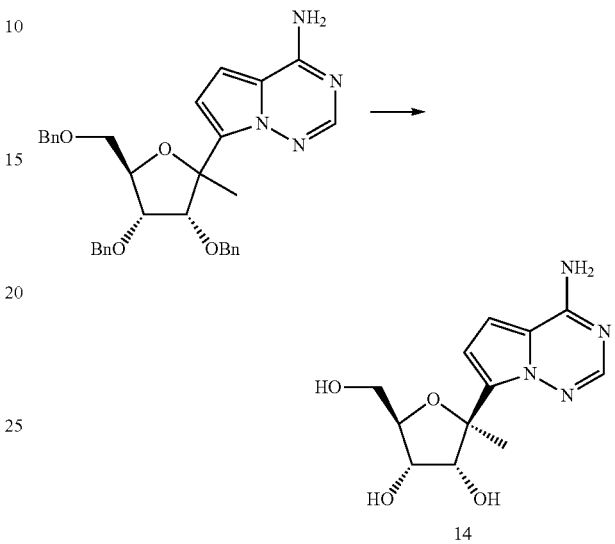

The tribenzyl nucleoside (0.20 g, 0.364 mmol) was dissolved in AcOH (30 mL). and charged with Pd/C (Degussa) (400 mg). The stirred mixture was flushed with N₂(g) three times and then H₂ (g) was introduced, The reaction was stirred under H₂ (g) for 2 h. and then the catalyst removed by filtration. The solution was concentrated under reduced pressure and under the residue was re-dissolved in H₂O. The solution was subjected to preparative HPLC under neutral conditions to provide the α-anomer and β-anomer 14 in 81% yield.

(α-anomer) ¹H NMR (300 MHz, D₂O) δ☐☐ 7.81 (s, 1H), 7.22 (d, 1H), 6.75 (d, 1H), 4.47 (d, 1H), 4.25-4.31 (m, 1H), 3.88-4.95 (m, 1H), 3.58-3.86 (dd, 2H), 1.50 (s, 3H).

(β-anomer) ¹H NMR (300 MHz, D₂O) δ☐☐ 7.91 (s, 1H), 7.26 (d, 1H), 6.90 (d, 1H), 4.61 (d, 1H), 4.00-4.09 (m, 2H), 3.63-3.82 (dd, 2H), 1.67 (s, 3H).

LCMS m/z 281 [M+H].

S,S'-2,2'-((((2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(oxy)bis(ethane-2,1-diyl) bis(2,2-dimethylpropanethioate) (Compound 15

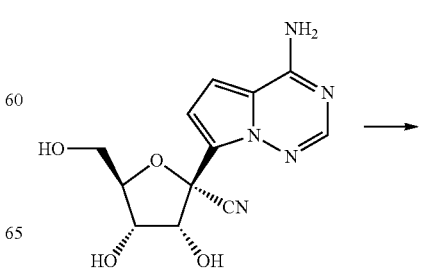

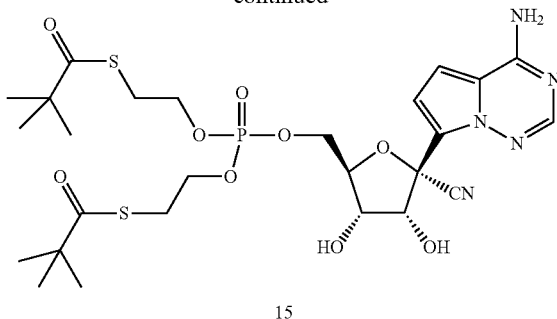

15

The nucleoside 1 (0.028 g, 0.096 mmol) was dissolved in trimethylphosphate (1 mL). The reaction was stirred under $N_2$(g) and then treated with 1H-tetrazole (0.021 g, 0.29 mmol). The reaction mixture was cooled to 0° C. and the phosphane (Nucleoside Nucleotides, Nucleic acids; 14; 3-5; 1995; 763-766. Lefebvre, Isabelle; Pompon, Alain; Perigaud, Christian; Girardet, Jean-Luc; Gosselin, Gilles; et al.) (87 mg, 0.192 mmol) was added. The reaction was stirred for 2 h. and then quenched with 30% hydrogen peroxide (0.120 mL). The mixture was stirred for 30 min at RT and then treated with saturated aqueous sodium thiosulfate (1 mL). The mixture was stirred for 10 min. and then concentrated under reduced pressure. The residue was subjected to preparative HPLC to isolate the title product 15.

$^1$H NMR (300 MHz, $CD_3CN$) δ☐☐ 7.98 (s, 1H), 6.92 (d, 1H), 6.81 (d, 1H), 6.44 (bs, 2H), 4.82 (m, 2H), 4.47 (m, 1H), 4.24 (m, 2H), 4.00 (m, 4H), 3.80 (bs, 1H), 3.11 (m, 4H), 1.24 (s, 9H).
$^{31}$P NMR (121.4 MHz, $CD_3CN$) δ −1.85 (s).
LCMS m/z 661 [M+H].

S,S'-2,2'-((((2R,3S,4R,5S)-5-(4-aminopyrrolo[1,2-f][1,2,4]triazin-7-yl)-5-ethynyl-3,4-dihydroxytetrahydrofuran-2-yl)methoxy)phosphoryl)bis(oxy)bis(ethane-2,1-diyl) bis(2,2-dimethylpropanethioate) (Compound 16)

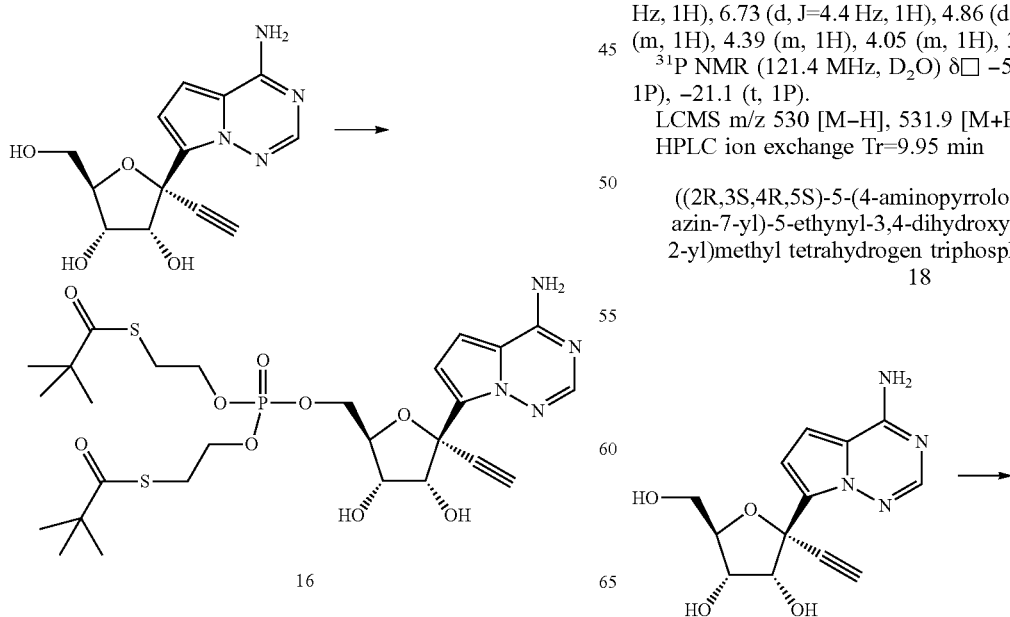

16

Compound 16 was prepared using the same method as compound 15 except substituting compound 13 as the starting nucleoside.

$^1$H NMR (300 MHz, $CD_3CN$) δ☐☐ 7.91 (s, 1H), 6.86 (d, J=4.8 Hz, 1H), 6.76 (d, J=4.5 Hz, 1H), 6.29 (b s, 2H), 4.69 (t, J=2.7 Hz, 1H), 4.58 (d, J=5.7 Hz, 1H), 4.14-4.33 (m, 5H), 3.99-4.07 (m, 4H), 3.53 (d, J=5.4 Hz, 1H), 3.11 (q, J=5.7 Hz, 4H), 1.22 (s, 18H).
LCMS m/z 658.9 [M+]. Tr=2.31

((2R,3S,4R,5R)-5-(4-aminopyrrolo[1,2-f][1,2,4]triazin-7-yl)-5-cyano-3,4-dihydroxytetrahydrofuran-2-yl)methyl tetrahydrogen triphosphate (Compound 17)

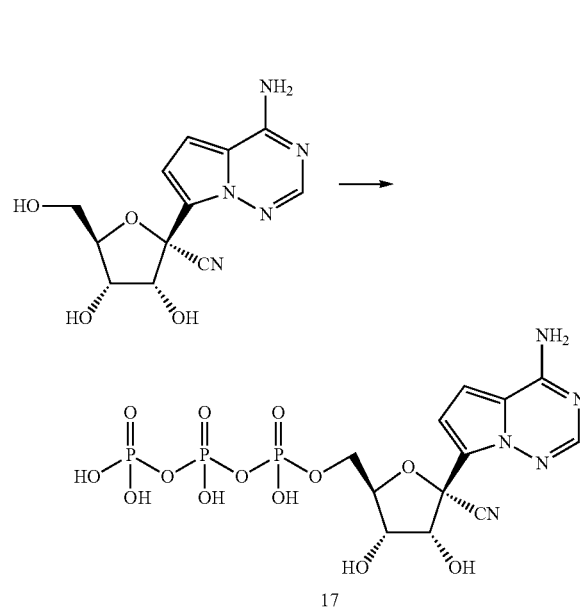

17

Compound 17 was prepared from compound 1 using a similar procedure to the preparation of compound 6. The product was isolated as the sodium salt.

$^1$H NMR (400 MHz, $D_2O$) δ 7.76 (s, 1H), 6.88 (d, J=4.8 Hz, 1H), 6.73 (d, J=4.4 Hz, 1H), 4.86 (d, J=5.2 Hz, 1H), 4.43 (m, 1H), 4.39 (m, 1H), 4.05 (m, 1H), 3.94 (m, 1H)
$^{31}$P NMR (121.4 MHz, $D_2O$) δ☐ −5.4 (d, 1P), −10.8 (d, 1P), −21.1 (t, 1P).
LCMS m/z 530 [M−H], 531.9 [M+H] Tr=0.22 min
HPLC ion exchange Tr=9.95 min ((2R,3S,4R,5S)-5-(4-aminopyrrolo[1,2-f][1,2,4]triazin-7-yl)-5-ethynyl-3,4-dihydroxytetrahydrofuran-2-yl)methyl tetrahydrogen triphosphate (Compound 18)

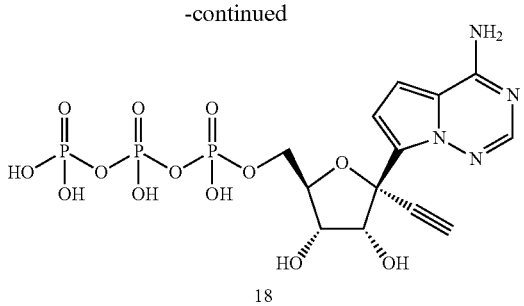

18

Compound 18 was prepared from compound 13 using a similar procedure to the preparation of compound 6. The product was isolated as the TEA salt.

$^1$H NMR (300 MHz, D$_2$O) δ 7.85 (s, 1H), 7.09 (d, J=4.6 Hz, 1H), 6.95 (d, J=4.7 Hz, 1H), 4.23 (m, 2H), 4.08 (m, 2H), 3.06 (q, J=7.4 Hz, 20H), 1.14 (t, J=7.3 Hz, 30H)

$^{31}$P NMR (121.4 MHz, D$_2$O) δ☐ −10.8 (d, 1P), −11.2 (d, 1P), −23.2 (t, 1P).

LCMS m/z 530.8 [M+H], Tr=0.46

HPLC ion exchange Tr=9.40 min ((2R,3S,4R,5S)-5-(4-aminopyrrolo[1,2-f][1,2,4]triazin-7-yl)-3,4-dihydroxy-5-methyltetrahydrofuran-2-yl)methyl tetrahydrogen triphosphate (Compound 19)

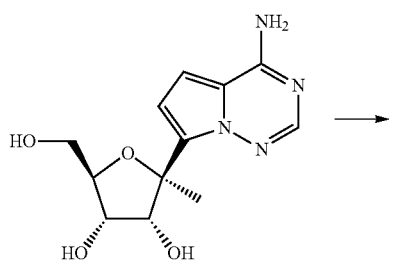

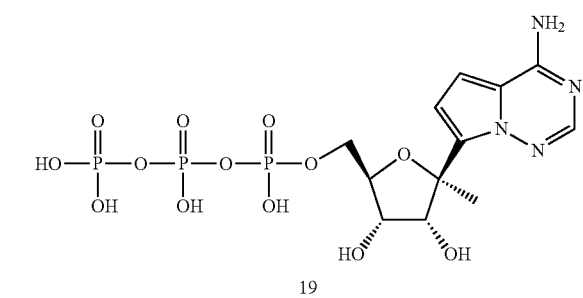

19

Compound 19 was prepared from compound 14 using a similar procedure to the preparation of compound 6.

$^1$H NMR (400 MHz, D$_2$O) δ 7.78 (s, 1H), 6.98 (m, 1H), 6.84 (m, 1H), 4.45 (m, 1H), 4.04 (m, 4H), 1.54 (s, 3H).

$^{31}$P NMR (161 MHz, D$_2$O) δ −10.6 (m), −23.0 (m).

LCMS m/z 521.0 [M+H].

((2R,3R,4R,5R)-5-(4-aminopyrrolo[1,2-f][1,2,4]triazin-7-yl)-5-cyano-4-fluoro-3-hydroxytetrahydrofuran-2-yl)methyl tetrahydrogen triphosphate (Compound 20)

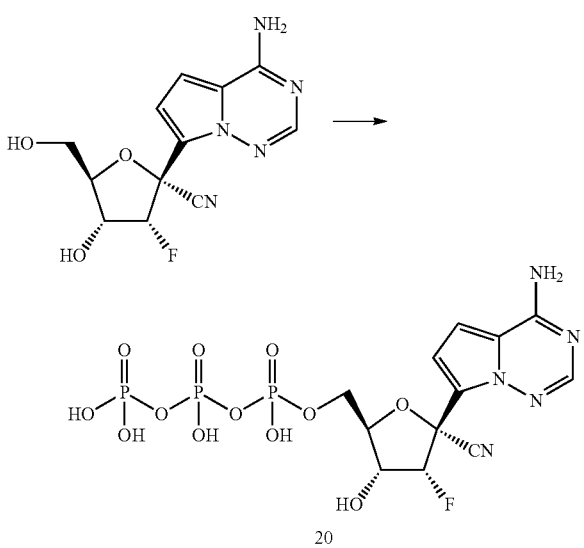

20

Compound 20 was prepared from compound 2 using a similar procedure to the preparation of compound 6.

$^1$H NMR (400 MHz, D$_2$O) δ 7.78 (s, 1H), 6.93 (d, J=4.4 Hz, 1H), 6.78 (d, J=4.8 Hz, 1H), 5.45 (dd, J=53, 4.4 Hz, 1H), 4.38-4.50 (m, 2H), 4.13-4.20 (m, 2H).

$^{31}$P NMR (161 MHz, D$_2$O) δ −5.7 (d, 1P), −11.0 (d, 1P), −21.5 (t, 1P).

LCMS m/z 533.9.0 [M+H], 532.0 [M−H] Tr=1.25 min.

HPLC ion exchange Tr=11.0 min

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Respiratory Syncytial Virus (RSV) Antiviral Activity and Cytotoxicity Assays

Anti-RSV Activity

Antiviral activity against RSV is determined using an in vitro cytoprotection assay in Hep2 cells. In this assay, compounds inhibiting the virus replication exhibit cytoprotective effect against the virus-induced cell killing that can be quantified using a cell viability reagent. The method used is similar to methods previously described in published literature (Chapman et al., *Antimicrob Agents Chemother.* 2007, 51(9):3346-53.)

Hep2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, Md.) is titered before compound testing to determine the appropriate dilution of the virus stock that generates desirable cytopathic effect in Hep2 cells.

For antiviral tests, Hep2 cells are seeded into 96-well plates 24 hours before the assay at a density of 3,000 cells/well. On a separate 96 well plate, compounds to be tested are serially diluted in cell culture media. Eight concentrations in 3-fold serial dilution increments are prepared for each tested compound and 100 uL/well of each dilution is transferred in duplicate onto plates with seeded Hep2 cells. Subsequently, appropriate dilution of virus stock previously determined by titration is prepared in cell culture media and 100 uL/well is added to test plates containing cells and serially diluted compounds. Each plate includes three wells of infected untreated cells and three wells of uninfected cells that served as 0% and 100% virus inhibition control, respectively. Following the infection with RSV, testing plates are incubated for 4 days in a tissue culture incubator. After the incubation, RSV-induced cytopathic effect is determined using a Cell TiterGlo reagent (Promega, Madison, Wis.) followed by a luminescence read-out. The percentage inhibition is calculated for each tested concentration relative to the 0% and 100% inhibition controls and the EC50 value for each compound is determined by non-linear regression as a concentration inhibiting the RSV-induced cytopathic effect by 50%. Ribavirin (purchased from Sigma, St. Louis, Mo.) is used as a positive control for antiviral activity.

Cytotoxicity

Cytotoxicity of tested compounds is determined in uninfected Hep2 cells in parallel with the antiviral activity using the cell viability reagent in a similar fashion as described before for other cell types (Cihlar et al., *Antimicrob Agents Chemother.* 2008, 52(2):655-65). The same protocol as for the determination of antiviral activity is used for the measurement of compound cytotoxicity except that the cells are not infected with RSV. Instead, fresh cell culture media (100 uL/well) without the virus is added to tested plates with cells and prediluted compounds. Cells are then incubated for 4 days followed by a cell viability test using CellTiter Glo reagent and a luminescence read-out. Untreated cell and cells treated with 50 ug/mL puromycin (Sigma, St. Louis, Mo.) are used as 100% and 0% cell viability control, respectively. The percent of cell viability is calculated for each tested compound concentration relative to the 0% and 100% controls and the CC50 value is determined by non-linear regression as a compound concentration reducing the cell viability by 50%.

| Compound | EC50/uM | CC50/uM |
| --- | --- | --- |
| 1 | 0.48 | >100 |
| 10 | 0.18 | 47 |
| 12 | 6.5 | >100 |
| 13 | 34 | >100 |
| 14 | 2.7 | 92 |
| 15 | 0.15 | >100 |
| 16 | 3.3 | >100 |

RSV RNP Preparation

RSV ribonucleoprotein (RNP) complexes were prepared from a method modified from Mason et al (1). HEp-2 cells were plated at a density of $7.1 \times 10^4$ cells/cm$^2$ in MEM+10% fetal bovine serum (FBS) and allowed to attach overnight at 37° C. (5% $CO_2$). Following attachment, the cells were infected with RSV A2 (MOI=5) in 35 mL MEM+2% FBS. At 20 hours post-infection, the media was replaced with MEM+2% FBS supplemented with 2 μg/mL actinomycin D and returned to 37° C. for one hour. The cells were then washed once with PBS and treated with 35 mL of PBS+250 μg/mL lyso-lecithin for one minute, after which all liquid was aspirated. The cells were harvested by scrapping them into 1.2 mL of buffer A [50 mM TRIS acetate (pH 8.0), 100 mM potassium acetate, 1 mM DTT and 2 μg/mL actinomycin D] and lysed by repeated passage through an 18 gauge needle (10 times). The cell lysate was placed in ice for 10 minutes and then centrifuged at 2400 g for 10 minutes at 4° C. The supernatant (S1) was removed and the pellet (P1) was disrupted in 600 uL of Buffer B [10 mM TRIS acetate (pH 8.0), 10 mM potassium acetate and 1.5 mM $MgCl_2$] supplemented with 1% Triton X-100 by repeated passage through an 18 gauge needle (10 times). The resuspended pellet was placed in ice for 10 minutes and then centrifuged at 2400 g for 10 minutes at 4° C. The supernatant (S2) was removed and the pellet (P2) was disrupted in 600 uL of Buffer B supplemented with 0.5% deoxycholate and 0.1% Tween 40. The resuspended pellet was placed in ice for 10 minutes and then centrifuged at 2400 g for 10 minutes at 4° C. The supernatant (S3) fraction, containing the enriched RSV RNP complexes, was collected and the protein concentration determined by UV absorbance at 280 nm. Aliquoted RSV RNP S3 fractions were stored at −80° C.

RSV RNP Assay

Transcription reactions contained 25 μg of crude RSV RNP complexes in 30 μL of reaction buffer [50 mM TRIS-acetate (pH 8.0), 120 mM potassium acetate, 5% glycerol, 4.5 mM $MgCl_2$, 3 mM DTT, 2 mM ethyleneglycol-bis(2-aminoethylether)-tetraacetic acid (EGTA), 50 μg/mL BSA, 2.5 U RNasin (Promega), ATP, GTP, UTP, CTP and 1.5 uCi [α-$^{32}$P] NTP (3000 Ci/mmol)]. The radiolabled nucleotide used in the transcription assay was selected to match the nucleotide analog being evaluated for inhibition of RSV RNP transcription. Cold, competitive NTP was added at a final concentration of one-half its $K_m$ (ATP=20 μM, GTP=12.5 μM, UTP=6 μM and CTP=2 μM). The three remaining nucleotides were added at a final concentration of 100 μM.

To determine whether nucleotide analogs inhibited RSV RNP transcription, compounds were added using a 6 step serial dilution in 5-fold increments. Following a 90 minute incubation at 30° C., the RNP reactions were stopped with 350 μL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2M formaldehyde. The agarose gel was dried and exposed to a Storm phosphorimager screen and developed using a Storm phosphorimager (GE Healthcare). The concentration of compound that reduced total radiolabed transcripts by 50% ($IC_{50}$) was calculated by non-linear regression analysis of two replicates.

REFERENCE

1) Mason, S., Lawetz, C., Gaudette, Y., Do, F., Scouten, E., Lagace, L., Simoneau, B. and Liuzzi, M. (2004) Polyadenylation-dependent screening assay for respiratory syncytial virus RNA transcriptase activity and identification of an inhibitor. Nucleic Acids Research, 32, 4758-4767.

| Compound | IC50/uM |
| --- | --- |
| 6 | 3.6 |
| 17 | 1.5 |
| 18 | 1.6 |
| 19 | 1.5 |
| 20 | 0.8 |

Description of the Parainfluenza Cytoprotection Assay

The Parainfluenza Cytoprotection assay uses Vero cells and Parainfluenza 3 strain C 243. Briefly virus and cells are mixed in the presence of test compound and incubated for 7 days. The virus is pre-titered such that control wells exhibit 85 to 95% loss of cell viability due to virus replication. Therefore, antiviral effect or cytoprotection is observed when compounds prevent virus replication. Each assay plate contains cell control wells (cells only), virus control wells (cells plus virus), compound toxicity control wells (cells plus compound only), compound colorimetric control wells (compound only), as well as experimental wells (compound plus cells plus virus). Cytoprotection and compound cytotoxicity are assessed by MTS (CellTiter®96 Reagent, Promega, Madison Wis.) dye reduction. The % reduction in viral cytopathic effects (CPE) is determined and reported; $IC_{50}$ (concentration inhibiting virus replication by 50%), $TC_{50}$ (concentration resulting in 50% cell death) and a calculated TI (therapeutic index $TC_{50}/IC_{50}$) are provided along with a graphical representation of the antiviral activity and compound cytotoxicity when compounds are tested in dose-response. Each assay includes ribavirin as a positive control.

Cell Preparation

Vero cells (Kidney, African green monkey, *Cercopithecus aethiops*) were obtained from the American Type Culture Collection (ATCC, Rockville, Md.) and are grown in Dulbecco's Modified Eagle's Medium (DMEM) supplemented with 10% fetal bovine serum (FBS), 2.0 mM L-Glutamine, 100 units/ml Penicillin and 100 ug/ml Streptomycin ("growth medium"). Cells are sub-cultured twice a week at a split ratio of 1:10 using standard cell culture techniques. Total cell number and percent viability determinations are performed using a hemacytometer and trypan blue exclusion. Cell viability must be greater than 95% for the cells to be utilized in the assay. The cells are seeded in 96-well tissue culture plates the day before the assay at a concentration of $1 \times 10^4$ cells/well.

Virus Preparation

The virus used for this assay is Parainfluenza 3 strain C 243. This virus was obtained from the American Type Culture Collection (ATCC) and was grown in Vero cells for the production of stock virus pools. For each assay, a pre-titered aliquot of virus is removed from the freezer (−80° C.) and allowed to thaw slowly to room temperature in a biological safety cabinet. The virus is resuspended and diluted into tissue culture medium such that the amount of virus added to each well is the amount determined to give between 85 to 95% cell killing at 6-7 days post-infection.

MTS Staining for Cell Viability

At assay termination (7 days post-infection), the assay plates are stained with the soluble tetrazolium-based dye MTS (3-(4,5-dimethylthiazol-2-yl)-5-(3-carboxymethoxyphenyl)-2-(4-sulfophenyl)-2H-tetrazolium; CellTiter® 96 Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. This reagent is a stable, single solution that does not require preparation before use. At termination of the assay, 20-25 μL of MTS reagent is added per well and the microtiter plates are then incubated for 4-6 hrs at 37° C., 5% $CO_2$ to assess cell viability. Adhesive plate sealers are used in place of the lids, the sealed plate is inverted several times to mix the soluble formazan product and the plate is read spectrophotometrically at 490/650 nm with a Molecular Devices Vmax or SpectraMax Plus plate reader.

Data Analysis

Using an in-house computer program % Cytopathic Effect (CPE) Reduction, % Cell Viability, $IC_{25}$, $IC_{50}$, $IC_{95}$, $TC_{25}$, $TC_{50}$, and $TC_{95}$ and other indices are calculated and the graphical results summary is displayed. Raw data for both antiviral activity and toxicity with a graphical representation of the data are provided in a printout summarizing the individual compound activity. The Table below shows the activity of selected compounds against Parainfluenza 3 virus.

| Compound | IC50/uM | TC50/uM |
| --- | --- | --- |
| 1 | 1.71 | >30 |
| 14 | 5.23 | >30 |

The specific pharmacological and biochemical responses observed in the assays described may vary according to and depending on the particular active compound selected or whether there are present pharmaceutical carriers, as well as the type of formulation and mode of administration employed, and such expected variations or differences in the results are contemplated in accordance with practice of the present invention.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A compound having the structure of Formula III or a pharmaceutically acceptable salt thereof:

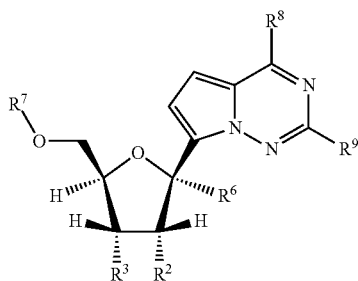

wherein
$R^2$ and $R^3$ are each $OR^a$;
$R^6$ is CN;
$R^7$ is $(C=O)R^{11}$ or

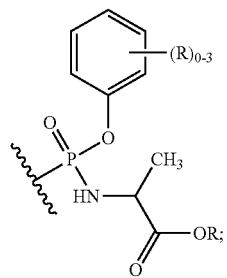

$R^8$ is $NH_2$;
$R^9$ is H;
each occurrence of $R^a$ is independently H or $(C=O)R^{11}$;
each occurrence of $R^{11}$ is independently H or $(C_1-C_8)$ alkyl which is optionally substituted by $NH_2$; and
each occurrence of R is independently H or $(C_1-C_8)$alkyl.

2. The compound of claim 1, wherein $R^7$ is

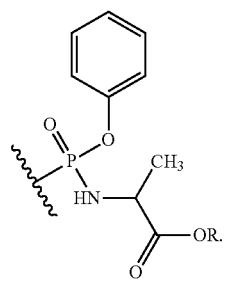

3. The compound of claim 2, wherein R is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl.

4. The compound of claim 1, wherein $R^2$ and $R^3$ are each OH.

5. The compound of claim 4, wherein $R^7$ is —(C=O)—$(C_1-C_8)$alkyl; wherein the $(C_1-C_8)$alkyl of $R^7$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted by $NH_2$.

6. The compound of claim 5, wherein $R^7$ is —(C=O)—$CH(CH_3)_2$.

7. The compound of claim 5, wherein $R^7$ is —(C=O)—$CH(NH_2)CH(CH_3)_2$.

8. The compound of claim 1, wherein $R^2$ and $R^3$ are each —O(C=O)$(C_1-C_8)$alkyl, wherein the $(C_1-C_8)$alkyl groups of $R^2$ and $R^3$ are each optionally substituted with $NH_2$.

9. The compound of claim 8, wherein the $(C_1-C_8)$alkyl groups of $R^2$ and $R^3$ are each selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted with $NH_2$.

10. The compound of claim 9, wherein each of $R^2$ and $R^3$ is selected from the group consisting of —O(C=O)—CH$(CH_3)_2$ and —O(C=O)—$CH(NH_2)CH(CH_3)_2$.

11. The compound of claim 10, wherein $R^2$ and $R^3$ are —O(C=O)—$CH(NH_2)CH(CH_3)_2$ and —O(C=O)—CH$(CH_3)_2$, respectively; —O(C=O)—CH$(CH_3)_2$ and —O(C=O)—$CH(NH_2)CH(CH_3)_2$, respectively; or —O(C=O)—$CH(NH_2)CH(CH_3)_2$ and —O(C=O)—CH$(NH_2)CH(CH_3)_2$, respectively.

12. The compound of claim 10, wherein $R^2$ and $R^3$ are each —O(C=O)—CH$(CH_3)_2$.

13. The compound of claim 8, wherein $R^7$ is —(C=O)—$(C_1-C_8)$alkyl, wherein the $(C_1-C_8)$alkyl of $R^7$ is optionally substituted by $NH_2$.

14. The compound of claim 13, wherein the $(C_1-C_8)$alkyl of $R^7$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted by $NH_2$.

15. The compound of claim 14, wherein $R^7$ is —(C=O)—$CH(CH_3)_2$.

16. The compound of claim 14, wherein $R^7$ is —(C=O)—$CH(NH_2)CH(CH_3)_2$.

17. The compound of claim 8, wherein $R^2$ is —O(C=O)—CH$(CH_3)_2$, $R^3$ is —O(C=O)—CH$(CH_3)_2$, and $R^7$ is —(C=O)—$CH(CH_3)_2$.

18. The compound of claim 1, wherein $R^2$ is OH and $R^3$ is —O(C=O)$(C_1-C_8)$alkyl, wherein the $(C_1-C_8)$alkyl of $R^3$ is optionally substituted by $NH_2$.

19. The compound of claim 18, wherein the $(C_1-C_8)$alkyl of $R^3$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted by $NH_2$.

20. The compound of claim 19, wherein $R^3$ is —O(C=O)—$CH(CH_3)_2$.

21. The compound of claim 19, wherein $R^3$ is —O(C=O)—$CH(NH_2)CH(CH_3)_2$.

22. The compound of claim 18, wherein $R^7$ is —(C=O)—$(C_1-C_8)$alkyl; wherein the $(C_1-C_8)$alkyl of $R^7$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted by $NH_2$.

23. The compound of claim 22, wherein $R^7$ is —(C=O)—$CH(CH_3)_2$.

24. The compound of claim 22, wherein $R^7$ is —(C=O)—CH($NH_2$)CH($CH_3$)$_2$.

25. The compound of claim 1, wherein $R^3$ is OH and $R^2$ is —O(C=O)($C_1$-$C_8$)alkyl, wherein the ($C_1$-$C_8$)alkyl of $R^2$ is optionally substituted by $NH_2$.

26. The compound of claim 25, wherein the ($C_1$-$C_8$)alkyl of $R^2$ is selected from the group consisting of methyl, ethyl, n-propyl, i-propyl, or 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted by $NH_2$.

27. The compound of claim 26, wherein $R^2$ is —O(C=O)—CH($CH_3$)$_2$.

28. The compound of claim 26, wherein $R^2$ is —O(C=O)—CH($NH_2$)CH($CH_3$)$_2$.

29. The compound of claim 25, wherein $R^7$ is —(C=O)—($C_1$-$C_8$)alkyl; wherein the ($C_1$-$C_8$)alkyl of $R^7$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl, each of which is optionally substituted by $NH_2$.

30. The compound of claim 29, wherein $R^7$ is —(C=O)—CH($CH_3$)$_2$.

31. The compound of claim 29, wherein $R^7$ is —(C=O)—CH($NH_2$)CH($CH_3$)$_2$.

32. The compound of claim 1, wherein $R^2$ and $R^3$ are each —O(C=O)($C_1$-$C_8$)alkyl.

33. The compound of claim 32, wherein the ($C_1$-$C_8$)alkyl groups of $R^2$ and $R^3$ are each selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl.

34. The compound of claim 32, wherein $R^7$ is —(C=O)—($C_1$-$C_8$)alkyl.

35. The compound of claim 34, wherein the ($C_1$-$C_8$)alkyl of $R^7$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl.

36. The compound of claim 4, wherein $R^7$ is —(C=O)—($C_1$-$C_8$)alkyl.

37. The compound of claim 36, wherein the ($C_1$-$C_8$)alkyl of $R^7$ is selected from the group consisting of methyl, ethyl, n-propyl, i-propyl, 1-butyl, 2-methyl-1-propyl, 2-butyl, 2-methyl-2-propyl, 2-pentyl, 3-pentyl, 2-methyl-2-butyl, 3-methyl-2-butyl, 3-methyl-1-butyl, and 2-methyl-1-butyl.

* * * * *

UNITED STATES PATENT AND TRADEMARK OFFICE
CERTIFICATE OF CORRECTION

| | |
|---|---|
| PATENT NO. | : 11,492,353 B2 |
| APPLICATION NO. | : 16/879491 |
| DATED | : November 8, 2022 |
| INVENTOR(S) | : Richard L. Mackman et al. |

It is certified that error appears in the above-identified patent and that said Letters Patent is hereby corrected as shown below:

On the Title Page

Item [60] Column 1, Line 1, delete "Division" and insert -- Continuation --.

In the Claims

Column 117, Line 22, Claim 1, delete "(C=O)R$^{11}$" and insert -- —(C=O)R$^{11}$ --.

Column 117, Line 39, Claim 1, delete "(C=O)R$^{11}$" and insert -- —(C=O)R$^{11}$ --.

Signed and Sealed this
Twenty-seventh Day of December, 2022

Katherine Kelly Vidal
*Director of the United States Patent and Trademark Office*